United States Patent
Liu et al.

(10) Patent No.: US 6,972,340 B2
(45) Date of Patent: Dec. 6, 2005

(54) SELECTIVE PROTEIN TYROSINE PHOSPHATATASE INHIBITORS

(75) Inventors: Gang Liu, Gurnee, IL (US); Bruce G. Szczepankiewicz, Lindenhurst, IL (US); Zhonghua Pei, Libertyville, IL (US); Zhili Xin, Lake Bluff, IL (US); David A. Janowick, Beach Park, IL (US)

(73) Assignee: Abbott Laboratories, Abbott Park, IL (US)

( * ) Notice: Subject to any disclaimer, the term of this patent is extended or adjusted under 35 U.S.C. 154(b) by 289 days.

(21) Appl. No.: 09/941,471

(22) Filed: Aug. 29, 2001

(65) Prior Publication Data

US 2002/0072516 A1 Jun. 13, 2002

Related U.S. Application Data

(63) Continuation-in-part of application No. 09/918,928, filed on Jul. 31, 2001, now abandoned, which is a continuation-in-part of application No. 09/650,922, filed on Aug. 29, 2000, now abandoned.

(60) Provisional application No. 60/228,651, filed on Aug. 29, 2000.

(51) Int. Cl.[7] ..................... C07C 321/00; C07C 271/00; C07C 229/00; C07C 69/76

(52) U.S. Cl. ................. 560/41; 560/9; 560/24; 560/26; 560/27; 560/30; 560/33; 560/75; 560/102; 560/109; 560/111; 560/112; 560/153

(58) Field of Search ................. 560/9, 24, 26, 560/27, 30, 33, 75, 102, 105, 109, 111–112, 153, 41; 514/217, 290, 310, 416, 534; 540/588, 593; 546/143; 548/79, 470

(56) References Cited

U.S. PATENT DOCUMENTS

| 3,987,192 | A | 10/1976 | Wright | 424/304 |
|---|---|---|---|---|
| 4,091,011 | A | 5/1978 | Wright | |
| 4,230,484 | A | 10/1980 | Batch et al. | 71/111 |
| 2002/0035137 | A1 * | 3/2002 | Liu et al. | 514/360 |
| 2002/0169157 | A1 * | 11/2002 | Liu et al. | 514/217 |

FOREIGN PATENT DOCUMENTS

| FR | 1517896 | 3/1968 |
|---|---|---|
| WO | 99/46236 | 9/1999 |
| WO | 9946237 | 9/1999 |
| WO | 01/17516 | 3/2001 |
| WO | 01/19830 | 3/2001 |
| WO | 01/19831 | 3/2001 |
| WO | 0218323 | 3/2002 |

OTHER PUBLICATIONS

Iversen, L.R., et al., "Structure–based Design of a Low Molecular Weight, Nonphosphorus, Nonpeptide, and Highly Selective Inhibitor of Protein–tyrosine Phosphatase 1B", *Journ. Of Biol. Chem.*, 275(14):10300–10307 (2000).

Peters, G. H., et al., "Residue 259 Is a Key Determinant of Substrate Specificity of Protein–tyrosine Phosphatases 1B and α*", *Journ. Of Biol. Chem.*, 275(24):18201–18209 (2000).

Tony Hunter, "The Phosphorylation of proteins on tyrosine: its role in cell growth and disease", Phil. Trans. R. Soc. Lond. B (1998) 353: 583–605.

Chan et al, "The Role of Protein Tyrosine Kinases and Protein Tyrosine Phosphatases in T Cell Antigen Receptor Signal Transduction", Annu. Rev. Immunol. (1994) 12: 555–592.

Zhong–Yin Zhang, "Structure, Mechanism, and Specificity of Protein–Tyrosine Phosphatases", Current Topics In Cellular Regulation (1997) 35:21–68.

Matozaki et al, "Roles of Protein–Tyrosine Phosphatases in Growth Factor Signalling", Cell. Signal (1996) vol. 8, No. 1: 113–119.

Barry J. Goldstein, "Regulation of Insulin Receptor Signaling by Protein–Tyrosine Dephosphorylation", Receptor (1993) 3:1–15.

Faure et al, "The Dephosphorylation of Insulin and Epidermal Growth Factor Receptors", Journal of Biol. Chemistry (1992) 267:11215–11221.

Seely et al., "Protein Tyrosine Phosphatase 1B Interacts with the Activated Insulin Receptor", Diabetes (1996) 45: 1379–1385.

Ahmad et al, "Osmotic Loading of Neutralizing Antibodies Demonstrates a Role for Protein–Tyrosine Phosphatase 1 B in Negative Regulation of the Insulin Action Pathway", J. Biol. Chem. (1995)270:20503–20508.

Elchebly et al, "Increased Insulin Sensitivity and Obesity Resistance in Mice Lacking the Protein Tyrosine Phosphatase–1B Gene", Science (1999) 283: 1544–1548.

Klaman et al, "Increased Energy Expenditure, Decreased Adiposity and Tissue–Specific Insulin Sensitivity in Protein–Tyrosine Phosphastase 1B–Deficient Mice", Molecular and Cellular Biology (2000) 20: 5479–5489.

(Continued)

Primary Examiner—Cecilia J. Tsang
Assistant Examiner—Taylor V. Oh
(74) Attorney, Agent, or Firm—Johanna M. Corbin; Cheryl L. Becker

(57) ABSTRACT

Compounds of formula (I)

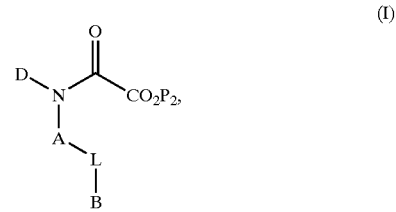

(I)

or therapeutically acceptable salts thereof, are selective protein tyrosine kinase-B (PTP1B) inhibitors. Preparation of the compounds, compositions containing the compounds, and treatment of disorders using the compounds are disclosed.

72 Claims, No Drawings-

OTHER PUBLICATIONS

Hunter et al, "Protein–Tyrosine Kinases", Ann. Rev. Biochem (1985) 54:897–930.

Wiener et al, "Overexpression of the Protein Tyrosine Phosphatase PTPIB in Human Breast Cancer: Association with p185c–erB–2 Protein Expression", J. Natl. Cancer Inst. (1994) 86: 372–378.

Noguchi et al, Role of SH–PTP2, a Protein–Tyrosine Phosphatase with Src Homology 2 Domains, in Insulin–Stimulated Ras Activation:, Molecular Cellular Biology (1994) 14:6674–6682.

Flint et al, "Multi–site phosphorylation of the protein tyrosine phosphatase, PTPIB: identification of cell cycle regulated and phorbol ester stimulated sites of phosphorylation", The EMBO Journal (1993) 12: 1937–1946.

Mauto et al, "Identification of a Hormonally Regulated Protein Tyrosine Phosphatase Associated with Bone and Testicular Differentiation", Journal of Biological Chemistry (1994) 269: 30659–30667.

Wang et al, "Mechanism of Inhibition of Protein–Tyrosine Phosphatases by Disodium Aurothiomalate", Biochemical Pharmacology (1997) 54:703–711.

Mauro et al, "Zip Codes' direct intracellular protein tyrosine phosphatases to the correct cellular 'address'", TIBS (1994) 19: 151–155.

Tonks et al, "Purification of the Major Protein–tyrosine–phosphatases of Human Placenta", J. Biol. Chem. (1998) 263: 6722–6730.

Cool et al, "cDNA isolated from a human T–cell library encodes a member of the protein–tyrosine–phosphatase family", Proc. Natl. Acad. Sci. USA (1989) 86: 5257–5261.

Lombroso et al, "Molecular characterization of a protein–tyrosine–phosphatase enriched striatum", Proc. Natl. Acad. Sci. USA (1991) 88: 7242–7246.

Plutzky et al, " Isolation of a src homology 2–containing tyrosine phosphatase", Proc. Natl. Acad. Sci USA (1992) 89: 1123–1127.

Vogel et al, "Activation of a Phosphotyrosine Phosphatase by Tyrosine Phosphorylation", Science (1993) 259: 1611–1614.

Feng et al, "SH2–Containing Phosphotyrosine Phosphatases as a target of Protein–Tyrosine Kinases", Science (1993) 259: 1607–1611.

Ralph et al, "Structural Variants of Human T200 glycoprotein (leukocyte–common antigen)" The EMBO Journal (1987) 6: 1251–1257.

Streuli et al, "A New Member of the Immunoglobulin Super Family that has a Cytoplamic Region Homologous to the Leukocyte Common Antigen", J. Exp. Med. (1988) 168(5): 1523–1530.

Krueger et al, "Structural Diversity and Evolution of Human Receptor–Like Protein Tyrosine Phosphatases", The EMBO Journal (1990) 9: 3241–3252.

Beaulieu et al, "Ligands for the tyrosine kinase p56lck SH2 domain: Discovery of potent dipeptide derivatives with monocharged, nonhydrolyzable phosphate replacements" J. Med. Chem. (1999) 42: 1757–1766.

Andersen et al, "2–(Oxalylamino)–benzoic acid Is a general, competitive inhibitor of protein–tyrosine phosphatases" J. Biol. Chem. (2000) 275: 7101–7108.

Iversen et al, "Structure–based design of a low molecular weight nonphosphorus, nonpeptide, and highly selective inhibitor of protein–tyrosine phosphatase 1B", J. Biol. Chem. (2000) 275: 10300–10307.

Abstract XP002195161. Podesva, C et al: Canadian Journal of Chemistry (1968) 46: 435–439.

Abstract XP002195162. Peet, Norton P. et al: Journal of Heterocyclic Chemistry (1980) 17: 1513–1518.

Abstract XP002195163. Lee, Sang–Gi et al: Synthetic Communications (1996) 26: 4623–4632.

Abstract XP002195164. Ye, Jia–Hai et al: Tetrahedron Letters (1999) 40: 1365–1368.

Abstract XP002195166. Cannizzo, Sergio et al: Journal of Heterocyclic Chemistry (1990) 27:2175–2179.

* cited by examiner

SELECTIVE PROTEIN TYROSINE PHOSPHATATASE INHIBITORS

This application claims the benefit of Provisional Application No. 60/228,651 filed Aug. 29, 2000.

This patent application is a continuation-in-part of U.S. application Ser. No. 09/918,928, filed on Jul. 31, 2001, abandoned, which is a continuation-in-part of U.S. application Ser. No. 09/650,922, filed on Aug. 29, 2000, abandoned.

TECHNICAL FIELD

The present invention is directed to compounds useful for the selective inhibition of protein tyrosine phosphatase-1B (PTP1B) preparation of the compounds, compositions containing the compounds and the treatment of disorders using the compounds.

BACKGROUND OF THE INVENTION

Insulin is an important regulator of different metabolic processes and plays a key role in the control of blood glucose. Defects related to its synthesis and signaling lead to diabetes mellitus. Binding of insulin to the insulin receptor (IR) causes rapid autophosphorylation of several tyrosine residues in the intracellular part of the β-subunit. Three closely positioned tyrosine residues (the tyrosine-1150 domain) must be phosphorylated to obtain maximum activity of the insulin receptor tyrosine kinase (IRTK) which transmits the further signals via tyrosine phosphorylation of other cellular substrates, including insulin receptor substrate-1 (IRS-1).

Protein phosphorylation is a well-recognized cellular mechanism for transducing and regulating signals during different stages of cellular function (Hunter, *Phil. Trans. R. Soc. Lond. B.*353: 583–605 (1998); Chan et al., *Annu. Rev. Immunol.* 12: 555–592 (1994); Zhang, *Curr. Top. Cell. Reg.* 35: 21–68 (1997); Matozaki and Kasuga, *Cell. Signal.* 8: 113–119 (1996)). There are at least two major classes of phosphatases, namely, (1) Those that dephosphorylate proteins that contain a phosphate group(s) on a serine or theronine moiety (termed Ser/Thr. Phosphatases or duel specificity phosphatases or DSPs) and (2) those that remove a phosphate group(s) from the amino acid tyrosine (termed protein tyrosine phosphatases or PTPases or PTPs).

Several studies clearly indicate that the activity of the auto-phosphorylated IRTK can be reversed by dephosphorylation in vitro (reviewed in Goldstein, *Receptor* 3: 1–15 (1993)) with the tri-phosphorylated tyrosine-1150 domain being the most sensitive target for PTPases. This tri-phosphorylated tyrosine functions as a control switch of IRTK activity and the IRTK appears to be tightly regulated by PTP-mediated dephosphorylation in vivo (Faure et al. *J. Biol. Chem.* 267: 11215–11221 (1992)).

PTP1B has been identified as at least one of the major phosphatases involved in the IRTK regulation through studies conducted both in vitro (Seely et al. *Diabetes* 45: 1379–1385 (1996)) and in vivo using PTP1B neutralizing antibodies (Ahmad et al. *J. Biol. Chem.* 270: 20503–20508 (1995)). Two independent studies have indicated that PTP 1B knock-out mice have increased glucose tolerance, increased insulin sensitivity and decreased weight gain on a high fat diet (Elchebly et al. *Science* 283: 1544–1548 (1999) and Klaman et al. *Mol. Cell. Biol.* 20: 5479–5489 (2000)). Overexpression or altered activity of tyrosine phosphatase PTP1B can contribute to the progression of various disorders, including insulin resistance and diabetes (*Ann. Rev. Biochem.* 54: 897–930 (1985)). Furthermore, there is evidence which suggests inhibition of protein tyrosine phosphatase PTP1B is therapeutically beneficial for the treatment of disorders such as type I and II diabetes, obesity, autoimmune disorder, acute and chronic inflammation, osteoporosis and various forms of cancer (*J. Natl. Cancer Inst.* 86: 372–378 (1994); *Mol. Cell. Biol.* 14: 6674–6682 (1994); *The EMBO J.*, 12: 1937–1946 (1993); *J. Biol. Chem.* 269: 30659–30667 (1994); and *Biochemical Pharmacology* 54: 703–711(1997)).

The PTPases are a family of enzymes that can be classified into two subgroups, namely, 1) intracellular or non-transmembrane PTPases and 2) receptor-type or transmembrane PTPases. Most known intracellular type PTPases contain a single conserved catalytic phosphatase domain consisting of 220–240 amino acid residues. The region outside the PTPase domains are believed to play important roles in localizing the intracellular PTPases subcellularly (Mauro, L. J. and Dixon J. E. *TIBS* 19: 151–155 (1994)). The first intracellular PTPases to be purified and characterized was PTP1B (Tonks, et al. *J. Biol. Chem.* 263: 6722–6730 (1988)). Other examples of intracellular PTPases include (1) T-cell PTPase/TC-PTP (Cool et al. *Proc. Natl. Acad. Sci. USA* 86: 5257–5261 (1989)), (2) neuronal phosphatases STEP (Lombroso et al. *Proc. Natl. Acad. Sci. USA* 88: 7242–7246 (1991)), (3) PTP1C/SH-PTP1/SHP-1 (Plutzky et al. *Proc. Natl. Acad. Sci. USA* 89: 1123–1127 (1992)), (4) PTP1D/Syp/SH-PPT2/SHP-2 (Vogel et al. *Science* 259: 1611–1614 (1993); Feng et al. *Science* 259: 1607–1611 (1993)).

Receptor-type PTPases consist of a) a putative ligand-binding extracellular domain, b) a transmembrane segment, and c) an intracellular catalytic region. The structure and sizes of the putative ligand-binding extracellular domains of receptor-type PTPases are quite divergent. In contrast, the intracellular catalytic regions of receptor-type PTPases are very homologous to each other and to the intracellular PTPases. Most receptor-type PTPases have two tandemly duplicated catalytic PTPase domains. The first PTPases receptor subtypes identified were (1) CD45 (Ralph, S. J. *EMBO J.* 6: 1251–1257 (1987)) and (2) LAR (Streuli et al. *J. Exp. Med.* 168:1523–1530 (1988)). Since then many more receptor subtypes have been isolated and characterized, including PTPα, PTPβ, PTPδ, PTPε, PTPξ (Krueger, et al. *EMBO J.* 9: 3241–3252 (1990)).

Although agents have been identified for use as PTP1B inhibitors, such as those heteroaryl and aryl amino(oxo) acetic acids described in PCT Patent Publications WO 01/19831, WO 01/19830, and WO 01/17516, such agents do not exhibit separation of the inhibitory activity between PTP1B and TCPTP. Furthermore, because of the potential immunosuppressive effects resulting from inhibiting TCPTP, selective inhibition of PTP1B over TCPTP would make such agents more suitable for drug development as they could diminish or eliminate side effects derived from such nonselectivity.

Therefore, the development of PTP inhibitors which exhibit selectivity for the PTP1B receptor over other PTPases would minimize potential side effects otherwise resulting from the nonselective inhibition of other PTPases, thus making them more suitable for drug development. Accordingly, because of the important roles played by unregulated protein tyrosine phosphatase PTP1B in the disorder states of type I and II diabetes, obesity, autoimmune disorder, acute and chronic inflammation, osteoporosis and various forms of cancers, compounds which selectively inhibit this enzyme could provide the desired therapeutic benefits without the unwanted side effects derived from inhibiting other related phosphatases.

SUMMARY OF THE INVENTION

According to the present invention, PTP1B inhibitors which demonstrate selective inhibitory activity for PTP1B over other phosphatases are provided.

In particular, the present invention is directed to compounds of formula (I)

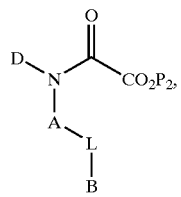

(I)

or a therapeutically acceptable salt or prodrug thereof, wherein

A is selected from the group consisting of

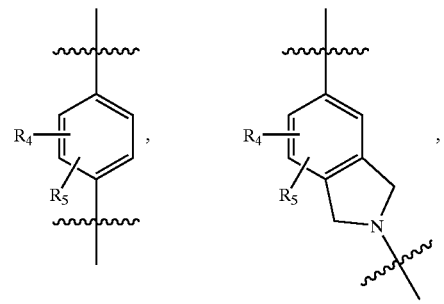

-continued

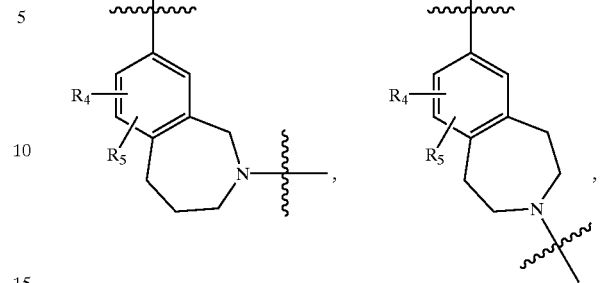

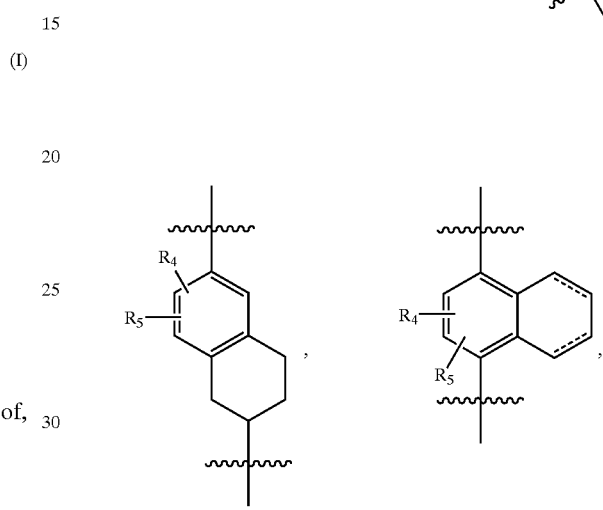

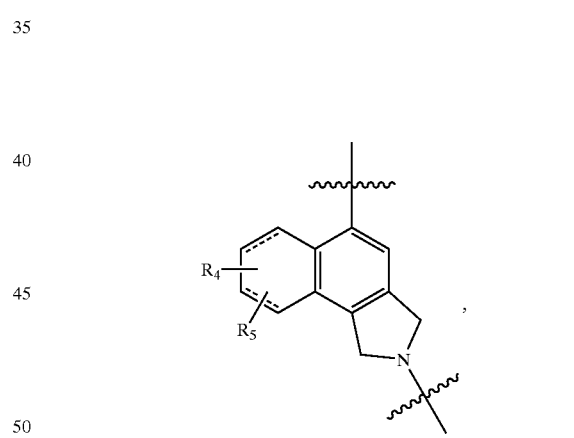

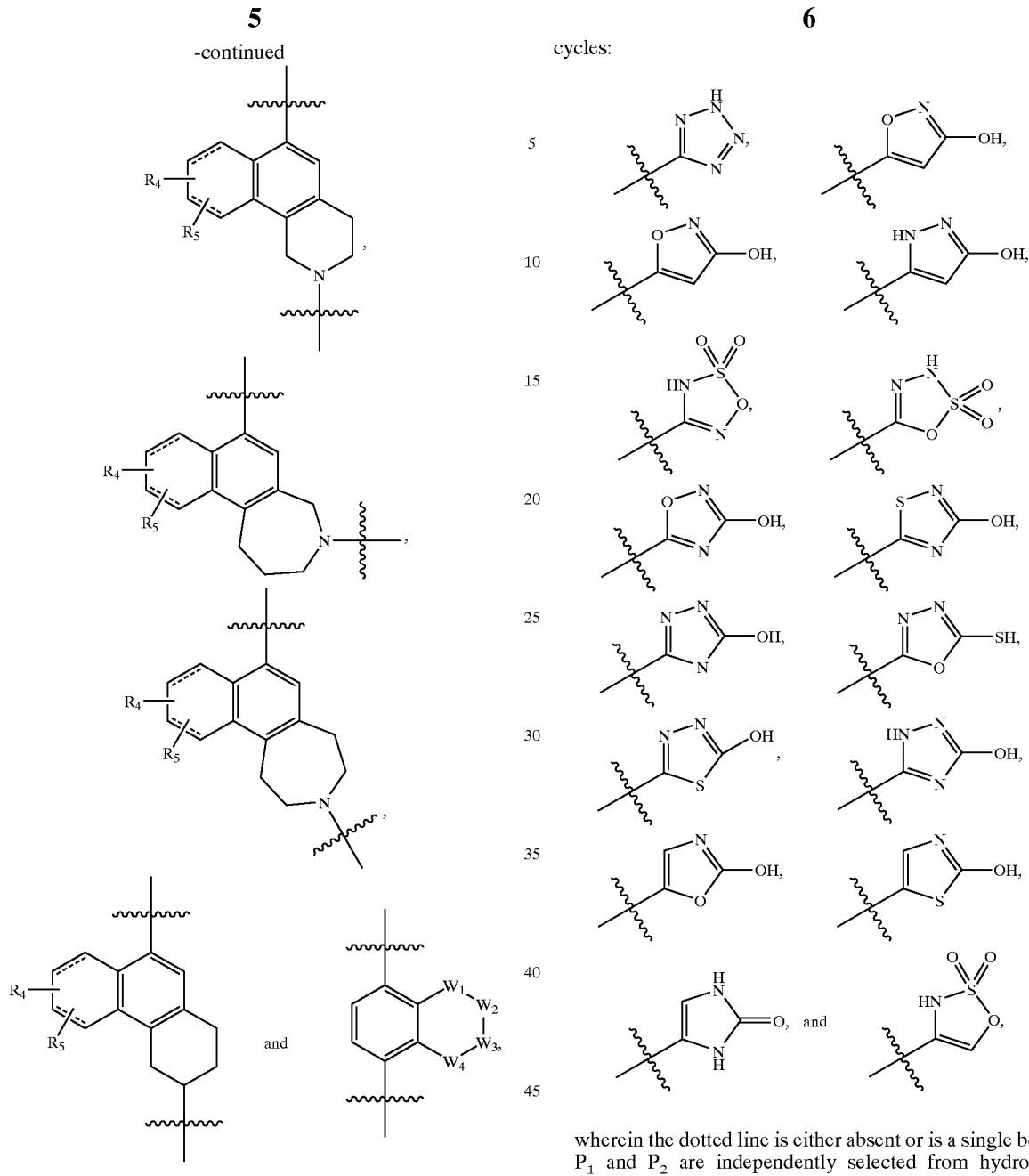

wherein the top is connected to the nitrogen and the bottom is connected to L, and the dotted line is either absent or is a single bond;

B is selected from the group consisting of hydrogen, alkyl, aryl, arylalkyl, heterocycle and heterocyclealkyl;

D is selected from the group consisting of

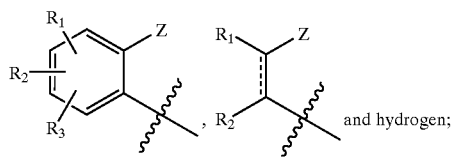

and hydrogen;

Z is selected from the group consisting of alkoxy, alkyl, amino, cyano, nitro, —$CO_2P_1$, —$SO_3H$, —$PO(OH)_2$, —$CH_2PO(OH)_2$, —$CHFPO(OH)_2$, —$CF_2(PO(OH)_2$, —C(=NH)$NH_2$, and the following 5-membered heterocycles:

wherein the dotted line is either absent or is a single bond;

$P_1$ and $P_2$ are independently selected from hydrogen, alkyl, alkenyl, arylalkyl, cycloalkyl and (cycloalkyl)alkyl;

$R_1$, $R_2$, $R_3$, $R_4$ and $R_5$ are independently selected from hydrogen, alkoxy, alkyl, aryl, arylalkyl, cyano, halo, haloalkoxy, haloalkyl, heterocycle, heterocyclealkyl, hydroxy, hydroxyalkyl, nitro, $NR_AR_B$, $NR_AR_BC(O)$, $NR_AR_BC(O)$alkyl and $NR_AR_BC(O)$alkenyl, wherein $R_A$ and $R_B$ are independently selected from hydrogen, alkyl, alkoxycarbonyl, alkylsulfonyl, aryl, arylalkylcarbonyl, arylcarbonyl, arylsulfonyl and ($R_CR_DN$)carbonyl wherein $R_C$ and $R_D$ are independently selected from hydrogen, alkyl, aryl, and arylalkyl, or $R_A$ and $R_B$ taken together with the nitrogen to which they are attached form a ring selected from the group consisting of pyrrolidine, piperidine, morpholine, homopiperidine and piperazine;

L is selected from the group consisting of
—$(CH_2)_mX_1(CH_2)_nCH(R_8)C(R_{9A})(R_{9B})X_2(CH_2)_pC(O)N(R_{10})CH(CO_2R_{11})(CH_2)_qX_3$—;
—$(CH_2)_mX_1(CH_2)_nCH(R_8)C(R_{9A})(R_{9B})X_2(CH_2)_pEC(O)N(R_{10})CH(CO_2R_{11})(CH_2)_qX_3$—;

—(CH$_2$)$_m$X$_1$(CH$_2$)$_n$CH(R$_8$)C(R$_{9A}$)(R$_{9B}$)X$_2$(CH$_2$)$_p$X$_3$—;
—(CH$_2$)$_m$X$_1$(CH$_2$)$_n$CH(R$_8$)C(R$_{9A}$)(R$_{9B}$)X$_2$(CH$_2$)$_p$X$_3$(CH$_2$)$_q$X$_4$—; and
—(CH$_2$)$_m$X$_1$(CH$_2$)$_n$CH(R$_8$)C(R$_{9A}$)(R$_{9B}$)X$_2$(CH$_2$)$_p$E(CH$_2$)$_q$X$_3$—, wherein each group is drawn with the left end attached to A and the right end attached to B;

m, n, p and q are independently between 0–4;

R$_8$ is selected from hydrogen, hydroxy, NR$_A$R$_B$ and (NR$_A$R$_B$)alkyl;

R$_{9A}$ and R$_{9B}$ are independently selected from hydrogen, alkyl, hydroxyalkyl and R$_E$R$_F$Nalkyl, wherein R$_E$ and R$_F$ are independently selected from hydrogen, alkyl, alkoxycarbonyl and alkanoyl, or R$_{9A}$ and R$_{9B}$ taken together are oxo;

R$_{10}$ is selected from hydrogen, alkyl, alkanoyl and alkoxycarbonyl;

R$_{11}$ is selected from hydrogen, alkyl, alkenyl, arylalkyl, cycloalkyl, and (cycloalkyl)alkyl;

E is selected from aryl and cycloalkyl;

X$_1$, X$_2$, X$_3$, and X$_4$ are independently absent or are independently selected from NR$_G$, O, S, S(O) and S(O)$_2$, wherein R$_G$ is selected from hydrogen, alkyl, alkanoyl and alkoxycarbonyl; and W$_1$, W$_2$, W$_3$ and W$_4$ are independently selected from CH, CH$_2$, N, NH and O.

According to another embodiment, the present invention is directed to a pharmaceutical composition comprising a therapeutically effective amount of a compound of formula (I) in combination with a pharmaceutically acceptable carrier.

According to another embodiment, the present invention is directed to method of selectively inhibiting protein tyrosine phosphatase 1B comprising administering a therapeutically effective amount of a compound of formula (I).

According to another embodiment, the present invention is directed to a method of treating disorders caused by overexpressed or altered protein tyrosine phosphatase 1B comprising administering a therapeutically effective amount of a compound of formula (I).

According to another embodiment, the present invention is directed to a method of treating type I and type II diabetes comprising administering a therapeutically effective amount of a compound of formula (I).

According to another embodiment, the present invention is directed to a method of treating obesity comprising administering a therapeutically effective amount of a compound of formula (I).

According to another embodiment, the present invention is directed to a method of treating autoimmune disorders, acute and chronic inflammatory disorders, osteoporosis, cancer, malignant disorders comprising administering a therapeutically effective amount of a compound of formula (I).

DETAILED DESCRIPTION OF THE INVENTION

Definitions

As used throughout the present specification, the following terms have the meanings indicated:

The term "alkenyl," as used herein, refers to a monovalent straight or branched chain hydrocarbon radical having from two to six carbons and at least one carbon-carbon double bond.

The term "alkoxy," as used herein, refers to an alkyl group attached to the parent molecular moiety through an oxygen atom.

The term "alkylcarbonyl," refers to an alkyl group attached to the parent molecule through a carbonyl group.

The term "alkoxycarbonyl," as used herein, refers to an alkoxy group attached to the parent molecular moiety through a carbonyl group.

The term "alkoxycarbonylalkenyl," as used herein, refers to an alkoxycarbonyl group attached to the parent molecular moiety through an alkenyl group.

The term "alkoxycarbonylalkyl," as used herein, refers to an alkoxycarbonyl group attached to the parent molecular moiety through an alkyl group.

The term "alkyl," as used herein, refers to a saturated, monovalent straight or branched chain hydrocarbon having from one to six carbons.

The term "alkylsufonyl," as used herein, refers to an alkyl group attached to the parent molecular moiety through a sulfonyl group.

The term "amino," as used herein, refers to a —NR$_A$R$_B$, wherein R$_A$ and R$_B$ are independently selected from hydrogen, alkylcarbonyl, alkenyl, alkoxycarbonyl, alkyl, alkylsulfonyl, aryl, arylalkyl, arylalkylcarbonyl, arylcarbonyl, arylsulfonyl, cycloalkyl, (cycloalkyl)alkyl, hydroxyalkyl, a nitrogen protecting group and R$_C$R$_D$Ncarbonyl, wherein R$_C$ and R$_D$ are independently selected from the group consisting of hydrogen, alkyl, aryl and arylalkyl; or R$_A$ and R$_B$ taken together with the nitrogen to which they are attached form a ring selected from the group consisting of pyrrolidine, piperidine, morpholine, homopiperidine and piperazine;

The term "aminoalkyl," as used herein, refers to an amino group attached to the parent molecular moiety through an alkyl group. The alkyl part of the aminoalkyl can be optionally substituted with one or two substituents independently selected from carboxy and alkoxycarbonyl;

The term "aminosulfonyl," as used herein, refers to an amino group attached to the parent molecular moiety through a sulfonyl group.

The term "aryl," as used herein, refers to a dihydronaphthyl, indanyl, indenyl, naphthyl, phenyl, and tetrahydronaphthyl. Aryl groups having an unsaturated or partially saturated ring fused to an aromatic ring can be attached through the saturated or the unsaturated part of the group. The aryl groups of the present invention can be optionally substituted with one, two, three, four, or five substituents independently selected from the group consisting of alkoxy, alkoxycarbonyl, alkyl, alkylsufonyl, amino, aminoalkenyl, aminoalkyl, aminosulfonyl, carboxy, carboxyalkenyl, carboxyalkyl, cyano, halo, haloalkyl, haloalkoxy, hydroxy, hydroxyalkyl, nitro, and thioalkoxy. The aryl groups of this invention can be further substituted with an additional aryl group, as defined herein, or an additional heterocycle, as defined herein, wherein the additional aryl group and the additional heterocycle can be substituted with 1, 2 or 3 substituents independently selected from of alkoxy, alkoxycarbonyl, alkyl, alkylsufonyl, amino, aminoalkenyl, aminoalkyl, aminosulfonyl, carboxy, carboxyalkenyl, carboxyalkyl, cyano, formyl, halo, haloalkyl, haloalkoxy, hydroxy, hydroxyalkyl, nitro, and thioalkoxy.

The term "arylalkyl," as used herein, refers to an aryl group attached to the parent molecular moiety through an alkyl group.

The term "arylalkylcarbonyl" as used herein, refers to an arylalkyl group attached to the parent molecular moiety through a carbonyl.

The term "arylcarbonyl," as used herein refers to an aryl group attached to the parent molecule through a carbonyl group.

The term "aryloxy," as used herein, refers to an aryl group attached to the parent molecular moiety through an oxygen atom.

The term "arylsulfonyl," as used herein refers to an aryl group attached to the parent molecule through a sulfonyl group.

The term "carbonyl," as used herein, refers to a —C(O)—.

The term "carboxy," as used herein, refers to a —$CO_2H$.

The term "carboxyalkyl," as used herein, refers to a carboxy group attached to the parent molecular moiety through an alkyl group.

The term "cyano," as used herein, refers to a —CN.

The term "cycloalkenyl," as used herein, refers to a monovalent cyclic or bicyclic hydrocarbon of four to twelve carbons having at least one carbon-carbon double bond.

The term "(cycloalkenyl)alkyl," as used herein, refers to a cycloalkenyl group attached to the parent molecular moiety through an alkyl group.

The term "cycloalkyl," as used herein, refers to a monovalent saturated cyclic or bicyclic hydrocarbon group of three to twelve carbons. The cycloalkyl groups of the invention can be optionally substituted with one, two, three, or four substituents independently selected from the group consisting of alkylcarbonyl, alkoxy, alkoxycarbonyl, alkyl, carboxy, halo and hydroxy.

The term "(cycloalkyl)alkyl," as used herein, refers to a cycloalkyl group attached to the parent molecular moiety through an alkyl group.

The term "formyl" refers to a —C(O)H group.

The term "halo," refers to an F, Cl, Br, or I.

The term "haloalkyl," refers to a halo group attached to the parent molecular moiety through an alkyl group.

The term "haloalkoxy" refers to a haloalkyl group attached to the parent molecule through an alkoxy group.

The term "heteroaryl," as used herein, refers to a cyclic, aromatic groups having five or six atoms, wherein at least one atom is selected from the group consisting of nitrogen, oxygen, and sulfur, and the remaining atoms are carbon. The five-membered rings have two double bonds, and the six-membered rings have three double bonds. Heteroaryls of the invention are exemplified by furanyl, thienyl, pyrrolyl, oxazolyl, thiazolyl, imidazolyl, isoxazolyl, isothiazolyl, oxadiazolyl, oxadiazolyl, triazolyl, thiadiazolyl, pyridyl, pyridazinyl, pyrimidinyl, pyrazinyl, pyrazolyl, triazinyl, and the like. The heteroaryl groups of the present invention are connected to the parent molecular group through a carbon atom in the ring or, as exemplified by imidazole, indole, and pyrazole, through either a carbon atom or nitrogen atom in the ring. The heteroaryl groups of the invention can also be fused to a second ring selected from the group consisting of aryl, heteroaryl and heterocycloalkyl in which case the heteroaryl group can be connected to the parent molecular group through either the aryl part, the heteroaryl part or the heterocycloalkyl part of the fused ring system. Heteroaryl groups of this type are exemplified by quinolinyl, isoquinolinyl, benzofuranyl, benzothiophenyl, benzoisoxazolyl, benzthiazolyl, benzooxazolyl, indolyl, thienopyrazinyl, thienylfuranyl, thienylpyridinyl, 2,3-dihydrothienofuranyl, and the like. The heteroaryl groups of this invention can be optionally substituted with one, two, or three substituents independently selected from the group consisting of alkoxy, alkoxycarbonyl, alkyl, alkylsufonyl, amino, aminoalkenyl, aminoalkyl, aminosulfonyl, carboxy, carboxyalkenyl, carboxyalkyl, cyano, halo, haloalkyl, haloalkoxy, hydroxy, hydroxyalkyl, nitro, and thioalkoxy.

The term "heteroarylalkyl," as used herein, refers to a heteroaryl group attached to the parent molecular moiety through an alkyl group.

The term "heterocycloalkyl," as used herein, refers to a cyclic, non-aromatic, four, five, or six membered ring containing at least one atom selected from the group consisting of oxygen, nitrogen, and sulfur. The four-membered rings have zero double bonds, the five-membered rings have zero or one double bonds, and the six-membered rings have zero, one, or two double bonds. Heterocycloalkyl groups of the invention are exemplified by dihydropyridinyl, imidazolinyl, morpholinyl, piperazinyl, pyrrolidinyl, pyrazolidinyl, tetrahydropyridinyl, piperidinyl, thiomorpholinyl, 1,3-dioxolanyl, 1,4-dioxanyl, 1,3-dioxanyl, and the like. The heterocycloalkyls of the present invention can be attached to the parent molecular group through a carbon atom or nitrogen atom in the ring. The heterocycloalkyl groups of the invention can also be fused to a aryl ring, in which case the heterocycloalkyl group can be connected to the parent molecular group through either the heterocycloalkyl part or the aryl part of the fused ring system. Heterocycloalkyl groups of this type are exemplified by benzodioxolyl, indolinyl, tetrahydroquinolinyl, chromanyl, and the like. The heterocycloalkyl groups of this invention can be optionally substituted one, two, three, four or five substituents independently selected from the group consisting of alkoxy, alkoxycarbonyl, alkyl, alkylsufonyl, amino, aminoalkenyl, aminoalkyl, aminosulfonyl, carboxy, carboxyalkenyl, carboxyalkyl, cyano, halo, haloalkyl, haloalkoxy, hydroxy, hydroxyalkyl, nitro, and thioalkoxy.

The term "(heterocycloalkyl)alkyl," as used herein, refers to a heterocycloalkyl group attached to the parent molecular moiety through an alkyl group.

The term "hydroxy," as used herein, refers to an —OH.

The term "hydroxyalkyl," as used herein, refers to a hydroxy group attached the parent molecular moiety through an alkyl group.

The term "inhibitor" as used herein, refers to a compound which prevents the binding of PTP1B to its endogenous substrates or prevents the dephosphorylation mediated by PTP1B on its endogenous substrate, including but not limited to insulin receptor tyrosine kinase (IRTK), and the fragments of IRTK, and the unnatural substrates, such as p-nitrophenyl phosphate.

The term "nitro," as used herein, refers to a —$NO_2$.

The term "nitrogen protecting group," as used herein, refers to a selectively introducible and removable groups which protect amino groups against undesirable side reactions during synthetic procedures. Examples of amino protecting groups include methoxycarbonyl, ethoxycarbonyl, trichloroethoxycarbonyl, benzyloxycarbonyl (Cbz), chloroacetyl, trifluoroacetyl, phenylacetyl, formyl, acetyl, benzoyl, tert-butoxycarbonyl (Boc), para-methoxybenzyloxycarbonyl, isopropoxycarbonyl, phthaloyl, succinyl, benzyl, diphenylmethyl, triphenylmethyl (trityl), methylsulfonyl, phenylsulfonyl, para-toluenesulfonyl, trimethylsilyl, triethylsilyl, triphenylsilyl, and the like.

The term "oxo," as used herein, refers to a =O.

The term "perfluoroalkoxy," as used herein, refers to a perfluoroalkyl group attached to the parent molecular moiety through an oxygen atom.

The term "perfluoralkyl," as used herein, refers to an alkyl group in which all of the hydrogen atoms have been replaced with fluoride atoms.

The term "phenyl," as used herein, refers to a 6 membered aromatic ring that is unsubstituted.

The term "selective," as used herein, refers to a compound having at least 3 fold greater affinity in terms of $K_{ic}$ value for the PTP1B receptor compared with the $K_{ic}$ value of other receptors, including but not limited to, TC-PTP, SHP-2, LAR, CD45, PP2B and Cdc25c.

The term "sulfonyl," as used herein, refers to a —SO$_2$—.

The term "thioalkoxy," as used herein, refers to an alkyl group attached to the parent molecular moiety through a sulfur atom.

The present invention provides compounds which selectively inhibit protein tyrosine phosphatase (PTP1B). In particular, the compounds of the present invention are selective PTP1B inhibitors and therefore are useful for treating disorders caused by overexpressed or altered protein tyrosine phosphatase (PTP1B). These disorders include autoimmune disorders, acute and chronic inflammatory disorders, osteoporosis, obesity, cancer, malignant disorders, and type I and type II diabetes.

According to one embodiment, the present invention is directed to compounds of formula (II)

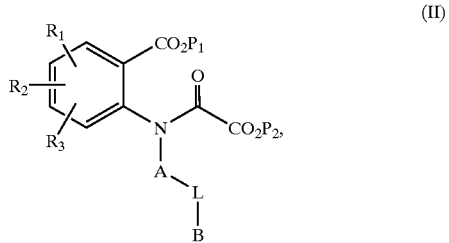

(II)

or therapeutically acceptable salt or prodrug thereof, wherein A, B, E, L, P$_1$, P$_2$, R$_1$, R$_2$, R$_3$, R$_4$, R$_5$, R$_8$, R$_{9A}$, R$_{9B}$, R$_{10}$, R$_{11}$, R$_A$, R$_B$, R$_C$, R$_D$, R$_E$, R$_F$, R$_G$, X$_1$, X$_2$, X$_3$, X$_4$, W$_1$, W$_2$, W$_3$, W$_4$, Z, m, n, o, p are as defined in formula (I).

In another embodiment, the present invention is directed to compounds of formula (II), or a therapeutically acceptable salt thereof, wherein A is selected from the group consisting of

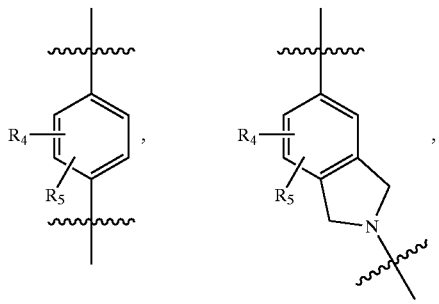

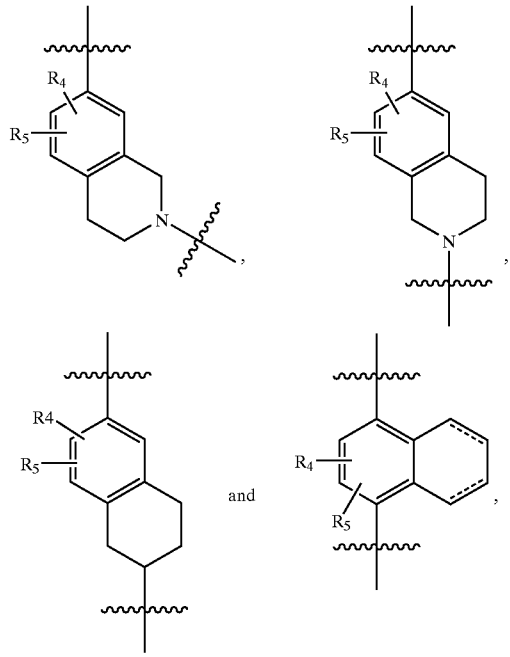

wherein the top is connected to the nitrogen and the bottom is connected to L, and
the dotted line is either absent or is a single bond;
R$_1$, R$_2$, R$_3$, R$_4$ and R$_5$ are selected from hydrogen, alkoxy, alkyl, cyano, halo, haloalkoxy, haloalkyl, heterocycle, hydroxy, hydroxyalkyl, nitro, NR$_A$R$_B$, NR$_A$R$_B$C(O), NR$_A$R$_B$C(O)alkyl and NR$_A$R$_B$C(O)alkenyl;
R$_{10}$ is selected from hydrogen and alkyl;
R$_{11}$ is selected from hydrogen, alkyl and arylalkyl; and
wherein B, E, L, P$_1$, P$_2$, R$_8$, R$_{9A}$, R$_{9B}$, R$_A$, R$_B$, R$_C$, R$_D$, R$_E$, R$_F$, R$_G$, X$_1$, X$_2$, X$_3$, X$_4$, W$_1$, W$_2$, W$_3$, W$_4$, Z, m, n, o, p are defined in formula (I).

In another embodiment, the present invention is directed to compounds of formula (II), wherein L is —(CH$_2$)$_m$X$_1$(CH$_2$)$_n$CH(R$_8$)C(R$_{9A}$)(R$_{9B}$)X$_2$(CH$_2$)$_p$C(O)N(R$_{10}$)CH(CO$_2$R$_{11}$)(CH$_2$)$_q$X$_3$—; and wherein A, B, E, P$_1$, P$_2$, R$_1$, R$_2$, R$_3$, R$_4$, R$_5$, R$_8$, R$_{9A}$, R$_{9B}$, R$_{10}$, R$_{11}$, R$_A$, R$_B$, R$_C$, R$_D$, R$_E$, R$_F$, R$_G$, X$_1$, X$_2$, X$_3$, X$_4$, W$_1$, W$_2$, W$_3$, W$_4$, Z, m, n, o, p are defined in formula (I).

In another embodiment, the present invention is directed to compounds of formula (II), wherein L is —(CH$_2$)$_m$X$_1$(CH$_2$)$_n$CH(R$_8$)C(R$_{9A}$)(R$_{9B}$)X$_2$(CH$_2$)$_p$C(O)N(R$_{10}$)CH(CO$_2$R$_{11}$)(CH$_2$)$_q$X$_3$—; R$_8$ is NR$_A$R$_B$; and wherein A, B, E, P$_1$, P$_2$, R$_1$, R$_2$, R$_3$, R$_4$, R$_5$, R$_{9A}$, R$_{9B}$, R$_{10}$, R$_{11}$, R$_A$, R$_B$, R$_C$, R$_D$, R$_E$, R$_F$, R$_G$, X$_1$, X$_2$, X$_3$, X$_4$, W$_1$, W$_2$, W$_3$, W$_4$, Z, m, n, o, p are defined in formula (I).

In another embodiment, the present invention is directed to compounds of formula (II), wherein L is —(CH$_2$)$_m$X$_1$(CH$_2$)$_n$CH(R$_8$)C(R$_{9A}$)(R$_{9B}$)X$_2$(CH$_2$)$_p$C(O)N(R$_{10}$)CH(CO$_2$R$_{11}$)(CH$_2$)$_q$X$_3$—; R$_8$ is NR$_A$R$_B$; R$_{9A}$ and R$_{9B}$ together are oxo; and wherein A, B, E, P$_1$, P$_2$, R$_1$, R$_2$, R$_3$, R$_4$, R$_5$, R$_{10}$, R$_{11}$, R$_A$, R$_B$, R$_C$, R$_D$, R$_E$, R$_F$, R$_G$, X$_1$, X$_2$, X$_3$, X$_4$, W$_1$, W$_2$, W$_3$, W$_4$, Z, m, n, o, p are defined in formula (I).

In another embodiment, the present invention is directed to compounds of formula (II), wherein L is —(CH$_2$)$_m$X$_1$(CH$_2$)$_n$CH(R$_8$)C(R$_{9A}$)(R$_{9B}$)X$_2$(CH$_2$)$_p$C(O)N(R$_{10}$)CH(CO$_2$R$_{11}$)(CH$_2$)$_q$X$_3$—; R$_8$ is NR$_A$R$_B$; R$_{9A}$ and R$_{9B}$ together are oxo; X$_2$ is NR$_C$; and wherein A, B, E, P$_1$, P$_2$, R$_1$, R$_2$, R$_3$, R$_4$, R$_5$, R$_{10}$, R$_{11}$, R$_A$, R$_B$, R$_C$, R$_D$, R$_E$, R$_F$, R$_G$, X$_1$, X$_3$, X$_4$, W$_1$, W$_2$, W$_3$, W$_4$, Z, m, n, o, p are defined in formula (I).

In another embodiment, the present invention is directed to compounds of formula (II), wherein L is —$(CH_2)_mX_1$$(CH_2)_nCH(R_8)C(R_{9A})(R_{9B}))X_2(CH_2)_pC(O)N(R_{10})CH(CO_2R_{11})(CH_2)_qX_3$—; $R_8$ is $NR_AR_B$; $R_{9A}$ and $R_{9B}$ together are oxo; $X_2$ is $NR_C$; B is selected from aryl and heterocycle; and wherein A, E, $P_1$, $P_2$, $R_1$, $R_2$, $R_3$, $R_4$, $R_5$, $R_{10}$, $R_{11}$, $R_A$, $R_B$, $R_C$, $R_D$, $R_E$, $R_F$, $R_G$, $X_1$, $X_3$, $X_4$, $W_1$, $W_2$, $W_3$, $W_4$, Z, m, n, o, p are defined in formula (I).

In another embodiment, the present invention is directed to compounds of formula (II), wherein L is —$(CH_2)_mX_1$$(CH_2)_nCH(R_8)C(R_{9A})(R_{9B})X_2(CH_2)_pC(O)N(R_{10})CH(CO_2R_{11})(CH_2)_qX_3$—; $R_8$ is $NR_AR_B$; $R_{9A}$ and $R_{9B}$ together are oxo; $X_2$ is $NR_C$; B is selected from aryl and heterocycle; A is

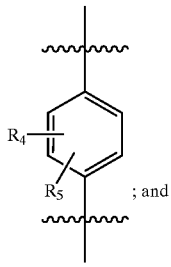

and wherein E, $P_1$, $P_2$, $R_1$, $R_2$, $R_3$, $R_4$, $R_5$, $R_{10}$, $R_{11}$, $R_A$, $R_B$, $R_C$, $R_D$, $R_E$, $R_F$, $R_G$, $X_1$, $X_3$, $X_4$, $W_1$, $W_2$, $W_3$, $W_4$, Z, m, n, o, p are defined in formula (I).

In another embodiment, the present invention is directed to compounds of formula (II), wherein L is —$(CH_2)_mX_1$$(CH_2)_nCH(R_8)C(R_{9A})(R_{9B}))X_2(CH_2)_pC(O)N(R_{10})CH(CO_2R_{11})(CH_2)_qX_3$—; $R_8$ is $NR_AR_B$; $R_{9A}$ and $R_{9B}$ together are oxo; $X_2$ is $NR_C$; B is hydrogen; and wherein A, E, $P_1$, $P_2$, $R_1$, $R_2$, $R_3$, $R_4$, $R_5$, $R_{10}$, $R_{11}$, $R_A$, $R_B$, $R_C$, $R_D$, $R_E$, $R_F$, $R_G$, $X_1$, $X_3$, $X_4$, $W_1$, $W_2$, $W_3$, $W_4$, Z, m, n, o, p are defined in formula (I).

In another embodiment, the present invention is directed to compounds of formula (II), wherein L is —$(CH_2)_mX_1$$(CH_2)_nCH(R_8)C(R_{9A})(R_{9B})X_2(CH_2)_pC(O)N(R_{10})CH(CO_2R_{11})(CH_2)_qX_3$—; $R_8$ is $NR_AR_B$; $R_{9A}$ and $R_{9B}$ together are oxo; $X_2$ is $NR_C$; B is hydrogen; A is

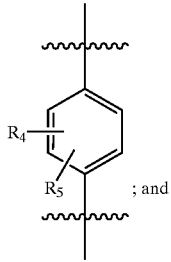

wherein E, $P_1$, $P_2$, $R_1$, $R_2$, $R_3$, $R_4$, $R_5$, $R_{10}$, $R_{11}$, $R_A$, $R_B$, $R_C$, $R_D$, $R_E$, $R_F$, $R_G$, $X_1$, $X_3$, $X_4$, $W_1$, $W_2$, $W_3$, $W_4$, Z, m, n, o, p are defined in formula (I).

In another embodiment, the present invention is directed to compounds of formula (II), wherein L is —$(CH_2)_mX_1$$(CH_2)_nCH(R_8)C(R_{9A})(R_{9B})X_2(CH_2)_pEC(O)N(R_{10})CH(CO_2R_{11})(CH_2)_qX_3$—; and wherein A, B, E, $P_1$, $P_2$, $R_1$, $R_2$, $R_3$, $R_4$, $R_5$, $R_8$, $R_{9A}$, $R_{9B}$, $R_{10}$, $R_{11}$, $R_A$, $R_B$, $R_C$, $R_D$, $R_E$, $R_F$, $R_G$, $X_1$, $X_2$, $X_3$, $X_4$, $W_1$, $W_2$, $W_3$, $W_4$, Z, m, n, o, p are defined in formula (I).

In another embodiment, the present invention is directed to compounds of formula (II), wherein L is —$(CH_2)_mX_1$$(CH_2)_nCH(R_8)C(R_{9A})(R_{9B})X_2(CH_2)_pEC(O)N(R_{10})CH(CO_2R_{11})(CH_2)_qX_3$—; $R_8$ is $NR_AR_B$; and wherein A, B, E, $P_1$, $P_2$, $R_1$, $R_2$, $R_3$, $R_4$, $R_5$, $R_{9A}$, $R_{9B}$, $R_{10}$, $R_{11}$, $R_A$, $R_B$, $R_C$, $R_D$, $R_E$, $R_F$, $R_G$, $X_1$, $X_2$, $X_3$, $X_4$, $W_1$, $W_2$, $W_3$, $W_4$, Z, m, n, o, p are defined in formula (I).

In another embodiment, the present invention is directed to compounds of formula (II), wherein L is —$(CH_2)_mX_1$$(CH_2)_nCH(R_8)C(R_{9A})(R_{9B})X_2(CH_2)_pEC(O)N(R_{10})CH(CO_2R_{11})(CH_2)_qX_3$—; $R_8$ is $NR_AR_B$; $R_{9A}$ and $R_{9B}$ together are oxo; and wherein A, B, E, $P_1$, $P_2$, $R_1$, $R_2$, $R_3$, $R_4$, $R_5$, $R_{10}$, $R_{11}$, $R_A$, $R_B$, $R_C$, $R_D$, $R_E$, $R_F$, $R_G$, $X_1$, $X_2$, $X_3$, $X_4$, $W_1$, $W_2$, $W_3$, $W_4$, Z, m, n, o, p are defined in formula (I).

In another embodiment, the present invention is directed to compounds of formula (II), wherein L is —$(CH_2)_mX_1$$(CH_2)_nCH(R_8)C(R_{9A})(R_{9B})X_2(CH_2)_pEC(O)N(R_{10})CH(CO_2R_{11})(CH_2)_qX_3$—; $R_8$ is $NR_AR_B$; $R_{9A}$ and $R_{9B}$ together are oxo; $X_2$ is $NR_C$; and wherein A, B, E, $P_1$, $P_2$, $R_1$, $R_2$, $R_3$, $R_4$, $R_5$, $R_{10}$, $R_{11}$, $R_A$, $R_B$, $R_C$, $R_D$, $R_E$, $R_F$, $R_G$, $X_1$, $X_3$, $X_4$, $W_1$, $W_2$, $W_3$, $W_4$, Z, m, n, o, p are defined in formula (I).

In another embodiment, the present invention is directed to compounds of formula (II), wherein L is —$(CH_2)_mX_1$$(CH_2)_nCH(R_8)C(R_{9A})(R_{9B})X_2(CH_2)_pEC(O)N(R_{10})CH(CO_2R_{11})(CH_2)_qX_3$—; $R_8$ is $NR_AR_B$; $R_{9A}$ and $R_{9B}$ together are oxo; $X_2$ is $NR_C$; B is hydrogen; and wherein A, E, $P_1$, $P_2$, $R_1$, $R_2$, $R_3$, $R_4$, $R_5$, $R_{10}$, $R_{11}$, $R_A$, $R_B$, $R_C$, $R_D$, $R_E$, $R_F$, $R_G$, $X_1$, $X_3$, $X_4$, $W_1$, $W_2$, $W_3$, $W_4$, Z, m, n, o, p are defined in formula (I).

In another embodiment, the present invention is directed to compounds of formula (II), wherein L is —$(CH_2)_mX_1$$(CH_2)_nCH(R_8)C(R_{9A})(R_{9B})X_2(CH_2)_pEC(O)N(R_{10})CH(CO_2R_{11})(CH_2)_qX_3$—; $R_8$ is $NR_AR_B$; $R_{9A}$ and $R_{9B}$ together are oxo; $X_2$ is $NR_C$; B is hydrogen; E is cycloalkyl; and wherein A, $P_1$, $P_2$, $R_1$, $R_2$, $R_3$, $R_4$, $R_5$, $R_{10}$, $R_{11}$, $R_A$, $R_B$, $R_C$, $R_D$, $R_E$, $R_F$, $R_G$, $X_1$, $X_3$, $X_4$, $W_1$, $W_2$, $W_3$, $W_4$, Z, m, n, o, p are defined in formula (I).

In another embodiment, the present invention is directed to compounds of formula (II), wherein L is —$(CH_2)_mX_1$$(CH_2)_nCH(R_8)C(R_{9A})(R_{9B})X_2(CH_2)_pEC(O)N(R_{10})CH(CO_2R_{11})(CH_2)_qX_3$—; $R_8$ is $NR_AR_B$; $R_{9A}$ and $R_{9B}$ together are oxo; $X_2$ is $NR_C$; B is hydrogen; E is cycloalkyl; A is

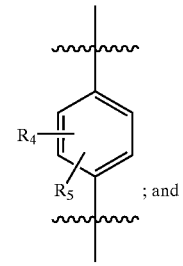

wherein $P_1$, $P_2$, $R_1$, $R_2$, $R_3$, $R_4$, $R_5$, $R_{10}$, $R_{11}$, $R_A$, $R_B$, $R_C$, $R_D$, $R_E$, $R_F$, $R_G$, $X_1$, $X_3$, $X_4$, $W_1$, $W_2$, $W_3$, $W_4$, Z, m, n, o, p are defined in formula (I).

In another embodiment, the present invention is directed to compounds of formula (II), wherein L is —$(CH_2)_mX_1$$(CH_2)_nCH(R_8)C(R_{9A})(R_{9B}))X_2(CH_2)_pC(O)N(R_{10})CH(CO_2R_{11})(CH_2)_qX_3$—; $R_8$ is $NR_AR_B$; $R_{9A}$ and $R_{9B}$ together are oxo; $X_2$ is $NR_C$; $X_3$ is S; B is alkyl; wherein A, E, $P_1$, $P_2$, $R_1$, $R_2$, $R_3$, $R_4$, $R_5$, $R_{10}$, $R_{11}$, $R_A$, $R_B$, $R_C$, $R_D$, $R_E$, $R_F$, $R_G$, $X_1$, $X_4$, $W_1$, $W_2$, $W_3$, $W_4$, Z, m, n, o, p are defined in formula (I).

In another embodiment, the present invention is directed to compounds of formula (II), wherein L is —$(CH_2)_mX_1$$(CH_2)_nCH(R_8)C(R_{9A})(R_{9B}))X_2(CH_2)_pC(O)N(R_{10})CH$ ($CO_2R_{11}$)($CH_2$)$_q$$X_3$—; $R_8$ is $NR_AR_B$; $R_{9A}$ and $R_{9B}$ together are oxo; $X_2$ is $NR_C$; $X_3$ is S; B is alkyl; A is

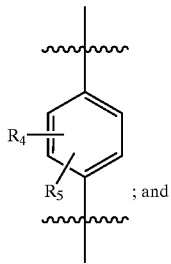

; and wherein E, $P_1$, $P_2$, $R_1$, $R_2$, $R_3$, $R_4$, $R_5$, $R_{10}$, $R_{11}$, $R_A$, $R_B$, $R_C$, $R_D$, $R_E$, $R_F$, $R_G$, $X_1$, $X_4$, $W_1$, $W_2$, $W_3$, $W_4$, Z, m, n, o, p are defined in formula (I).

In another embodiment, the present invention is directed to compounds of formula (II), wherein L is —($CH_2$)$_m$$X_1$($CH_2$)$_n$CH($R_8$)C($R_{9A}$)($R_{9B}$))$X_2$($CH_2$)$_p$C(O)N($R_{10}$)CH($CO_2R_{11}$)($CH_2$)$_q$$X_3$—; $R_8$ is $NR_AR_B$; $R_{9A}$ and $R_{9B}$ together are oxo; $X_2$ is $NR_C$; $X_3$ is S; B is alkyl; and wherein A, E, $P_1$, $P_2$, $R_1$, $R_2$, $R_3$, $R_4$, $R_5$, $R_{10}$, $R_{11}$, $R_A$, $R_B$, $R_C$, $R_D$, $R_E$, $R_F$, $R_G$, $X_1$, $X_4$, $W_1$, $W_2$, $W_3$, $W_4$, Z, m, n, o, p are defined in formula (I).

In another embodiment, the present invention is directed to compounds of formula (II), wherein L is —($CH_2$)$_m$$X_1$($CH_2$)$_n$CH($R_8$)C($R_{9A}$)($R_{9B}$))$X_2$($CH_2$)$_p$C(O)N($R_{10}$)CH($CO_2R_{11}$)($CH_2$)$_q$$X_3$—; $R_8$ is $NR_AR_B$; $R_{9A}$ and $R_{9B}$ together are oxo; $X_2$ is $NR_C$; $X_3$ is S; B is alkyl; is

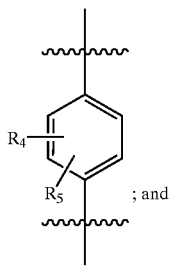

; and wherein E, L, $P_1$, $P_2$, $R_1$, $R_2$, $R_3$, $R_4$, $R_5$, $R_{10}$, $R_{11}$, $R_A$, $R_B$, $R_C$, $R_D$, $R_E$, $R_F$, $R_G$, $X_1$, $X_4$, $W_1$, $W_2$, $W_3$, $W_4$, Z, m, n, o, p are defined in formula (I).

In another embodiment, the present invention is directed to compounds of formula (II), wherein L is —($CH_2$)$_m$$X_1$($CH_2$)$_n$CH($R_8$)C($R_{9A}$)($R_{9B}$))$X_2$($CH_2$)$_p$C(O)N($R_{10}$)CH($CO_2R_{11}$)($CH_2$)$_q$$X_3$—; $R_8$ is $NR_AR_B$; $R_{9A}$ and $R_{9B}$ together are oxo; $X_2$ is $NR_C$; $X_3$ is S; B is alkyl; A is

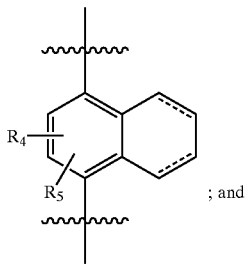

; and wherein E, L, $P_1$, $P_2$, $R_1$, $R_2$, $R_3$, $R_4$, $R_5$, $R_{10}$, $R_{11}$, $R_A$, $R_B$, $R_C$, $R_D$, $R_E$, $R_F$, $R_G$, $X_1$, $X_4$, $W_1$, $W_2$, $W_3$, $W_4$, Z, m, n, o, p are defined in formula (I).

In another embodiment, the present invention is directed to compounds of formula (II), wherein L is —($CH_2$)$_m$$X_1$($CH_2$)$_n$CH($R_8$)C($R_{9A}$)($R_{9B}$)$X_2$($CH_2$)$_p$$X_3$—; and wherein A, B, E, $P_1$, $P_2$, $R_1$, $R_2$, $R_3$, $R_4$, $R_5$, $R_8$, $R_{9A}$, $R_{9B}$, $R_{10}$, $R_{11}$, $R_A$, $R_B$, $R_C$, $R_D$, $R_E$, $R_F$, $R_G$, $X_1$, $X_2$, $X_3$, $X_4$, $W_1$, $W_2$, $W_3$, $W_4$, Z, m, n, o, p are defined in formula (I).

In another embodiment, the present invention is directed to compounds of formula (II), wherein L is —($CH_2$)$_m$$X_1$($CH_2$)$_n$CH($R_8$)C($R_{9A}$)($R_{9B}$)$X_2$($CH_2$)$_p$$X_3$—; $R_8$ is $NR_AR_B$; and wherein A, B, E, $P_1$, $P_2$, $R_1$, $R_2$, $R_3$, $R_4$, $R_5$, $R_{9A}$, $R_{9B}$, $R_{10}$, $R_{11}$, $R_A$, $R_B$, $R_C$, $R_D$, $R_E$, $R_F$, $R_G$, $X_1$, $X_2$, $X_3$, $X_4$, $W_1$, $W_2$, $W_3$, $W_4$, Z, m, n, o, p are defined in formula (I).

In another embodiment, the present invention is directed to compounds of formula (II), wherein L is —($CH_2$)$_m$$X_1$($CH_2$)$_n$CH($R_8$)C($R_{9A}$)($R_{9B}$)$X_2$($CH_2$)$_p$$X_3$—; $R_8$ is $NR_AR_B$; $R_{9A}$ and $R_{9B}$ together are oxo; and wherein A, B, E, $P_1$, $P_2$, $R_1$, $R_2$, $R_3$, $R_4$, $R_5$, $R_{10}$, $R_{11}$, $R_A$, $R_B$, $R_C$, $R_D$, $R_E$, $R_F$, $R_G$, $X_1$, $X_2$, $X_3$, $X_4$, $W_1$, $W_2$, $W_3$, $W_4$, Z, m, n, o, p are defined in formula (I).

In another embodiment, the present invention is directed to compounds of formula (II), wherein L is —($CH_2$)$_m$$X_1$($CH_2$)$_n$CH($R_8$)C($R_{9A}$)($R_{9B}$)$X_2$($CH_2$)$_p$$X_3$—; $R_8$ is $NR_AR_B$; $R_{9A}$ and $R_{9B}$ together are oxo; $X_2$ is $NR_C$; and wherein A, B, E, $P_1$, $P_2$, $R_1$, $R_2$, $R_3$, $R_4$, $R_5$, $R_{10}$, $R_{11}$, $R_A$, $R_B$, $R_C$, $R_D$, $R_E$, $R_F$, $R_G$, $X_1$, $X_3$, $X_4$, $W_1$, $W_2$, $W_3$, $W_4$, Z, m, n, o, p are defined in formula (I).

In another embodiment, the present invention is directed to compounds of formula (II), wherein L is —($CH_2$)$_m$$X_1$($CH_2$)$_n$CH($R_8$)C($R_{9A}$)($R_{9B}$)$X_2$($CH_2$)$_p$$X_3$—; $R_8$ is $NR_AR_B$; $R_{9A}$ and $R_{9B}$ together are oxo; $X_2$ is $NR_C$; $X_3$ is O; and wherein A, B, E, $P_1$, $P_2$, $R_1$, $R_2$, $R_3$, $R_4$, $R_5$, $R_{10}$, $R_{11}$, $R_A$, $R_B$, $R_C$, $R_D$, $R_E$, $R_F$, $R_G$, $X_1$, $X_4$, $W_1$, $W_2$, $W_3$, $W_4$, Z, m, n, o, p are defined in formula (I).

In another embodiment, the present invention is directed to compounds of formula (II), wherein L is —($CH_2$)$_m$$X_1$($CH_2$)$_n$CH($R_8$)C($R_{9A}$)($R_{9B}$)$X_2$($CH_2$)$_p$$X_3$—; $R_8$ is $NR_AR_B$; $R_{9A}$ and $R_{9B}$ together are oxo; $X_2$ is $NR_C$; $X_3$ is O; B is aryl; and wherein A, E, $P_1$, $P_2$, $R_1$, $R_2$, $R_3$, $R_4$, $R_5$, $R_{10}$, $R_{11}$, $R_A$, $R_B$, $R_C$, $R_D$, $R_E$, $R_F$, $R_G$, $X_1$, $X_4$, $W_1$, $W_2$, $W_3$, $W_4$, Z, m, n, o, p are defined in formula (I).

In another embodiment, the present invention is directed to compounds of formula (II), wherein L is —($CH_2$)$_m$$X_1$($CH_2$)$_n$CH($R_8$)C($R_{9A}$)($R_{9B}$)$X_2$($CH_2$)$_p$$X_3$—; $R_8$ is $NR_AR_B$; $R_{9A}$ and $R_{9B}$ together are oxo; $X_2$ is $NR_C$; $X_3$ is O; B is aryl; A is

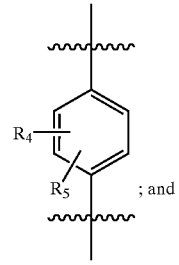

; and wherein E, $P_1$, $P_2$, $R_1$, $R_2$, $R_3$, $R_4$, $R_5$, $R_{10}$, $R_{11}$, $R_A$, $R_B$, $R_C$, $R_D$, $R_E$, $R_F$, $R_G$, $X_1$, $X_4$, $W_1$, $W_2$, $W_3$, $W_4$, Z, m, n, o, p are defined in formula (I).

In another embodiment, the present invention is directed to compounds of formula (II), wherein L is —($CH_2$)$_m$$X_1$($CH_2$)$_n$CH($R_8$)C($R_{9A}$)($R_{9B}$)$X_2$($CH_2$)$_p$$X_3$—; $R_8$ is $NR_AR_B$; $R_{9A}$ and $R_{9B}$ together are oxo; $X_2$ is $NR_C$; $X_3$ is O; B is aryl; A is

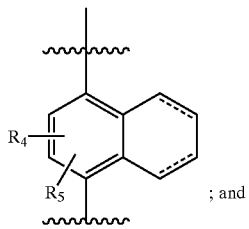
; and wherein E, $P_1$, $P_2$, $R_1$, $R_2$, $R_3$, $R_4$, $R_5$, $R_{10}$, $R_{11}$, $R_A$, $R_B$, $R_C$, $R_D$, $R_E$, $R_F$, $R_G$, $X_3$, $X_4$, $W_1$, $W_2$, $W_3$, $W_4$, Z, m, n, o, p are defined in formula (I).

In another embodiment, the present invention is directed to compounds of formula (II), wherein L is —$(CH_2)_m X_1 (CH_2)_n CH(R_8)C(R_{9A})(R_{9B})X_2(CH_2)_p X_3$—; $R_8$ is hydrogen; and wherein A, B, E, $P_1$, $P_2$, $R_1$, $R_2$, $R_3$, $R_4$, $R_5$, $R_{9A}$, $R_{9B}$, $R_{10}$, $R_{11}$, $R_A$, $R_B$, $R_C$, $R_D$, $R_E$, $R_F$, $R_G$, $X_1$, $X_2$, $X_3$, $X_4$, $W_1$, $W_2$, $W_3$, $W_4$, Z, m, n, o, p are defined in formula (I).

In another embodiment, the present invention is directed to compounds of formula (II), wherein L is —$(CH_2)_m X_1 (CH_2)_n CH(R_8)C(R_{9A})(R_{9B})X_2(CH_2)_p X_3$—; $R_8$ is hydrogen; $R_{9A}$ and $R_{9B}$ together are oxo; and wherein A, B, E, $P_1$, $P_2$, $R_1$, $R_2$, $R_3$, $R_4$, $R_5$, $R_{10}$, $R_{11}$, $R_A$, $R_B$, $R_C$, $R_D$, $R_E$, $R_F$, $R_G$, $X_1$, $X_2$, $X_3$, $X_4$, $W_1$, $W_2$, $W_3$, $W_4$, Z, m, n, o, p are defined in formula (I).

In another embodiment, the present invention is directed to compounds of formula (II), wherein L is —$(CH_2)_m X_1 (CH_2)_n CH(R_8)C(R_{9A})(R_{9B})X_2(CH_2)_p X_3$—; $R_8$ is hydrogen; $R_{9A}$ and $R_{9B}$ together are oxo; $X_2$ is $NR_C$; and wherein A, B, E, $P_1$, $P_2$, $R_1$, $R_2$, $R_3$, $R_4$, $R_5$, $R_{10}$, $R_{11}$, $R_A$, $R_B$, $R_C$, $R_D$, $R_E$, $R_F$, $R_G$, $X_1$, $X_3$, $X_4$, $W_1$, $W_2$, $W_3$, $W_4$, Z, m, n, o, p are defined in formula (I).

In another embodiment, the present invention is directed to compounds of formula (II), wherein L is —$(CH_2)_m X_1 (CH_2)_n CH(R_8)C(R_{9A})(R_{9B})X_2(CH_2)_p X_3$—; $R_8$ is hydrogen; $R_{9A}$ and $R_{9B}$ together are oxo; $X_2$ is $NR_C$; $X_3$ is O; and wherein A, B, E, $P_1$, $P_2$, $R_1$, $R_2$, $R_3$, $R_4$, $R_5$, $R_{10}$, $R_{11}$, $R_A$, $R_B$, $R_C$, $R_D$, $R_E$, $R_F$, $R_G$, $X_1$, $X_4$, $W_1$, $W_2$, $W_3$, $W_4$, Z, m, n, o, p are defined in formula (I).

In another embodiment, the present invention is directed to compounds of formula (II), wherein L is —$(CH_2)_m X_1 (CH_2)_n CH(R_8)C(R_{9A})(R_{9B})X_2(CH_2)_p X_3$—; $R_8$ is hydrogen; $R_{9A}$ and $R_{9B}$ together are oxo; $X_2$ is $NR_C$; $X_3$ is O; B is aryl; and wherein A, E, $P_1$, $P_2$, $R_1$, $R_2$, $R_3$, $R_4$, $R_5$, $R_{10}$, $R_{11}$, $R_A$, $R_B$, $R_C$, $R_D$, $R_E$, $R_F$, $R_G$, $X_1$, $X_4$, $W_1$, $W_2$, $W_3$, $W_4$, Z, m, n, o, p are defined in formula (I).

In another embodiment, the present invention is directed to compounds of formula (II), wherein L is —$(CH_2)_m X_1 (CH_2)_n CH(R_8)C(R_{9A})(R_{9B})X_2(CH_2)_p X_3$—; $R_8$ is hydrogen; $R_{9A}$ and $R_{9B}$ together are oxo; $X_2$ is $NR_C$; $X_3$ is O; B is aryl; A is

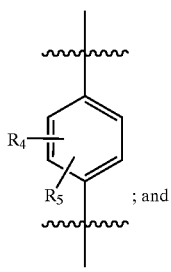
; and wherein E, $P_1$, $P_2$, $R_1$, $R_2$, $R_3$, $R_4$, $R_5$, $R_{10}$, $R_{11}$, $R_A$, $R_B$, $R_C$, $R_D$, $R_E$, $R_F$, $R_G$, $X_1$, $X_4$, $W_1$, $W_2$, $W_3$, $W_4$, Z, m, n, o, p are defined in formula (I).

In another embodiment, the present invention is directed to compounds of formula (II), wherein L is —$(CH_2)_m X_1 (CH_2)_n CH(R_8)C(R_{9A})(R_{9B})X_2(CH_2)_p X_3$—; $R_8$ is hydrogen; $R_{9A}$ and $R_{9B}$ together are oxo; $X_2$ is $NR_C$; $X_3$ is O; B is aryl; A is

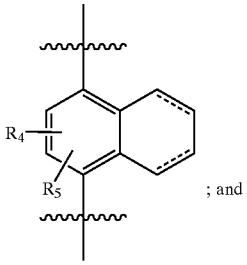
; and wherein E, $P_1$, $P_2$, $R_1$, $R_2$, $R_3$, $R_4$, $R_5$, $R_{10}$, $R_{11}$, $R_A$, $R_B$, $R_C$, $R_D$, $R_E$, $R_F$, $R_G$, $X_1$, $X_4$, $W_1$, $W_2$, $W_3$, $W_4$, Z, m, n, o, p are defined in formula (I).

In another embodiment, the present invention is directed to compounds of formula (II), wherein L is —$(CH_2)_m X_1 (CH_2)_n CH(R_8)C(R_{9A})(R_{9B})X_2(CH_2)_p X_3$—; $R_8$ is hydrogen; $R_{9A}$ is alkyl; and wherein A, B, E, $P_1$, $P_2$, $R_1$, $R_2$, $R_3$, $R_4$, $R_5$, $R_{9B}$, $R_{10}$, $R_{11}$, $R_A$, $R_B$, $R_C$, $R_D$, $R_E$, $R_F$, $R_G$, $X_1$, $X_2$, $X_3$, $X_4$, $W_1$, $W_2$, $W_3$, $W_4$, Z, m, n, o, p are defined in formula (I).

In another embodiment, the present invention is directed to compounds of formula (II), wherein L is —$(CH_2)_m X_1 (CH_2)_n CH(R_8)C(R_{9A})(R_{9B})X_2(CH_2)_p X_3$—; $R_8$ is hydrogen; $R_{9A}$ is alkyl; $X_2$ is $NR_C$; and wherein A, B, E, $P_1$, $P_2$, $R_1$, $R_2$, $R_3$, $R_4$, $R_5$, $R_{9B}$, $R_{10}$, $R_{11}$, $R_A$, $R_B$, $R_C$, $R_D$, $R_E$, $R_F$, $R_G$, $X_1$, $X_3$, $X_4$, $W_1$, $W_2$, $W_3$, $W_4$, Z, m, n, o, p are defined in formula (I).

In another embodiment, the present invention is directed to compounds of formula (II), wherein L is —$(CH_2)_m X_1 (CH_2)_n CH(R_8)C(R_{9A})(R_{9B})X_2(CH_2)_p X_3$—; $R_8$ is hydrogen; $R_{9A}$ is alkyl; $X_2$ is $NR_C$; $X_3$ is O; and wherein A, B, E, $P_1$, $P_2$, $R_1$, $R_2$, $R_3$, $R_4$, $R_5$, $R_{9B}$, $R_{10}$, $R_{11}$, $R_A$, $R_B$, $R_C$, $R_D$, $R_E$, $R_F$, $R_G$, $X_1$, $X_4$, $W_1$, $W_2$, $W_3$, $W_4$, Z, m, n, o, p are defined in formula (I).

In another embodiment, the present invention is directed to compounds of formula (II), wherein L is —$(CH_2)_m X_1 (CH_2)_n CH(R_8)C(R_{9A})(R_{9B})X_2(CH_2)_p X_3$—; $R_8$ is hydrogen; $R_{9A}$ is alkyl; $X_2$ is $NR_C$; $X_3$ is O; B is aryl; and wherein A, E, $P_1$, $P_2$, $R_1$, $R_2$, $R_3$, $R_4$, $R_5$, $R_{9B}$, $R_{10}$, $R_{11}$, $R_A$, $R_B$, $R_C$, $R_D$, $R_E$, $R_F$, $R_G$, $X_1$, $X_4$, $W_1$, $W_2$, $W_3$, $W_4$, Z, m, n, o, p are defined in formula (I).

In another embodiment, the present invention is directed to compounds of formula (II), wherein L is —$(CH_2)_m X_1 (CH_2)_n CH(R_8)C(R_{9A})(R_{9B})X_2(CH_2)_p X_3$—; $R_8$ is hydrogen; $R_{9A}$ is alkyl; $X_2$ is $NR_C$; $X_3$ is O; B is aryl; A is

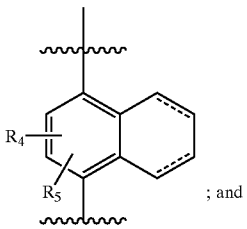
; and wherein E, $P_1$, $P_2$, $R_1$, $R_2$, $R_3$, $R_4$, $R_5$, $R_{9B}$, $R_{10}$, $R_{11}$, $R_A$, $R_B$, $R_C$, $R_D$, $R_E$, $R_F$, $R_G$, $X_1$, $X_4$, $W_1$, $W_2$, $W_3$, $W_4$, Z, m, n, o, p are defined in formula (I).

In another embodiment, the present invention is directed to compounds of formula (II), wherein L is —$(CH_2)_m X_1$ $(CH_2)_nCH(R_8)C(R_{9A})(R_{9B})X_2(CH_2)_pX_3$—; $R_8$ is hydrogen; $R_{9A}$ and $R_{9B}$ are both hydrogen; and wherein A, B, E, $P_1$, $P_2$, $R_1$, $R_2$, $R_3$, $R_4$, $R_5$, $R_{9B}$, $R_{10}$, $R_{11}$, $R_A$, $R_B$, $R_C$, $R_D$, $R_E$, $R_F$, $R_G$, $X_1$, $X_2$, $X_3$, $X_4$, $W_1$, $W_2$, $W_3$, $W_4$, Z, m, n, o, p are defined in formula (I).

In another embodiment, the present invention is directed to compounds of formula (II), wherein L is —$(CH_2)_mX_1$ $(CH_2)_nCH(R_8)C(R_{9A})(R_{9B})X_2(CH_2)_pX_3$—; $R_8$ is hydrogen; $R_{9A}$ and $R_{9B}$ are both hydrogen; $X_2NR_C$; and wherein A, B, E, $P_1$, $P_2$, $R_1$, $R_2$, $R_3$, $R_4$, $R_5$, $R_{10}$, $R_{11}$, $R_A$, $R_B$, $R_C$, $R_D$, $R_E$, $R_F$, $R_G$, $X_1$, $X_3$, $X_4$, $W_1$, $W_2$, $W_3$, $W_4$, Z, m, n, o, p are defined in formula (I).

In another embodiment, the present invention is directed to compounds of formula (II), wherein L is —$(CH_2)_mX_1$ $(CH_2)_nCH(R_8)C(R_{9A})(R_{9B})X_2(CH_2)_pX_3$—; $R_8$ is hydrogen; $R_{9A}$ and $R_{9B}$ are both hydrogen; $X_2$ is $NR_C$; $X_3$ is O; and wherein A, B, E, $P_1$, $P_2$, $R_1$, $R_2$, $R_3$, $R_4$, $R_5$, $R_{10}$, $R_{11}$, $R_A$, $R_B$, $R_C$, $R_D$, $R_E$, $R_F$, $R_G$, $X_1$, $X_4$, $W_1$, $W_2$, $W_3$, $W_4$, Z, m, n, o, p are defined in formula (I).

In another embodiment, the present invention is directed to compounds of formula (II), wherein L is —$(CH_2)_mX_1$ $(CH_2)_nCH(R_8)C(R_{9A})(R_{9B})X_2(CH_2)_pX_3$—; $R_8$ is hydrogen; $R_{9A}$ and $R_{9B}$ are both hydrogen; $X_2$ is $NR_C$; $X_3$ is O; B is aryl; and wherein A, E, $P_1$, $P_2$, $R_1$, $R_2$, $R_3$, $R_4$, $R_5$, $R_{10}$, $R_{11}$, $R_A$, $R_B$, $R_C$, $R_D$, $R_E$, $R_F$, $R_G$, $X_1$, $X_4$, $W_1$, $W_2$, $W_3$, $W_4$, Z, m, n, o, p are defined in formula (I).

In another embodiment, the present invention is directed to compounds of formula (II), wherein L is —$(CH_2)_mX_1$ $(CH_2)_nCH(R_8)C(R_{9A})(R_{9B})X_2(CH_2)_pX_3$—; $R_8$ is hydrogen; $R_{9A}$ and $R_{9B}$ are both hydrogen; $X_2$ is $NR_C$; $X_3$ is O; B is aryl; A is

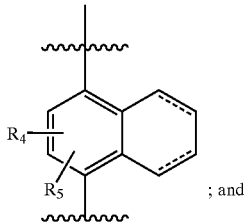

; and wherein E, $P_1$, $P_2$, $R_1$, $R_2$, $R_3$, $R_4$, $R_5$, $R_{10}$, $R_{11}$, $R_A$, $R_B$, $R_C$, $R_D$, $R_E$, $R_F$, $R_G$, $X_1$, $X_4$, $W_1$, $W_2$, $W_3$, $W_4$, Z, m, n, o, p are defined in formula (I).

In another embodiment, the present invention is directed to compounds of formula (II), wherein L is —$(CH_2)_mX_1$ $(CH_2)_nCH(R_8)C(R_{9A})(R_{9B})X_2(CH_2)_pX_3(CH_2)_qX_4$—; and wherein A, B, E, $P_1$, $P_2$, $R_1$, $R_2$, $R_3$, $R_4$, $R_5$, $R_8$, $R_{9A}$, $R_{9B}$, $R_{10}$, $R_{11}$, $R_A$, $R_B$, $R_C$, $R_D$, $R_E$, $R_F$, $R_G$, $X_1$, $X_2$, $X_3$, $X_4$, $W_1$, $W_2$, $W_3$, $W_4$, Z, m, n, o, p are defined in formula (I).

In another embodiment, the present invention is directed to compounds of formula (II), wherein L is —$(CH_2)_mX_1$ $(CH_2)_nCH(R_8)C(R_{9A})(R_{9B})X_2(CH_2)_pX_3(CH_2)_qX_4$—; $R_8$ is $NR_AR_B$; and wherein A, B, E, $P_1$, $P_2$, $R_1$, $R_2$, $R_3$, $R_4$, $R_5$, $R_{9A}$, $R_{9B}$, $R_{10}$, $R_{11}$, $R_A$, $R_B$, $R_C$, $R_D$, $R_E$, $R_F$, $R_G$, $X_1$, $X_2$, $X_3$, $X_4$, $W_1$, $W_2$, $W_3$, $W_4$, Z, m, n, o, p are defined in formula (I).

In another embodiment, the present invention is directed to compounds of formula (II), wherein L is —$(CH_2)_mX_1$ $(CH_2)_nCH(R_8)C(R_{9A})(R_{9B})X_2(CH_2)_pX_3(CH_2)_qX_4$—; $R_8$ is $NR_AR_B$; $R_{9A}$ and $R_{9B}$ together are oxo; and wherein A, B, E, $P_1$, $P_2$, $R_1$, $R_2$, $R_3$, $R_4$, $R_5$, $R_{10}$, $R_{11}$, $R_A$, $R_B$, $R_C$, $R_D$, $R_E$, $R_F$, $R_G$, $X_1$, $X_2$, $X_3$, $X_4$, $W_1$, $W_2$, $W_3$, $W_4$, Z, m, n, o, p are defined in formula (I).

In another embodiment, the present invention is directed to compounds of formula (II), wherein L is —$(CH_2)_mX_1$ $(CH_2)_nCH(R_8)C(R_{9A})(R_{9B})X_2(CH_2)_pX_3(CH_2)_qX_4$—; $R_8$ is $NR_AR_B$; $R_{9A}$ and $R_{9B}$ together are oxo; $X_2$ is $NR_C$; and wherein A, B, E, $P_1$, $P_2$, $R_1$, $R_2$, $R_3$, $R_4$, $R_5$, $R_{10}$, $R_{11}$, $R_A$, $R_B$, $R_C$, $R_D$, $R_E$, $R_F$, $R_G$, $X_1$, $X_3$, $X_4$, $W_1$, $W_2$, $W_3$, $W_4$, Z, m, n, o, p are defined in formula (I).

In another embodiment, the present invention is directed to compounds of formula (II), wherein L is —$(CH_2)_mX_1$ $(CH_2)_nCH(R_8)C(R_{9A})(R_{9B})X_2(CH_2)_pX_3(CH_2)_qX_4$—; $R_8$ is $NR_AR_B$; $R_{9A}$ and $R_{9B}$ together are oxo; $X_2$ is $NR_C$; $X_3$ is O; and wherein A, B, E, $P_1$, $P_2$, $R_1$, $R_2$, $R_3$, $R_4$, $R_5$, $R_{10}$, $R_{11}$, $R_A$, $R_B$, $R_C$, $R_D$, $R_E$, $R_F$, $R_G$, $X_1$, $X_4$, $W_1$, $W_2$, $W_3$, $W_4$, Z, m, n, o, p are defined in formula (I).

In another embodiment, the present invention is directed to compounds of formula (II), wherein L is —$(CH_2)_mX_1$ $(CH_2)_nCH(R_8)C(R_{9A})(R_{9B})X_2(CH_2)_pX_3(CH_2)_qX_4$—; $R_8$ is $NR_AR_B$; $R_{9A}$ and $R_{9B}$ together are oxo; $X_2$ is $NR_C$; $X_3$ is O; $X_4$ is O; and wherein A, B, E, $P_1$, $P_2$, $R_1$, $R_2$, $R_3$, $R_4$, $R_5$, $R_{10}$, $R_{11}$, $R_A$, $R_B$, $R_C$, $R_D$, $R_E$, $R_F$, $R_G$, $X_1$, $W_1$, $W_2$, $W_3$, $W_4$, Z, m, n, o, p are defined in formula (I).

In another embodiment, the present invention is directed to compounds of formula (II), wherein L is —$(CH_2)_mX_1$ $(CH_2)_nCH(R_8)C(R_{9A})(R_{9B})X_2(CH_2)_pX_3(CH_2)_qX_4$—; $R_8$ is $NR_AR_B$; $R_{9A}$ and $R_{9B}$ together are oxo; $X_2$ is $NR_C$; $X_3$ is O; $X_4$ is O; B is aryl; and wherein A, E, $P_1$, $P_2$, $R_1$, $R_2$, $R_3$, $R_4$, $R_5$, $R_{10}$, $R_{11}$, $R_A$, $R_B$, $R_C$, $R_D$, $R_E$, $R_F$, $R_G$, $X_1$, $W_1$, $W_2$, $W_3$, $W_4$, Z, m, n, o, p are defined in formula (I).

In another embodiment, the present invention is directed to compounds of formula (II), wherein L is —$(CH_2)_mX_1$ $(CH_2)_nCH(R_8)C(R_{9A})(R_{9B})X_2(CH_2)_pX_3(CH_2)_qX_4$—; $R_8$ is $NR_AR_B$; $R_{9A}$ and $R_{9B}$ together are oxo; $X_2$ is $NR_C$; $X_3$ is O; $X_4$ is O; B is aryl; A is

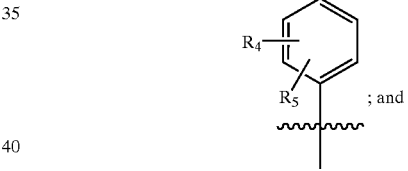

and wherein E, $P_1$, $P_2$, $R_1$, $R_2$, $R_3$, $R_4$, $R_5$, $R_{10}$, $R_{11}$, $R_A$, $R_B$, $R_C$, $R_D$, $R_E$, $R_F$, $R_G$, $X_1$, $W_1$, $W_2$, $W_3$, $W_4$, Z, m, n, o, p are defined in formula (I).

The present compounds can exist as therapeutically acceptable salts. The term "therapeutically acceptable salt," refers to salts or zwitterions of the compounds which are water or oil-soluble or dispersible, suitable for treatment of disorders without undue toxicity, irritation, and allergic response, commensurate with a reasonable benefit/risk ratio, and effective for their intended use. The salts can be prepared during the final isolation and purification of the compounds or separately by reacting an amino group of the compounds with a suitable acid. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetic, trifluoroacetic, glutamate, para-toluenesulfonate, undecanoate, hydrochloric, hydrobromic, sulfuric, phosphoric, and the like. The amino groups of the compounds can also be quaternized with alkyl chlorides, bromides, and iodides such as methyl, ethyl, propyl, isopropyl, butyl, lauryl, myristyl, stearyl, and the like.

Basic addition salts can be prepared during the final isolation and purification of the present compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts derived from methylamine, dimethylamine, trimethylamine, triethylamine, diethylamine, ethylamine, tributlyamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine, ethylenediamine, ethanolamine, diethanolamine, piperidine, piperazine, and the like, are contemplated as being within the scope of the present invention.

The present compounds can also exist as therapeutically acceptable prodrugs. The term "therapeutically acceptable prodrug," refers to those prodrugs or zwitterions which are suitable for use in contact with the tissues of patients without undue toxicity, irritation, and allergic response, are commensurate with a reasonable benefit/risk ratio, and are effective for their intended use. The term "prodrug," refers to compounds which are rapidly transformed in vivo to the parent compounds of formula (I) for example, by hydrolysis in blood.

Asymmetric centers can exist in the present compounds. Individual stereoisomers of the compounds are prepared by synthesis from chiral starting materials or by preparation of racemic mixtures and separation by conversion to a mixture of diastereomers followed by separation or recrystallization, chromatographic techniques, or direct separation of the enantiomers on chiral chromatographic columns. Starting materials of particular stereochemistry are either commercially available or are made by the methods described hereinbelow and resolved by techniques well-known in the art. Geometric isomers can exist in the present compounds. The invention contemplates the various geometric isomers and mixtures thereof resulting from the disposal of substituents around a carbon-carbon double bond, a cycloalkyl group, or a heterocycloalkyl group. Substituents around a carbon-carbon double bond are designated as being of Z or E configuration and substituents around a cycloalkyl or heterocycloalkyl are designated as being of cis or trans configuration.

Therapeutic compositions of the present compounds comprise an effective amount of the same formulated with one or more therapeutically acceptable excipients. The term "therapeutically acceptable excipient," as used herein, represents a non-toxic, solid, semi-solid or liquid filler, diluent, encapsulating material, or formulation auxiliary of any type. Examples of therapeutically acceptable excipients include sugars; cellulose and derivatives thereof, oils; glycols; solutions; buffering, coloring, releasing, coating, sweetening, flavoring, and perfuming agents; and the like. These therapeutic compositions can be administered parenterally, intracisternally, orally, rectally, or intraperitoneally.

Liquid dosage forms for oral administration of the present compounds comprise formulations of the same as emulsions, microemulsions, solutions, suspensions, syrups, and elixirs. In addition to the compounds, the liquid dosage forms can contain diluents and/or solubilizing or emulsifying agents. Besides inert diluents, the oral compositions can include wetting, emulsifying, sweetening, flavoring, and perfuming agents.

Injectable preparations of the present compounds comprise sterile, injectable, aqueous and oleaginous solutions, suspensions or emulsions, any of which can be optionally formulated with parenterally acceptable diluents, dispersing, wetting, or suspending agents. These injectable preparations can be sterilized by filtration through a bacterial-retaining filter or formulated with sterilizing agents which dissolve or disperse in the injectable media. PTP inhibition by the present compounds can be delayed by using a liquid suspension of crystalline or amorphous material with poor water solubility. The rate of absorption of the compounds depends upon their rate of dissolution which, in turn, depends on their crystallinity. Delayed absorption of a parenterally administered compound can be accomplished by dissolving or suspending the compound in oil. Injectable depot forms of the compounds can also be prepared by microencapsulating the same in biodegradable polymers. Depending upon the ratio of compound to polymer and the nature of the polymer employed, the rate of release can be controlled. Depot injectable formulations are also prepared by entrapping the compounds in liposomes or microemulsions which are compatible with body tissues.

Solid dosage forms for oral administration of the present compounds include capsules, tablets, pills, powders, and granules. In such forms, the compound is mixed with at least one inert, therapeutically acceptable excipient such as a carrier, filler, extender, disintegrating agent, solution retarding agent, wetting agent, absorbent, or lubricant. With capsules, tablets, and pills, the excipient can also contain buffering agents. Suppositories for rectal administration can be prepared by mixing the compounds with a suitable non-irritating excipient which is solid at ordinary temperature but fluid in the rectum.

The present compounds can be micro-encapsulated with one or more of the excipients discussed previously. The solid dosage forms of tablets, dragees, capsules, pills, and granules can be prepared with coatings and shells such as enteric and release-controlling. In these forms, the compounds can be mixed with at least one inert diluent and can optionally comprise tableting lubricants and aids. Capsules can also optionally contain opacifying agents which delay release of the compounds in a desired part of the intestinal tract.

Transdermal patches have the added advantage of providing controlled delivery of the present compounds to the body. Such dosage forms are prepared by dissolving or dispensing the compounds in the proper medium. Absorption enhancers can also be used to increase the flux of the compounds across the skin, and the rate of absorption can be controlled by providing a rate controlling membrane or by dispersing the compounds in a polymer matrix or gel.

Disorders caused or exacerbated by protein tyrosine phosphatase PTP1B activity are treated or prevented in a patient by administering to the same a therapeutically effective amount of the present compounds in such an amount and for such time as is necessary to achieve the desired result. The term "therapeutically effective amount," refers to a sufficient amount of the compound to treat protein tyrosine phosphatase PTP1B activity at a reasonable benefit/risk ratio applicable to any medical treatment. The specific therapeutically effective dose level for any particular patient will depend upon a variety of factors including the disorder being treated and the severity of the disorder; the activity of the compound employed; the specific composition employed; the age, body weight, general health, sex, and diet of the patient; the time of administration, route of administration, rate of excretion; the duration of the treatment; and drugs used in combination or coincidental therapy.

The total daily dose of the present compounds in single or divided doses can be in amounts, for example, from 0.01 to 50 mg/kg body weight or more usually from 0.1 to 25 mg/kg body weight. Single dose compositions can contain such amounts or submultiples thereof of the compounds to make up the daily dose. In general, treatment regimens comprise administration to a patient in need of such treatment from about 10 mg to about 1000 mg of the compounds per day in single or multiple doses. Specific compounds of formula (II) include, but are not limited to:

N-[5-({N-acetyl-4-[(carboxycarbonyl)(2-carboxyphenyl)amino]-3-ethylphenylalanyl}amino)pentanoyl]-L-tyrosine;

N-{5-[(N-acetyl-4-[(carboxycarbonyl)(2-carboxyphenyl)amino]-3-ethylphenylalanyl)amino]pentanoyl}-S-benzyl-L-cysteine;

N-{5-[(N-acetyl-4-[(carboxycarbonyl)(2-carboxyphenyl)amino]-3-ethylphenylalanyl)amino]pentanoyl}-L-methionine;

methyl N-{5-[(N-acetyl-4-[(carboxycarbonyl)(2-carboxyphenyl)amino]-3-ethylphenylalanyl)amino]pentanoyl}-L-methioninate;

N-{5-[(N-acetyl-4-[(carboxycarbonyl)(2-carboxyphenyl)amino]-3-ethylphenylalanyl)amino]pentanoyl}-S-ethyl-L-homocysteine;

N-[5-({N-acetyl-4-[(carboxycarbonyl)(2-carboxyphenyl)amino]-3-ethylphenylalanyl}amino)pentanoyl]-L-norleucine;

N-(5-{[3-(4-[(carboxycarbonyl)(2-carboxyphenyl)amino]-1-naphthyl)-N-(methoxycarbonyl)alanyl]amino}pentanoyl)-L-methionine;

N-{5-[(N-acetyl-4-[(carboxycarbonyl)(2-carboxyphenyl)amino]-3-isopropylphenylalanyl)amino]pentanoyl}-L-methionine;

N-{5-[(N-acetyl-4-[(carboxycarbonyl)(2-carboxy-5-chlorophenyl)amino]-3-ethylphenylalanyl)amino]pentanoyl}-L-methionine;

N-(5-{[N-acetyl-4-[(carboxycarbonyl)(2-carboxyphenyl)amino]-3-(2-hydroxyethyl)phenylalanyl]amino}pentanoyl)-L-methionine;

N-{[4-({[N-acetyl-4-[(carboxycarbonyl)(2-carboxyphenyl)amino]-3-(2-hydroxyethyl)phenylalanyl]amino}methyl)cyclohexyl]carbonyl}-L-norleucine;

methyl 2-[4-({N-[(allyloxy)carbonyl]-4-[(carboxycarbonyl)(2-carboxyphenyl)amino]-L-phenylalanyl}amino)butoxy]-6-hydroxybenzoate;

methyl 2-{4-[(N-acetyl-4-[(carboxycarbonyl)(2-carboxyphenyl)amino]-3-ethylphenylalanyl)amino]butoxy}-6-hydroxybenzoate;

methyl 2-{2-[2-({N-[(allyloxy)carbonyl]-4-[(carboxycarbonyl)(2-carboxyphenyl)amino]-L-phenylalanyl}amino)ethoxy]ethoxy}-6-hydroxybenzoate;

methyl 2-[(5-{[N-acetyl-3-(4-amino-1-naphthyl)-L-alanyl]amino}pentyl)oxy]-6-hydroxy-4-methylbenzoate;

methyl 4-{4-[(N-acetyl-4-amino-3-ethylphenylalanyl)amino]butoxy}-2-hydroxy-1,1'-biphenyl-3-carboxylate;

2-[4-({N-acetyl-4-[(carboxycarbonyl)(2-carboxyphenyl)amino]-3-ethylphenylalanyl}amino)butoxy]-6-hydroxybenzoic acid;

3-({5-[(N-acetyl-3-{4-[(carboxycarbonyl)(2-carboxyphenyl)amino]-1-naphthyl}-L-alanyl)amino]pentyl}oxy)-2-naphthoic acid;

methyl 6-{4-[(N-acetyl-4-[(carboxycarbonyl)(2-carboxyphenyl)amino]-3-ethylphenylalanyl)amino]butoxy}-3-bromo-2-hydroxybenzoate;

2-((carboxycarbonyl){4-[3-({4-[3-hydroxy-2-(methoxycarbonyl)phenoxy]butyl}amino)-3-oxopropyl]-[(carboxycarbonyl)(2-carboxyphenyl)amino]-1-naphthyl}amino)benzoic acid;

methyl 2-(4-{[4-[(carboxycarbonyl)(2-carboxyphenyl)amino]-N-(methoxycarbonyl)-L-phenylalanyl]amino}butoxy)-6-hydroxy-4-pentylbenzoate;

methyl 2-(4-{[4-[(carboxycarbonyl)(2-carboxyphenyl)amino]-N-(methoxycarbonyl)-L-phenylalanyl]amino}butoxy)-6-hydroxy-4-methoxybenzoate;

methyl 3-(4-{[4-[(carboxycarbonyl)(2-carboxyphenyl)amino]-N-(methoxycarbonyl)-L-phenylalanyl]amino}butoxy)-5-hydroxy-1,1'-biphenyl-4-carboxylate;

methyl 2-(4-{[4-[(carboxycarbonyl)(2-carboxyphenyl)amino]-N-(methoxycarbonyl)-L-phenylalanyl]amino}butoxy)-6-hydroxy-4-methylbenzoate;

methyl 2-(4-{[3-(4-[(carboxycarbonyl)(2-carboxyphenyl)amino]-3-ethylphenyl)propanoyl]amino}butoxy)-6-hydroxybenzoate;

methyl 2-(4-{[4-[(carboxycarbonyl)(2-carboxyphenyl)amino]-N-(methoxycarbonyl)-L-phenylalanyl]amino}butoxy)-4-chloro-6-hydroxybenzoate;

methyl 2-(4-{[4-[(carboxycarbonyl)(2-carboxyphenyl)amino]-N-(methoxycarbonyl)-L-phenylalanyl]amino}butoxy)-6-hydroxybenzoate;

4-[(carboxycarbonyl)(2-carboxyphenyl)amino]-N-{4-[2-(aminocarbonyl)-3-hydroxyphenoxy]butyl}-N-(methoxycarbonyl)-L-phenylalaninamide;

methyl 3-(4-{[4-[(carboxycarbonyl)(2-carboxyphenyl)amino]-N-(methoxycarbonyl)-L-phenylalanyl]amino}butoxy)-1-hydroxy-2-naphthoate;

4-[(carboxycarbonyl)(2-carboxyphenyl)amino]-N-(4-{3-hydroxy-2-[(methylamino)carbonyl]phenoxy}butyl)-N-(methoxycarbonyl)-L-phenylalaninamide;

methyl 2-(4-{[3-(4-[(carboxycarbonyl)(2-carboxyphenyl)amino]-1-naphthyl)-1-methylpropyl]amino}butoxy)-6-hydroxybenzoate;

methyl 2-(4-{[3-(4-[(carboxycarbonyl)(2-carboxyphenyl)amino]-1-naphthyl)propyl]amino}butoxy)-6-hydroxybenzoate;

4-[(carboxycarbonyl)(2-carboxyphenyl)amino]-N-(4-{2-[(ethylamino)carbonyl]-3-hydroxyphenoxy}butyl)-N-(methoxycarbonyl)-L-phenylalaninamide;

N-{4-[2-(acetylamino)-3-hydroxyphenoxy]butyl}-4-[(carboxycarbonyl)(2-carboxyphenyl)amino]-N-(methoxycarbonyl)-L-phenylalaninamide;

4-[(carboxycarbonyl)(2-carboxyphenyl)amino]-N-(4-{2-[(dimethylamino)carbonyl]-3-hydroxyphenoxy}butyl)-N-(methoxycarbonyl)-L-phenylalaninamide;

Determination of Biological Activity

A panel of different phosphatases is selected for assaying the different inhibitory activities exhibited by the claimed compounds. These phosphatases are selected on the basis of their homology to PTP1B, from the most homologous one, such as TCPTP, the moderate homologous phosphatase, such as SHP-2 and LAR, to the least homologous ones, such as cdc25c, CD45 and PP2B.

Purification of Human Protein Tyrosine Phosphatase 1B from E. coli.

Human protein tyrosine phosphatase 1B (PTP1B, amino acid residues 1–321) was expressed in E. coli BL21(DE3). The cell paste was resuspended in 4 cell paste volumes of lysis buffer containing 100 mM MES (pH 6.5), 100 mM NaCl, 1 mM EDTA, 1 mM DTT, 1 mM PMSF, 20 U/mL Benzonase, 0.5 mg/mL lysozyme, and 1 mM MgCl$_2$ and incubated for 35 minutes at room temperature. The cells were lysed at 11,000 psi using a Rannie homogenizer, and the homogenate was clarified in a Beckman GSA rotor at 10,000×g for 30 minutes at 4° C. The supernatant was loaded onto a 5×21 cm S-Sepharose-FF column (Amersham of 100 mM to 500 mM NaCl in the same buffer. The fractions (28 mL each) were assayed for purity by 10–20% Tris-Glycine SDS-PAGE. Fractions which contained >95% protein tyrosine phosphatase 1B were combined. These fractions were concentrated to approximately 10 mg/mL by ultrafiltration and chromatographed on a 180 mL (1.6 cm×90 cm) Superdex 75 column in 10 mM TRIS-HCl, pH 7.5, 25 mM NaCl, 0.2 mM EDTA, 3 mM DTT. The fractions (2 mL each) were assayed for purity by 10–20% Tris-Glycine SDS-PAGE. Fractions which contained >99% protein tyrosine phosphatase 1B were combined. Aliquots were frozen in liquid N2 and stored at −70C. until used. Once thawed, PTP1B was stored on ice and used within 6 hours.
Inhibition Constant Determination for Protein Tyrosine Phosphatase 1B:

Protein tyrosine phosphatase 1B activity was determined by measuring the rate of hydrolysis of a surrogate substrate, p-nitrophenyl phosphate (aka pNPP, C1907 Sigma, St. Louis, Mo.). The assay was carried out at room temperature in 96 well polypropylene or polyethylene plates in a total volume of 100 μL per well. Appropriate dilutions of the compounds were made in DMSO and then diluted ten fold with water. 10 μL of 5 concentrations of the test compound (inhibitor) or 10% DMSO in water were added to individual wells containing 40 μL of 3.2, 8, 20, and 50 mM pNPP in water. The reaction was initiated by adding 50 μL of diluted PTP1B diluted in 2× assay buffer containing 50 mM HEPES (pH=7.5), 300 mM NaCl and 0.2 mg/mL BSA. The phosphatase activity results in the formation of the colored product p-nitrophenol (pNP) which was continuously monitored at 405 nm every 30 seconds for 15 minutes using an appropriate plate reader. The absorbance at 405 nm was converted to nanomoles of pNP using a standard curve and the initial rate of pNP formation was calculated. For each concentration of test compound (inhibitor) or DMSO control, the initial rates are used to fit the rectangular hyperbola of Michaelis-Menten by non-linear regression analysis (GraphPad Software Prism 3.0). The ratio of the apparent Km/Vmax vs. inhibitor concentration was plotted and the competitive Ki was calculated by linear regression to be the negative x-intercept. The uncompetitive Ki was similarly calculated from the x-intercept of the plot of the reciprocal of the apparent Vmax versus the inhibitor concentration. (Cornish-Bowden, A. 1995. Fundamentals of Enzyme Kinetics. Revised edition. Portland Press, Ltd., London, U.K.).

Sources of Other Phosphates Used in the Selectivity Panel:

TCPTP used was either obtained commercially (catalog#752L New England Biolabs, 32 Tozer Rd, Beverly, Mass.) or as described for PTP1B. The purification of TCPTP differed from the purification of PTP1b in that chromatography of TCPTP (amino acid residues 1–283) was on Q-Sepharose-FF (Amersham Pharmacia Biotech) in 50 mM TRIS-HCl, pH 7.5, 2 mM DTT, 10% (v/v) glycerol, and was eluted with a 3 CV gradient of 0–300 mM NaCl in the same buffer. Fractions which contained TCPTP were selected and pooled based on SDS-PAGE. They were dialyzed versus 40 mM sodium phosphate, pH 7.5, 1 M ammonium sulfate, 10% (v/v) glycerol, 2 mM DTT, 1 mM sodium azide, applied to Phenyl Sepharose FF (Amersham Pharmacia Biotech), washed with 2.5 CV of the same buffer, and eluted with a 7 CV gradient of 1M to 0M NaCl in the same buffer. Fractions were assayed, pooled, frozen and stored as described for PTP1B.

SHP-2 (full length) was expressed in from *E. coli* and was purified as described for PTP-1B. Cells were lysed with a French press following by centrifugation to remove debris. Proteins were precipitated with 50% saturated ammonium sulfate, recovered by centrifugation, and chromatographed on Sephadex G-25 (Amersham Pharmacia Biotech) in 50 mM Tris-HCl pH 8, 10 mM NaCl, 1 mM DTT, 1 mM EDTA. The void volume was pooled and chromatographed on Q-Sepharose-FF in the same buffer, and SHP-2 was eluted with a 0–150 mM gradient of NaCl in the same buffer. Fractions were assayed, pooled and stored as described for PTP1B.

CDC25c was expressed as a fusion with glutathione-S-transferase (aka GST) in *E. coli*. Cells were lysed and debris removed as described for SHP-2, except lysis was in PBS (GibcoBRL Life Technologies, Grand Island, N.Y., Stock # 70011-044, diluted 10-fold). The soluble proteins were chromatographed on Glutathione-Sepharose FF (Amersham Pharmacia Biotech) and eluted with 10 mM reduced glutathione in 25 mM TRIS-HCl, pH 7.5, 150 mM NaCl. Fractions were assayed, pooled and stored as described for PTP1B.

CD45 was obtained commercially (catalog#SE-135 Biomol Research Laboratories, Inc. 5120 Butler Pike, Plymouth Meeting, Pa.).

LAR was obtained commercially (catalog#P0750L New England Biolabs, 32 Tozer Rd, Beverly, Mass.).

Bovine PP2B was obtained commercially (C1907 Sigma, St. Louis, Mo.).

Inhibition Constant Determination for Other Phosphatases in the Selectivity Panel:

The Kic and Kiu values are calculated as described for PTP1B. The assays were performed as described for PTP-1B except for the following changes. All the phosphatases except PP2B use the same 2× assay buffer as PTP1B. PP2B uses a 2× assay buffer which contains 100 mM TRIS-HCl pH 8.6, 40 mM $MgCl_2$, 0.2 mM $CaCl_2$, 6 mM DTT, 0.2 mg/mL BSA. The concentrations of pNPP present in 40 ul were the same for TCPTP, CD45, LAR and PTP1B. For PP2B they were 24 mM, 60 mM, 150 mM, and 375 mM; for cdc25C they were 16 mM, 40 mM, 100 mM, and 250 mM; for SHP-2 they were 6.4 mM, 16 mM, 40 mM, and 100 mM.

TABLE 1

| | Phosphatase Inhibition Constants ($K_{ic}$) | | | | | | |
|---|---|---|---|---|---|---|---|
| Compound of Example # | PTP1B | TC-PTP | SHP-2 | LAR | CD45 | PP2B | Cdc25c |
| 3 | 0.077 +/− 0.012 | 0.38 +/− 0.080 | 17 | 5.0 | >200 | >200 | >200 |
| 13 | 0.016 +/− 0.003 | 0.57 +/− 0.012 | 14.2 | 4.6 | >200 | >200 | >200 |

($K_{ic}$ expressed in μM +/− S.D.)

The results shown in Table 1, demonstrate that compounds of Example 3 and 13 are at least 3 fold selective for PTP1B over the most homologous phosphatase, TCPTP, are 50 fold selective for PTP1B over SHP-2 and LAR, and are 2,000 fold selective for PTP1B over CD45, PP2B and Cdc25C. Moreover the compounds of the present invention were found to inhibit protein tyrosine phosphatase 1B with inhibitory constants in a range of about 0.005 $\mu$M to about 10 $\mu$M. In a preferred range, the compounds inhibited protein tyrosine phosphatase 1B with inhibitory constants in a range of about of about 0.005 $\mu$M to about 1 $\mu$M; and in a more preferred range, the compounds inhibited protein tyrosine phosphatase 1B with inhibitory constants in a range of about of about 0.005 $\mu$M to about 0.5 $\mu$M.

Synthetic Methods

Abbreviations which have been used in the descriptions of the scheme and the examples that follow are: dba for dibenzylideneacetone; DMSO for dimethylsulfoxide; NMP for N-methylpyrrolidinone; DMF for N,N-dimethylformamide; TFA for trifluoroacetic acid; THF for tetrahydrofuran; EDAC for 1-(3-dimethylaminopropyl)-3-ethylcarbodiimide hydrochloride; and HOBT for 1-hydroxybenzotriazole hydrate.

The compounds and processes of the present invention will be better understood in connection with the following synthetic schemes which illustrate the methods by which the compounds of the invention may be prepared. The groups $R^1$, $R^2$ and $R^3$ are as defined above unless otherwise noted below.

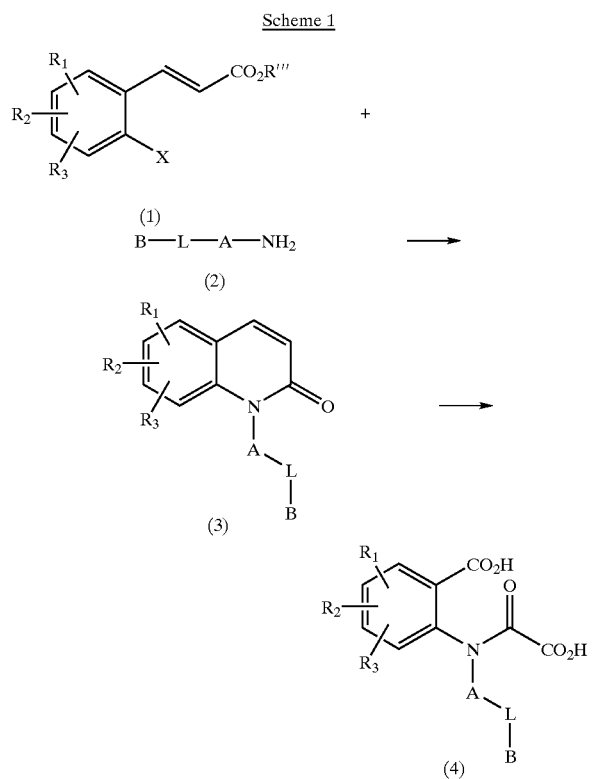

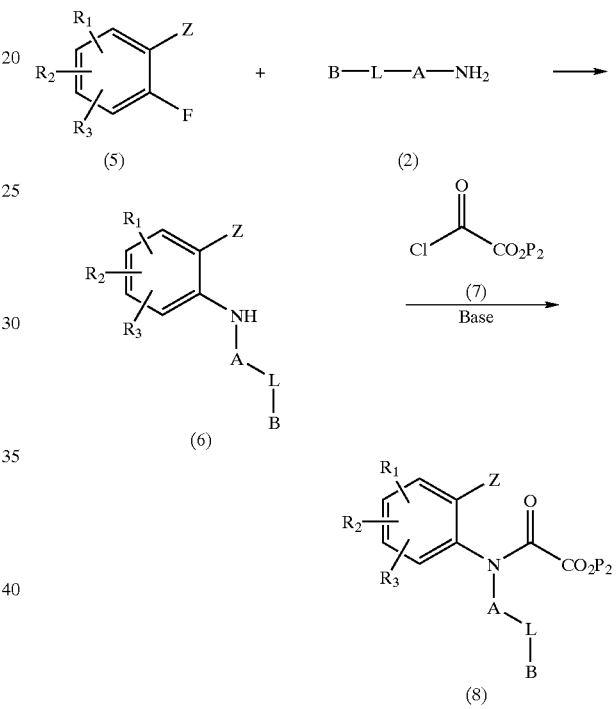

toluene. The reaction temperature can range between 60° C. to about 110° C. and depends on the method chosen. Reaction times are typically about 2 to about 8 hours.

Compounds of formula (3) can be converted to compounds of formula (4) by treatment with an oxidizing agent. Representative oxidizing agents include $KMnO_4$, ozone and hydrogen peroxide, and $CrO_3$. Examples of solvents used in these reactions include pyridine, water, and mixtures thereof. The reaction temperature is about 0° C. to about 35° C. and depends on the method chosen. Reaction times are typically about 12 to about 24 hours.

The acid functionalities of compounds of formula (4) can be converted to esters, amides or prodrugs by methods well known to those skilled in the art.

As shown in Scheme 1, compounds of formula (1) (R′′′ is alkyl; X is Br or I) can be reacted with compounds of formula (2) in the presence of a palladium catalyst and base to form compounds of formula (3). Representative palladium catalysts include $Pd_2dba_3$ with 2-dicyclohexylphosphino-2'-(N,N-dimethyl) aminobiphenyl, $Pd_2dba_3$ with tricyclohexylphosphine, and $Pd_2dba_3$ with $PPh_3$. Representative bases include sodium hydride, potassium hydride, and calcium hydride. Examples of solvents used in these reactions include benzene and As shown in Scheme 2, compounds of formula (5) can be reacted with compounds of formula (2) under elevated temperatures to provide compounds of formula (6). Examples of solvents used in these reactions include DMSO, dioxane, and NMP. The reaction temperature is about 80° C. to about 120° C. Reaction times are typically about 12 to about 24 hours.

The amine functionality of compounds of formula (6) can be reacted with compounds of formula (7) in the presence of base to provide compounds of formula (8). Examples of compounds of formula (7) include but are not limited to methyl oxalyl chloride, ethyl oxalyl chloride, benzyl oxalyl chloride and tert-butyl oxalyl chloride. Representative bases include pyridine, triethylamine, and diisopropylethylamine. Examples of solvents used in these reactions include diethyl ether, methyl tert-butyl ether, and dioxane. The reaction temperature is about 20° C. to about 30° C. Reaction times are typically about 8 to about 18 hours.

The ester functionality of compounds of formula (8) can be hydrolyzed and further converted to esters, amides or prodrugs by methods known to those skilled in the art.

Scheme 3

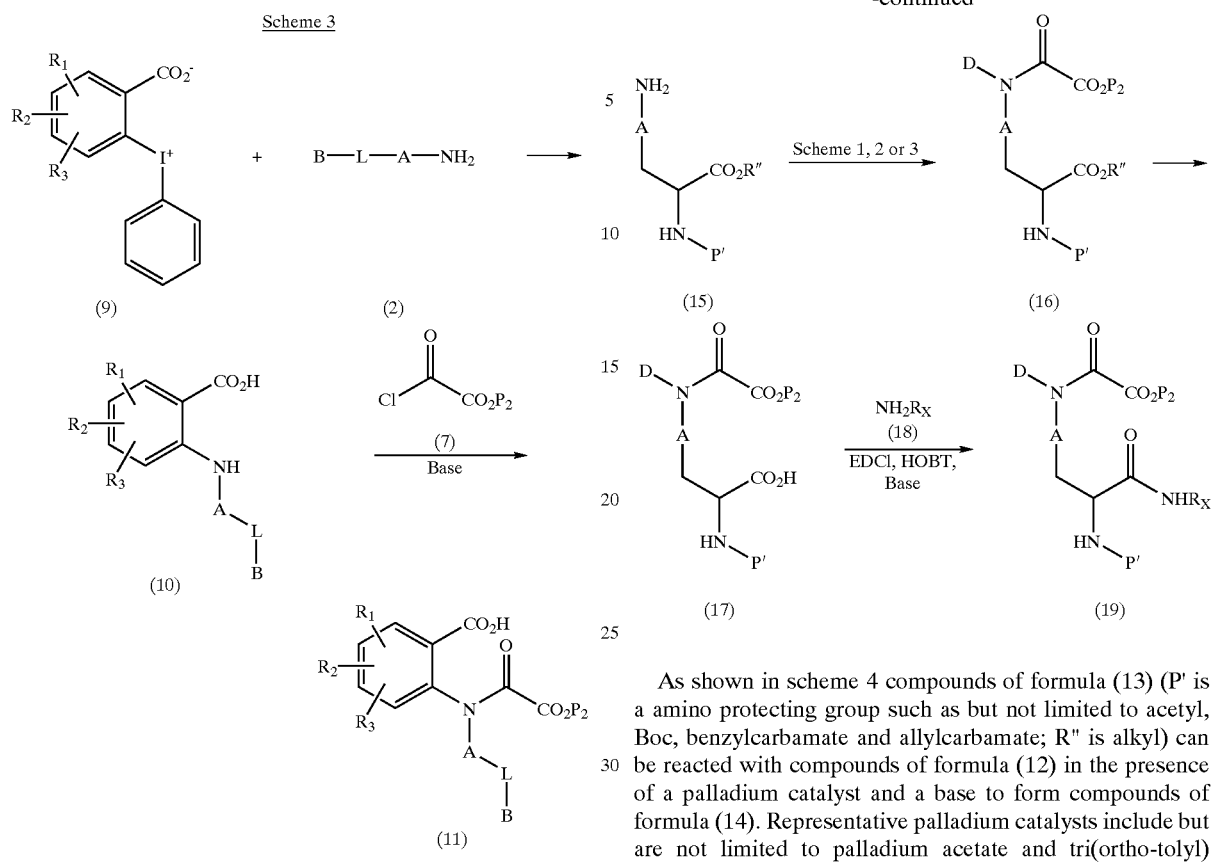

As shown in Scheme 3, compounds of formula (9) can be reacted with compounds of formula (2) in the presence of catalytic copper(II) acetate to provide compounds of formula (10). Examples of solvents used in these reactions include isopropanol, n-propanol, butanol, and pentanol. The reaction temperature is about 70° C. to about 100° C. Reaction times are typically about 4 to about 12 hours.

The amine functionality of compounds of formula (10) can be reacted with compounds of formula (7) in the presence of base in a similar fashion as described in Scheme 2, to provide compounds of formula (11).

The ester functionality of compounds of formula (11) can be hydrolyzed and further converted to esters, amides or prodrugs by methods known to those skilled in the art.

Scheme 4

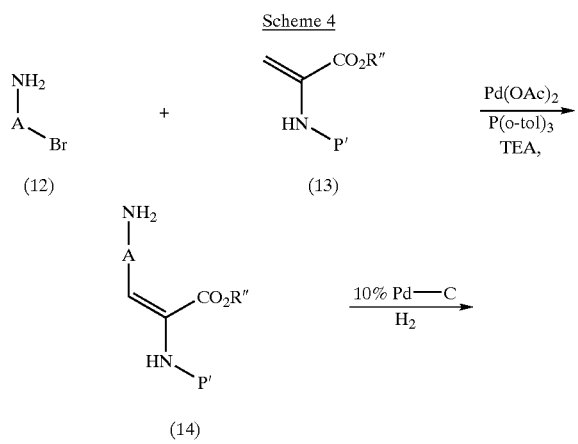

As shown in scheme 4 compounds of formula (13) (P' is a amino protecting group such as but not limited to acetyl, Boc, benzylcarbamate and allylcarbamate; R" is alkyl) can be reacted with compounds of formula (12) in the presence of a palladium catalyst and a base to form compounds of formula (14). Representative palladium catalysts include but are not limited to palladium acetate and tri(ortho-tolyl) phosphine. Representative bases include but are not limited to triethylamine and diisopropylethylamine. A typical solvent used in this reaction is acetonitrile. The reduction of the alkene of compound (14) in the presence of 10% palladium under 4 atmospheres of hydrogen in such solvents as methanol, ethanol or ethyl acetate provides compounds of formula (15). The amine portion of compounds of formula (15) may be converted to the substituted amine of compounds of formula (16) through the methods described in Scheme 1, 2 or 3. The hydrolysis of R" of compounds of formula (16) can be effected by methods known to those skilled in the art to provide compounds of formula (17). Compounds of formula (17) can be coupled to amines of general formula (18) to provide compounds of formula (19) using reagents such as 1-[-3-(dimethylamino)propyl]-3-ethylcarbodiimide hydrochloride and 1-hydroxybenzotriazole and a base such as triethylamine, N-methyl morpholine or diisopropylethylamine is such solvents as methylene chloride.

The ester functionality of compounds of formula (19) can be hydrolyzed and further converted to esters, amides or prodrugs by methods known to those skilled in the art.

Scheme 5

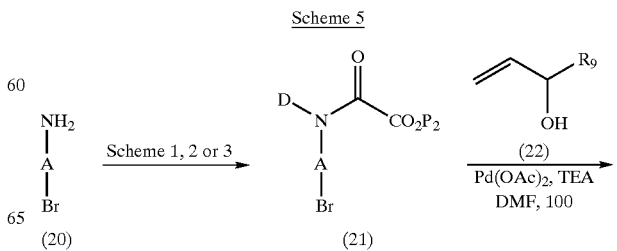

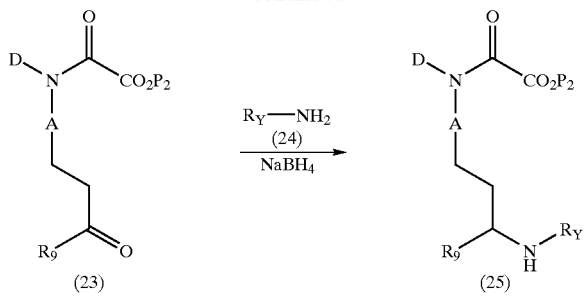

As shown in scheme 5, compounds of formula (20) can be converted to compounds of formula (21) through methods described in Scheme 4. Compounds of formula (21) can be reacted with compounds of formula (22) in the presence of a palladium catalyst and a base to provide compounds of formula (23). Typical palladium catalysts include but are not limited to palladium acetate and tri(ortho-tolyl)phosphine. Typical bases include but are not limited to triethylamine or diisopropylethylamine. Compounds of formula (23) can be reacted with amines of formula (24) in the presence of a reducing compound such as but not limited to sodium borohydride or sodium cyanoborohydride to provide compounds of formula (25).

The ester functionality of compounds of formula (25) can be hydrolyzed and further converted to esters, amides or prodrugs by methods known to those skilled in the art.

The present invention will now be described in connection with certain preferred embodiments which are not intended to limit its scope. On the contrary, the present invention covers all alternatives, modifications, and equivalents as can be included within the scope of the claims. Thus, the following examples, which include preferred embodiments, will illustrate the preferred practice of the present invention, it being understood that the examples are for the purposes of illustration of certain preferred embodiments and are presented to provide what is believed to be the most useful and readily understood description of its procedures and conceptual aspects.

Compounds of the invention were named by ACD/ChemSketch version 5.01 (developed by Advanced Chemistry Development, Inc., Toronto, ON, Canada) or were given names which appeared to be consistent with ACD nomenclature.

EXAMPLE 1

N-[5-({N-acetyl-4-[(carboxycarbonyl)(2-carboxyphenyl)amino]-3-ethylphenylalanyl}amino)pentanoyl]-L-tyrosine

EXAMPLE 1A benzyl 2-(acetylamino)acrylate

To a mixture of 2-acetamidoacrylic acid (10.3 g, 80.0 mmol) and $K_2CO_3$ (10 g, 72.5 mmol) in N,N-dimethylformamide (50 mL) was added benzyl bromide (8.7 ml, 72.5 mmol) at room temperature then stirred at room temperature for 3 hours. The mixture was partitioned between ethyl acetate and water (50 mL, 1:1), the aqueous layer was extracted with ethyl acetate (2×45 mL). The combined organic layers was washed with brine (2×25 mL), dried ($MgSO_4$), filtered and concentrated under reduced pressure to provide titled compound. MS (ESI(+)) m/e 220(M+H)$^+$; $^1$H NMR (300 MHz, DMSO-d$_6$) δ 9.37 (s, 1H), 7.43–7.30 (m, 5H), 6.13 (s, 1H), 5.70 (s, 1H), 5.23 (s, 2H), 2.01 (s, 3H).

EXAMPLE 1B benzyl (2E)-2-(acetylamino)-3-(4-amino-3-ethylphenyl)-2-propenoate To benzyl 2-(acetylamino)acrylate (80.0 mmol) in acetonitrile (200 mL) was added Pd(OAc)$_2$ (488 mg, 2.18 mmol), (o-Tol)$_3$P (1.32 g, 4.35 mmol), Et$_3$N (20 mL) followed by addition of 4-bromo-2-ethylaniline (14.5 g, 72.5 mmol). The reaction mixture was heated to reflux overnight, concentrated under reduce pressure, taken up in ethyl acetate, washed with aqueous NaHCO$_3$, dried (MgSO$_4$), filtered and concentrated under reduced pressure. The residue was precipitated from ethyl acetate/hexane to provide the titled compound (6.3 g). The filtrate was precipitated a second time to provide and additional 5 g of the titled compound. MS (ESI(+)) m/e 339 (M+H)$^+$; $^1$H NMR (300 MHz, DMSO-d$_6$) δ 9.31 (s, 1H), 7.40–7.20 (m, 8H), 6.59 (d, 1H), 5.52 (s, 2H), 5.16 (s, 2H), 2.42 (q, 2H), 1.98 (s, 3H), 1.13 (t, 3H).

EXAMPLE 1C

N-acetyl-4-amino-3-ethylphenylalanine

A mixture of benzyl (2E)-2-(acetylamino)-3-(4-amino-3-ethylphenyl)-2-propenoate (5 g) and 10% Pd—C (100 mg) in methanol (50 mL) was stirred under an atmosphere of hydrogen (4 atmospheres) at ambient temperature overnight to provide the titled compound. MS (ESI(+)) m/e 251 (M+H)$^+$; $^1$H NMR (300 MHz, DMSO-d$_6$) δ 8.02 (d, 1H), 6.77–6.70 (m, 2H), 6.50 (d, 1H), 4.31–4.21 (m, 1H), 2.84 (dd, 1H), 2.65 (dd, 1H), 2.39 (q, 2H), 1.78 (s, 3H), 1.10 (t, 3H).

EXAMPLE 1D allyl 2-(acetylamino)-3-(4-amino-3-ethylphenyl)propanoate

A mixture of N-acetyl-4-amino-3-ethylphenylalanine (2.0 g, 8.0 mmol), Cs$_2$CO$_3$ (2.61 g, 8.0 mmol) and allyl bromide (692 μL, 8.0 mmol) in N,N-dimethylformamide (40 mL) was stirred at room temperature for 3 hours, concentrated under reduce pressure and partitioned between ethyl acetate and water (100 mL, 1:1). The organic phase was washed with brine (1×50 mL), dried (MgSO$_4$), filtered and concentrated under reduced pressure. The residue was purified by on silica gel with ethyl acetate/hexane (5:3) to provide titled compound (1.44 g). MS (ESI(+)) m/e 291 (M+H)$^+$; $^1$H NMR (300 MHz, DMSO-d$_6$) δ 8.23 (d, 1H), 6.77–6.70 (m, 2H), 6.50 (d, 1H), 5.90–5.76 (m, 1H), 5.30–5.15 (m, 2H), 4.67 (s, 2H), 4.54–4.50 (m, 2H), 4.38–4.30 (m, 1H), 2.77(dddd, 2H), 2.39 (q, 2H), 1.80 (s, 3H), 1.10 (t, 3H).

EXAMPLE 1E

2-{4-[2-(acetylamino)-3-(allyloxy)-3-oxopropyl][tert-butoxy(oxo)acetyl]-2-ethylanilino}benzoic acid The titled compound was prepared according to the method described in Example 7 F-G by substituting allyl 2-(acetylamino)-3-(4-amino-3-ethylphenyl)propanoate for 3-(4-amino-naphthalen-1-yl)-2-methoxycarbonylamino-propionic acid 2-trimethylsilanyl-ethyl ester. MS (APCI(+)) m/e 539 (M+H)$^+$.

EXAMPLE 1F benzhydryl 2-{4-[2-(acetylamino)-3-(allyloxy)-3-oxopropyl][tert-butoxy(oxo)acetyl]-2-ethylanilino}benzoate To 2-{4-[2-(acetylamino)-3-(allyloxy)-3-oxopropyl][tert-butoxy(oxo)acetyl]-2-ethylanilino}benzoic acid in acetone was added diphenyldiazomethane (until all starting material was consumed as evident by monitoring via TLC). The reaction mixture was concentrated under reduced pressure, purified on silica gel using ethyl acetate as eluent to provide the titled compound. MS (ESI(+)) m/e 705 (M+H)$^+$; $^1$H NMR (300 MHz, DMSO-d$_6$) δ 8.51–8.01 (m, 2H), 7.73–6.86 (m, 16H), 5.93–5.78 (m, 1H), 5.34–5.10 (m, 2H), 4.57–4.40 (m, 3H), 3.10–2.84 (m, 2H), 2.58–2.42 (m, 2H), 1.82–1.77 (m, 3H), 1.22–0.78 (m, 3H), 1.07, 1.05, 1.00 (s, s, s, 9H).

EXAMPLE 1G

N-acetyl-4-{2-[(benzhydryloxy)carbonyl][tert-butoxy(oxo)acetyl]anilino}-3-ethylphenylalanine A mixture benzhydryl 2-{4-[2-(acetylamino)-3-(allyloxy)-3-oxopropyl][tert-butoxy(oxo)acetyl]-2-ethylanilino}benzoate (3.4 g, 4.8 mmol), Pd(Ph$_3$P)$_4$ (166 mg, 0.144 mmol) and morpholine (0.5 ml, 5.8 mmol) in dichloromethane (25 mL) was stirred under N$_2$ atmosphere for 2 hours, partitioned between ethyl acetate and water (75 mL, 1:1). The organic phase was washed with 1N HCl (1×25 mL), brine (1×25 mL), dried (MgSO$_4$), filtered and concentrated under reduced pressure to provide the titled compound (3.3 g). MS (ESI(+)) m/e 665 (M+H)$^+$; $^1$H NMR (300 MHz, DMSO-d$_6$) δ 12.67 (s, 1H), 8.51–7.98(m, 2H), 7.73–6.86 (m, 16H), 4.53–4.33 (m, 1H), 3.12–2.76 (m, 2H), 2.58–2.42 (m, 2H), 1.82–1.77 (m, 3H), 1.22–0.78 (m, 3H), 1.06, 1.04, 1.00 (s, s, s, 9H).

EXAMPLE 1H 2-(trimethylsilyl)ethyl 5-[(tert-butoxycarbonyl) amino]pentanoate A mixture of boc-d-aminovaleric acid (13.0 g, 59.5 mmol), pyridine (45 mL), (2-trimethylsilyl)ethanol (10.3 ml, 71.8 mmol) and dicyclohexylcarbodiimide (13.5 g, 65.4 mmol) in acetotnitrile (60 mL) was stirred cold (ice bath) for 1 hour and then kept in a refrigerator overnight. The suspension was filtered and the filtrate concentrated under reduced pressure to remove most of pyridine, diluted with ethyl acetate and washed with 1N HCl, saturated NaHCO$_3$. The organic phase was dried (MgSO$_4$), filtered and concentrated. The concentrate was purified by flash column chromatography on silica gel with hexane/ethyl acetate (4:1) to provide the desired product (15.3 g). MS (ESI(+)) m/e 318 (M+H)$^+$; $^1$H NMR (300 MHz, DMSO-d$_6$) δ 6.77 (t, 1H), 4.11–4.03 (m, 2H), 3.30 (m, 2H), 2.91–2.83 (m, 2H), 2.26–2.20 (m, 2H), 1.52–1.40 (m, 2H), 1.35 (s, 9H), 0.96–0.88 (m, 2H).

EXAMPLE 1I benzhydryl 2-{4-[2-(acetylamino)-3-oxo-3-({5-oxo-5-[2-(trimethylsilyl)ethoxy]pentyl}amino)propyl] [tert-butoxy(oxo)acetyl]-2-ethylanilino}benzoate 2-(trimethylsilyl)ethyl 5-[(tert-butoxycarbonyl)amino] pentanoate (317 mg, 1.0 mmol) was treated with 4N HCl in dioxane at room temperature for 30 minutes, then concentrated under reduced pressure. The residue (665 mg, 1.0 mmol), N-acetyl-4-{2-[(benzhydryloxy)carbonyl][tert-butoxy(oxo)acetyl]anilino}-3-ethylphenylalanine (665 mg, 1.0 mmol), 2-(1H-benzotriazole-1-yl)-1,1,3,3-tetramethyluronium tetrafluoroborate (321 mg, 1.0 mmol) and diisopropylethylamine (521 μL, 3.0 mmol) in N,N-dimethylformamide (2 mL) was stirred at ambient temperature overnight, diluted with ethyl acetate and washed with aqueous NaHCO$_3$ (1×30 mL), brine (1×30 mL), dried (MgSO$_4$), filtered and concentrate under reduced pressure. The residue was purified on silica gel eluting with ethyl acetate to provide of titled compound 480 mg. MS (APCI (+)) m/e 864 (M+H)$^+$.

EXAMPLE 1J

5-{[2-(acetylamino)-3-(4-{2-[(benzhydryloxy) carbonyl][tert-butoxy(oxo)acetyl]anilino}-3-ethylphenyl)propanoyl]amino}pentanoic acid A solution of benzhydryl 2-{4-[2-(acetylamino)-3-oxo-3-({5-oxo-5-[2-(trimethylsilyl)ethoxy]pentyl}amino)propyl] [tert-butoxy(oxo)acetyl]-2-ethylanilino}benzoate (356 mg, 0.41 mmol) and tetrabutylammonium fluoride-1M in THF (4 mL) was stirred at room temperature for 2 hours, diluted with ethyl acetate, washed with 1N HCl (3×25 mL), dried (MgSO$_4$), filtered and concentrated under reduced pressure to provide the titled compound (305 mg). MS (APCI(+)) m/e 764 (M+H)$^+$; $^1$H NMR (300 MHz, DMSO-d$_6$) δ 8.31–7.90 (m, 2H), 7.73–6.85 (m, 16H), 4.43–4.33 (m, 1H), 3.22–2.48 (m, 6H), 2.22–2.15 (m, 2H), 1.80–1.72 (m, 3H), 1.62–1.25 (m, 4H), 1.05, 1.04, 1.00 (s, s, s, 9H), 1.25–0.78 (m, 3H).

EXAMPLE 1K (2S)-2-[(5-{[2-(acetylamino)-3-(4-{2-[(benzhydryloxy)carbonyl][tert-butoxy(oxo)acetyl] anilino}-3-ethylphenyl)propanoyl]amino}pentanoyl) amino]-3-(4-tert-butoxyphenyl)propanoic acid A mixture 5-{[2-(acetylamino)-3-(4-{2-[(benzhydryloxy) carbonyl][tert-butoxy(oxo)acetyl]anilino}-3-ethylphenyl) propanoyl]amino}pentanoic acid (30 mg, 0.04 mmol), H-TYR(TBU)-OTBU HCL(26 mg, 0.08 mmol), 2-(1H-benzotriazole-1-yl)-1,1,3,3-tetramethyluronium tetrafluoroborate (16 mg, 0.048 mmol) and diisopropylethylamine (26 μL) in N,N-dimethylformamide (250 μL) was stirred at ambient temperature overnight, concentrated under reduced pressure and the residue purified by reverse-phase HPLC eluting with 5–100% acetonitrile/aqueous 0.1% trifluoroacetic acid to provide the titled compound.

EXAMPLE 1L

N-[5-({N-acetyl-4-[(carboxycarbonyl)(2-carboxyphenyl)amino]-3-ethylphenylalanyl}amino) pentanoyl]-L-tyrosine (2S)-2-[(5-{[2-(acetylamino)-3-(4-{2-[(benzhydryloxy) carbonyl][tert-butoxy(oxo)acetyl]anilino}-3-ethylphenyl) propanoyl]amino}pentanoyl)amino]-3-(4-tert-butoxyphenyl)propanoic acid was treated with trifluoroacetic acid/dichloromethane (1 mL, 1:1) at ambient temperature for 3 hours, concentrated under reduced pressure and purified by HPLC eluting with 5–100% acetonitrile/aqueous 0.1% trifluoroacetic acid to provide the titled compound. MS (ESI(+)) m/e 705 (M+H)$^+$; $^1$H NMR (500 MHz, DMSO-d$_6$) δ 12–13.5 (bs, 2H), 9.18 (s, 1H), 8.11–7.78 (m, 4H), 7.59–6.98 (m, 7H), 6.80–6.61 (m, 3H), 4.57–4.40 (m, 1H), 4.39–4.32 (m, 1H), 3.00–2.55 (m, 6H), 2.04–2.00 (m, 2H), 1.78, 1.75 (s, s, 3H), 1.40–1.36 (m, 2H), 1.35–1.20 (m, 2H), 1.35–0.91 (m, 3H).

EXAMPLE 2

N-{5-[(N-acetyl-4-[(carboxycarbonyl)(2-carboxyphenyl)amino]-3-ethylphenylalanyl)amino] pentanoyl}-S-benzyl-L-cysteine The titled compound was prepared according to the procedure described in Example 1K-L substituting 8-benzyl- L-cysteine tert-butyl ester hydrochloride for H-TYR (TBU)-OTBU HCL. MS (ESI(+)) m/e 735(M+H)$^+$; $^1$H NMR (500 MHz, DMSO-d$_6$) 8.16–8.04 (m, 2H), 7.95–7.78 (m, 2H), 7.58–6.88 (m, 11H), 4.50–4.40 (m, 2H), 3.74(s, 2H), 3.07–2.55 (m, 6H), 2.08–2.05 (m, 2H), 1.78, 1.75 (s, s, 3H), 1.45–1.42 (m, 2H), 1.41–1.32 (m, 2H), 1.28–0.91 (m, 3H).

EXAMPLE 3

N-{5-[(N-acetyl-4-[(carboxycarbonyl)(2-carboxyphenyl)amino]-3-ethylphenylalanyl)amino]pentanoyl}-L-methionine The titled compound was prepared according to the procedure described in Example 1K-L, substituting H-MET-OTBU HCL for H-TYR (TBU)-OTBU HCL. MS (ESI(+)) m/e 673 (M+H)$^+$; $^1$H NMR (500 MHz, DMSO-d$_6$) δ 8.12–8.02 (m, 2H), 7.95–7.79 (m, 2H), 7.57–6.74 (m, 6H), 4.50–4.40 (m, 1H), 4.32–4.27 (m, 1H), 3.07–2.45 (m, 6H), 2.15–2.07 (m, 2H), 2.03 (s, 3H), 1.98–1.79 (m, 2H), 1.78, 1.75 (s, s, 3H), 1.48–1.42 (m, 2H), 1.40–1.32 (m, 2H), 1.28–0.91 (m, 3H).

EXAMPLE 4 methyl N-{5-[(N-acetyl-4-[(carboxycarbonyl)(2-carboxyphenyl)amino]-3-ethylphenylalanyl)amino]pentanoyl}-L-methioninate The titled compound was prepared according to the procedure described in Example 1K-L, substituting L-methionine methyl ester hydrochloride for H-TYR (TBU)-OTBU HCL. MS (ESI(+)) m/e 687 (M+H)$^+$; $^1$H NMR (500 MHz, DMSO-d$_6$) δ 8.20–8.03 (m, 2H), 7.95–7.80 (m, 2H), 7.56–6.74 (m, 6H), 4.50–4.40 (m, 1H), 4.38–4.32 (m, 1H), 3.62 (s, 3H), 3.07–2.43 (m, 6H), 2.13–2.07 (m, 2H), 2.03 (s, 3H), 1.97–1.79 (m, 2H), 1.78, 1.75 (s, s, 3H), 1.48–1.42 (m, 2H), 1.38–1.32 (m, 2H), 1.28–0.92 (m, 3H).

EXAMPLE 5

N-{5-[(N-acetyl-4-[(carboxycarbonyl)(2-carboxyphenyl)amino]-3-ethylphenylalanyl)amino]pentanoyl}-S-ethyl-L-homocysteine The titled compound was prepared according to the procedure described in Example 1K-L, substituting L-ethionine methyl ester hydrochloride for H-TYR (TBU)-OTBU HCL, followed by hydrolysis with 1N NaOH (3 eq.)/MeOH (250 μL)/THF (250 μL) at ambient temperature for 2 hours. MS (ESI(+)) m/e 687 (M+H)$^+$; $^1$H NMR (500 MHz, DMSO-d$_6$) δ 8.14–8.02 (m, 2H), 7.95–7.79 (m, 2H), 7.57–6.74 (m, 6H), 4.50–4.40 (m, 1H), 4.32–4.27 (m, 1H), 3.07–2.45 (m, 8H), 2.15–2.07 (m, 2H), 1.97–1.79 (m, 2H), 1.78, 1.75 (s, s, 3H), 1.48–1.42 (m, 2H), 1.38–1.32 (m, 2H), 1.28–0.91 (m, 3H), 1.16 (t, 3H).

EXAMPLE 6

N-[5-({N-acetyl-4-[(carboxycarbonyl)(2-carboxyphenyl)amino]-3-ethylphenylalanyl}amino)pentanoyl]-L-norleucine The titled compound was prepared according to the procedure described in Example 5, substituting L-norleucine methyl ester hydrochloride for L-ethionine methyl ester hydrochloride. MS (ESI(+)) m/e 655 (M+H)$^+$; $^1$H NMR (500 MHz, DMSO-d$_6$) δ 8.12–7.79 (m, 4H), 7.57–6.74 (m, 6H), 4.52–4.40 (m, 1H), 4.18–4.13 (m, 1H), 3.05–2.52 (m, 6H), 2.15–2.05 (m, 2H), 2.03 (s, 3H), 1.78, 1.75 (s, s, 3H), 1.72–1.50 (m, 2H), 1.48–1.40 (m, 2H), 1.40–1.32 (m, 2H), 1.30–0.91 (m, 5H), 0.85 (t, 3H).

EXAMPLE 7

N-(5-{[3-(4-[(carboxycarbonyl)(2-carboxyphenyl)amino]-1-naphthyl)-N-(methoxycarbonyl)alanyl]amino}pentanoyl)-L-methionine

EXAMPLE 7A 1-methyl-4-nitro-naphthalene

The titled compound was prepared according to the procedure described in J. Org. Chem. 1991, 56, 1739 Davalli, S.; Lunazzi, L.; Macciantelli, D.;.

EXAMPLE 7B 3-(4-nitro-1-naphthyl)alanine

The titled compound was prepared from 1-methyl-8-nitronaphthalene according to the procedure described in J. Med. Chem. 1967, 10, 293 Benigni, J. D.; Minnis, R. L.;

EXAMPLE 7C 2-methoxycarbonylamino-3-(4-nitro-naphthalen-1-yl)-propionic acid A mixture of 3-(4-nitro-1-naphthyl)alanine (0.65 g, 2.5 mmol), aqueous NaHCO$_3$ (5 mL) and methylchloroformate (230 uL, 3 mmol, 1.2 eq) in dioxane (10 mL) was stirred for 3 hours, acidified to a ph <3 with aqueous 2N HCl and extracted with ethyl acetate. The combined organic layers was washed with water (1×25 mL), brine(1×25 mL), dried (MgSO$_4$), filtered and concentrated under reduce pressure to provide the titled compound. MS (APCI(+)) m/e 319 (M+H)$^+$.

EXAMPLE 7D 2-methoxycarbonylamino-3-(4-nitro-naphthalen-1-yl)-propionic acid 2-trimethylsilanyl-ethyl ester To a mixture of 2-methoxycarbonylamino-3-(4-nitro-naphthalen-1-yl)-propionic acid (0.35 g, 1.1 mmol), pyridine (0.78 mL) and 2-trimethylsilylethanol (0.18 mL, 1.25 mmol, 1.1 eq) in acetonitrile (1.1 mL) cooled in an ice bath was added dicyclohexylcarbodiimide (0.25 g, 1.21 mmol). The mixture was stirred cold for 1 hour, placed in the refrigerator for 14 hours. The reaction mixture was filtered, concentrated under reduced pressure and purified on silica gel eluting with heptane/ethyl acetate (4:1) to provide the titled compound. MS ESI(−)) m/e 417 (M−H)$^-$.

EXAMPLE 7E 3-(4-amino-naphthalen-1-yl)-2-methoxycarbonylamino-propionic acid 2-trimethylsilanyl-ethyl ester A mixture of 2-methoxycarbonylamino-3-(4-nitro-naphthalen-1-yl)-propionic acid 2-trimethylsilanyl-ethyl ester (1.1 g, 2.64 mmol), 10% palladium on C (0.056 g) in methanol (5 mL) was stirred under an atmosphere of hydrogen for 4 hours. The mixture was filtered through diatomaceous earth and the filter cake washed with methanol (2×25 mL). The combined methanol was concentrated under reduced pressure to provide the titled compound. MS (ESI(+)) m/e 389 (M+H)$^+$.

EXAMPLE 7F

2-{4-[2-methoxycarbonylamino-2-(2-trimethylsilanyl-ethoxycarbonyl)-ethyl]-naphthalen-1-ylamino}-benzoic acid A mixture of 3-(4-amino-naphthalen-1-yl)-2-methoxycarbonylamino-propionic acid 2-trimethylsilanyl-ethyl ester (0.93 g, 2.40 mmol), diphenyliodonium-2-carboxylate (1.22 g, 3.8 mmol, 1.5 eq) and copper(II) acetate (25 mg, 0.14 mmol, 0.06 eq) in N,N-dimethylformamide (25 mL) was heated to 100° C. for 14 hours, then cooled to room temperature. The mixture was acidified to a pH <3 with 1N HCl, extracted with ethyl acetate (3×35 mL). The combined organic layers were washed with 1N HCl (1×25 mL), water (1×25 mL), brine (1×25 mL), and dried (MgSO$_4$), filtered and concentrated under reduced pressure. The residue was purified on silica gel eluting with 4:1 toluene/ethyl acetate to provide the titled compound. MS ESI(−)) m/e 507 (M−H)$^-$.

EXAMPLE 7G 2-(tert-butoxyoxalyl-{4-[2-methoxycarbonylamino-2-(2-trimethylsilanyl-ethoxycarbonyl)-ethyl]-naphthalen-1-yl}-amino)-benzoic acid To a mixture of 2-{4-[2-methoxycarbonylamino-2-(2-trimethylsilanyl-ethoxycarbonyl)-ethyl]-naphthalen-1-ylamino}-benzoic acid (0.7 g, 1.38 mmol) and diisopropylethylamine (0.57 mL) in methylene chloride (8 mL) at 0° C. was slowly added tert-butyl oxalyl chloride (538 mg, 3.61 mmol, 2.6 eq). The reaction was allowed to warm to room temperature over 1 hour and 4-(dimethylamino)pyridine (10 mg, 0.08 mmol, 0.06 eq) was added. The reaction was stirred for 14 hours, acidified to a pH <3 with 1N HCl, extracted with ethyl acetate (3×30 mL). The organic layer was washed with 1N HCl (2×30 mL), water (1×20 mL), and brine (1×20 mL), dried (MgSO$_4$), filtered and concentrated. The residue was purified on silica gel eluting with toluene/ethyl acetate (10:1) to provide the titled product. MS (APCI(+)) m/e 637 (M+H)$^+$.

EXAMPLE 7H 2-(tert-butoxyoxalyl-{4-[2-methoxycarbonylamino-2-(2-trimethylsilanyl-ethoxycarbonyl)-ethyl]-naphthalen-1-yl}-amino)-benzoic acid benzhydryl ester Diphenyldiazomethane was prepared according to the procedure described in *J. Org. Chem.* 1959, 24, 560, Miller, J. B.

To a mixture of 2-(tert-butoxyoxalyl-{4-[2-methoxycarbonylamino-2-(2-trimethylsilanyl-ethoxycarbonyl)-ethyl]-naphthalen-1-yl}-amino)-benzoic acid (0.3 g, 0.47 mmol) in acetone (3 mL) was added diphenyldiazomethane (134 mg, 0.69 mmol). The reaction mixture was stirred for 6 hours, acidified to a pH <3 with 1N HCl and extracted with ethyl acetate (3×20 mL). The organic layer was washed with 1N HCl (1×20 mL), water (2×15 mL), brine (1×30 mL), dried (MgSO$_4$), filtered and concentrated under reduced pressure. The concentrate was purified on silica gel eluting with 10:1 toluene/ethyl acetate to provide the titled product. MS (ESI(+)) m/e 820 (M+H$_2$O+H)$^+$

EXAMPLE 7I

2-{tert-butoxyoxalyl-[4-(2-carboxy-2-methoxycarbonylamino-ethyl)-naphthalen-1-yl]-amino}-benzoic acid benzhydryl ester To 2-(tert-butoxyoxalyl-{4-[2-methoxycarbonylamino-2-(2-trimethylsilanyl-ethoxycarbonyl)-ethyl]-naphthalen-1-yl}-amino)-benzoic acid benzhydryl ester (0.7 g, 0.87 mmol) in tetrahydrofuran (2.5 mL) cooled in an ice bath was added Tetrabutylammonium fluoride (1.5 mL, 1M in tetrahydrofuran). The mixture was stirred at 0° C. for 1 hour, ambient temperature for 1 hour, diluted with 1N HCl (40 mL) and extracted with methylene chloride (3×30 mL). The combined organic layers were washed with 1N HCl (2×20 mL), water (1×20 mL), brine (2×20 mL), dried (MgSO$_4$), filtered and concentrated under reduced pressure. The residue was purified on silica gel eluting with 10:1 toluene/ethyl acetate to provide the titled product. MS (ESI(+)) m/e 720 (M+H$_2$O+H)$^+$.

EXAMPLE 7J methyl N-{5-[(tert-butoxycarbonyl)amino]pentanoyl}-S-methyl-L-cysteinate A mixture of N-Boc aminovaleric acid (2.5 g, 11.5 mmol), methionine methyl ester hydrochloride (2.8 g, 13.8 mmol), HOBT (2.3 g, 13.8 mmol) in 30 mL of DMF was stirred at r.t. EDCI (3.1 g, 16.1 mmol) was added, followed by addition of Et$_3$N till the pH of the mixture reaches 6. After stirring at r.t for 2 hours, the reaction was quenched with water, extracted with EtOAc (2×30 mL). The combined organic layer was washed with sat. NaHCO$_3$ and brine, dried over sodium sulfate and concentrated in vacuo. The resulting oil (4.57 g) was used without any further purification.

EXAMPLE 7K methyl N-(5-aminopentanoyl)-S-methyl-L-cysteinate

The t-butyl carbamate from Example 7J was taken up in 4N HCl in dioxane and left at r.t. for 2 hours. The solvent was then removed under reduced pressure and the residue was evaporated with acetonitrile twice and pumped under high vacuum. The resulting amine hydrochloride salt was used directly for the coupling.

EXAMPLE 7L methyl N-(5-{[3-(4-{{2-[(benzhydryloxy)carbonyl]phenyl}[tert-butoxy(oxo)acetyl]amino}-1-naphthyl)-N-(methoxycarbonyl)alanyl]amino}pentanoyl)-L-methioninate The titled compound was prepared according to the procedure described in Example 1K, substituting the acid from Example 1J with the acid from Example 7I, and H-TYR(TBU)-OTBU HCL with the amine from Example 7K.

EXAMPLE 7M

N-(5-{[3-(4-[(carboxycarbonyl)(2-carboxyphenyl)amino]-1-naphthyl)-N-(methoxycarbonyl)alanyl]amino}pentanoyl)-L-methionine The titled compound was prepared according to the procedure described in Example 1L, substituting the ester from Example 1K with the ester from Example 7L. MS (ESI+) m/e 711 (M+H)$^+$, $^1$H NMR (300 MHz, DMSO-d$_6$) 1.23–1.64 (m, 4H), 1.71–2.22 (m, 4H), 2.03 (s, 3H), 2.35–2.56 (m, 2H), 2.97–3.59 (m, 7H), 4.00–4.67 (m, 2H), 6.70–7.80 (m, 6H), 7.86 (d, J=6.3 Hz, 1H), 7.92–8.34 (m, 4H), 8.43 (d, J=9.3 Hz, 1H).

EXAMPLE 8

N-{5-[(N-acetyl-4-[(carboxycarbonyl)(2-carboxyphenyl)amino]-3-isopropylphenylalanyl)amino]pentanoyl}-L-methionine

EXAMPLE 8A methyl (2Z)-2-(acetylamino)-3-(4-amino-3-isopropylphenyl)acrylate The titled compound was prepared according to the method described in Example 1B substituting 2-acetylamino-acrylic acid methyl ester for 2-acetylamino-acrylic acid benzyl ester and 4-bromo-2-isopropylaniline for 4-bromo-2-ethylaniline.

EXAMPLE 8B methyl N-acetyl-4-amino-3-isopropylphenylalaninate methyl (2Z)-2-(acetylamino)-3-(4-amino-3-isopropylphenyl)acrylate (752 mg, 2.72 mmole) and 10% Pd/C (143 mg) stirred in ethanol (20 mL) under 1 atmosphere of hydrogen for 16 hours. The mixture was filtered through Celite and the filtrate was concentrated under reduced pressure to provide the titled compound.

EXAMPLE 8C methyl N-{5-[(N-acetyl-4-amino-3-isopropylphenylalanyl)amino] pentanoyl}methioninate A mixture of methyl N-acetyl-4-amino-3-isopropylphenylalaninate in 1N NaOH (4 mL) and methanol (2 mL) was stirred for 5 hours, concentrated under reduced pressure, taken up in a mixture of ethyl acetate and ethanol (3×30 mL, 1:1), dried ($Na_2SO_4$), filtered and concentrated under reduced pressure. MS (ESI) m/z=−263 (M−H)⁻. To a mixture of the residue (239 mg, 0.833 mmole), 2-(5-amino-pentanoylamino)-4-methylsulfanyl-butyric acid methyl ester (298 mg, 1.0 mmole), 1-[3-(dimethylamino)propyl]-3-ethylcarbodiimide hydrochloride (240 mg, 1.25 mmole) and N-hydroxybenzotriazole (169 mg, 1.25 mmole) in DMF (3 mL) was added triethyl amine (116 $\mu$L) and the mixture was stirred for 16 hours. The mixture was diluted with water and extracted with ethyl acetate (2×25 mL) then with chloroform (2×25 mL). The combined organics were dried ($MgSO_4$), filtered, concentrated under reduced pressure and purified on silica gel eluting with 30% methanol/ethyl acetate to provide the titled compound (316 mg). MS (ESI) m/z=+509(M+H)⁺, 531 (M+Na)⁺.

EXAMPLE 8D methyl N-{5-[(N-acetyl-4-(2-carboxyphenyl)amino-3-isopropylphenylalanyl)amino] pentanoyl}methioninate The titled compound was prepared according to the method described in Example 7F by substituting methyl N-{5-[(N-acetyl-4-amino-3-isopropylphenylalanyl)amino] pentanoyl}methioninate for 2-methoxycarbonylamino-3-(4-nitro-naphthalen-1-yl)-propionic acid 2-trimethylsilanyl-ethyl ester.

EXAMPLE 8E

N-{5-[(N-acetyl-4-[(carboxycarbonyl)(2-carboxyphenyl)amino]-3-isopropylphenylalanyl) amino]pentanoyl}-L-methionine To a mixture of methyl N-{5-[(N-acetyl-4-(2-carboxyphenyl)amino-3-isopropylphenylalanyl)amino] pentanoyl}methioninate (78.7 mg, 0.125 mmole) and diisopropylethyl amine (54.5 $\mu$L, 0.313 mmole) in dichloromethane (20 mL) at 0° C. was added ethyl oxalyl chloride (35.0 $\mu$L, 0.313 mole) and DMF (20 $\mu$L). The mixture was stirred for 4 hours, poured into water and methanol (35 mL, 1:1) and concentrated under reduced pressure. The residue was dissolved in ethanol (3 mL), treated with 1 N NaOH (3 mL) and stirred for 1 hour. The mixture was adjusted to a pH=2 with trifluoroacetic acid and purified by reverse-phase HPLC (0% to 70% acetonitrile/aqueous 0.1% trifluoroacetic acid to provide the title compound. ¹H NMR (400 MHz, DMSO-d₆) δ 6.8–8.2 (m, 6H), 4.25–4.5 (br m, 2H), 3.04–3.2 (m, 5H), 2.15–2.25 (m, 6H), 2.02 (s, 3H), 1.05–2.0 (m, 7H), 0.90 (t, 6H); MS (ESI) m/z=−685 (M−H)⁻.

EXAMPLE 9

N-{5-[(N-acetyl-4-[(carboxycarbonyl)(2-carboxy-5-chlorophenyl)amino]-3-ethylphenylalanyl)amino] pentanoyl}-L-methionine

EXAMPLE 9A

Diphenyliodonium-4-chloro-2-carboxylate

A mixture of 2-iodo-4-chlorobenzoic acid (11.3 g, 40.0 mmol) in concentrated sulfuric acid (40 mL) was stirred at ambient temperature for 30 minutes, and then cooled to 10° C. $K_2S_2O_8$ (20.0 g, 75 mmol) was added portion-wise. The reaction mixture was kept at 10° C. for 20 minutes, benzene (35 mL) was added, and the mixture stirred at ambient temperature for 16 hours. The mixture was poured into ice, and potassium iodide (20 g) was added to the suspension. The solid was collected, washed with water, added to 5 N NaOH (100 mL), stirred for 30 minutes and filtered to provide titled compound (13 g). MS (ESI(+)) m/e 358, 360 (M+H)⁺; ¹H NMR (300 MHz, DMSO-d₆) δ 8.24 (d, 2H), 8.10 (d, 1H), 7.87–7.80 (m, 1H), 7.70–7.63 (m, 3H), 6.52 (d, 1H).

EXAMPLE 9B

2-{4-[2-(acetylamino)-3-(allyloxy)-3-oxopropyl] [tert-butoxy(oxo)acetyl]-2-ethylanilino}-4-chlorobenzoic acid The titled compound was prepared according to the method described in Example 7 F-G by substituting 2-acetylamino-3-(4-amino-3-ethyl-phenyl)-propionic acid allyl ester for 3-(4-amino-naphthalen-1-yl)-2-methoxycarbonylamino-propionic acid 2-trimethylsilanyl-ethyl ester and diphenyliodonium-5-chloro-2-carboxylate for diphenyliodonium-2-carboxylate.

EXAMPLE 9C (2S)-2-[(5-{[2-(acetylamino)-3-(4-[(carboxycarbonyl)(2-carboxy4-chlorophenyl) amino]-3-ethylphenyl)propanoyl]amino}pentanoyl) amino]-4-(methylsulfanyl)butanoic acid The titled compound was prepared according to the procedure described in Example 1F-L, substituting Example 9B for Example 1E and H-MET-OTBU HCL for H-TYR (TBU)-OTBU HCL. MS (ESI(+)) m/e 707, 708 (M+H)⁺; ¹H NMR (500 MHz, DMSO-d₆) δ 8.12–8.03 (m, 2H), 7.95–7.77 (m, 2H), 7.52–6.72 (m, 5H), 4.52–4.42 (m, 1H), 4.32–4.26 (m, 1H), 3.07–2.41 (m, 6H), 2.15–2.07 (m, 2H), 2.03 (s, 3H), 1.98–1.79 (m, 2H), 1.78, 1.75 (s, s, 3H), 1.50–1.42 (m, 2H), 1.40–1.30 (m, 2H), 1.28–0.91 (m, 3H).

EXAMPLE 10

N-(5-{[N-acetyl-4-[(carboxycarbonyl)(2-carboxyphenyl)amino]-3-(2-hydroxyethyl) phenylalanyl]amino}pentanoyl)-L-methionine

EXAMPLE 10A 2-(2-amino-5-bromo-phenyl)-ethanol

To a solution of 2-aminophenethyl alcohol (10.0 g, 72.9 mmol) in acetic acid (60 mL) at 10° C. was added $Br_2$ (3.8 mL, 72.9 mmol) in acetic acid (5 mL). Additional acetic acid (30 mL) was added and the reaction was stirred for 1 hour. The mixture was filtered and the filter cake washed with diethyl ether. The solid was then partitioned between ethyl acetate and aqueous 3N NaOH. The organic layer was washed with brine, dried ($Na_2SO_4$), filtered and concentrated under reduced pressure to provide the titled compound (15.8 g).

EXAMPLE 10B 4-bromo-2-(1-methyl-1-trimethylsilanyl-ethoxymethyl)-phenylamine To a solution of 2-(2-amino-5-bromo-phenyl)-ethanol (15.8 g, 72.8 mmol) in anhydrous N,N-dimethylformamide (50 mL) was added imidazole (6.0 g, 88.1 mmol) and tert-butyl dimethylsilyl chloride (12.0 g, 79.6 mmol) sequentially. The resulting mixture was stirred at ambient temperature for 1.5 hour, partitioned between water and ethyl acetate. The organic layer was washed with water, brine, dried ($Na_2SO_4$), filtered, concentrated under reduced pressure and purified on silica gel with 10–15% ethyl acetate/hexanes to provide the titled compound (15.0 g, 62.3%). MS (ESI+) m/e 330, 332 $(M+H)^+$.

EXAMPLE 10C 2-acetylamino-3-[4-amino-3-(2-hydroxy-ethyl)-phenyl]-propionic acid The titled compound was prepared according to the procedure described in Example 1B-C, substituting 4-bromo-2-(1-methyl-1-trimethylsilanyl-ethoxymethyl)-phenylamine for the 4-bromo-2-ethylalanine. The silyl protecting group came off during the hydrogenation process. MS (ESI+) m/e 381 $(M+H)^+$.

EXAMPLE 10D methyl-[5-{[N-acetyl-4-amino-3-(2-hydroxyethyl) phenylalanyl]oxy}pentanoyl]-S-methyl-L-cysteinate A solution of 2-acetylamino-3-[4-amino-3-(2-hydroxy-ethyl)-phenyl]-propionic acid (297 mg, 1.11 mmol), N-cyclohexylccarbodiimide-N'-methyl polystyrene HL resin (Nova Biochem; f=1.52 mmol/g, 1.47 g, 2.22 mmol), HOBT (200 mg, 1.22 mmol) in N,N-dimethylacetamide/$CH_2Cl_2$ (6 mL, 2:1) was stirred for 15 min, then methyl N-(5-aminopentanoyl)-S-methyl-L-cysteinate (400 mg, 1.32 mmol) (pre-neutralized with 188 μL of $Et_3N$) in N,N-dimethylacetamide/$CH_2Cl_2$ (4 mL, 2:1) was added. The resulting mixture was stirred at ambient temperature for 24 hours. Tris-(2-aminoethyl)-amine polystyrene HL resin (Nova Biochem, f=4.06 mmol/g, 0.42 g, 1.65 mmol) was added, the mixture was stirred for 2 hours, and then filtered through the celite, the solvent was removed under reduced pressure and the residue was purified on a Gilson preparative HPLC to provide the titled compound (383 mg, 67%). MS (ESI+) m/e 511 $(M+H)^+$.

EXAMPLE 10E methyl-[5-{[N-acetyl-2-(ethyl ethyl oxalate)-4-[(ethoxycarboxycarbonyl)(2-carboxyphenyl)amino]-3-(2-hydroxyethyl)phenylalanyl]oxy}pentanoyl]-S-methyl-L-cysteinate The titled compound was prepared according to the procedures described in Example 7F-G, substituting methyl-[5-{[N-acetyl-4-amino-3-(2-hydroxyethyl)phenylalanyl] oxy}pentanoyl]-S-methyl-L-cysteinate for 3-(4-amino-naphthalen-1-yl)-2-methoxycarbonylamino-propionic acid 2-trimethylsilanyl-ethyl ester, and ethyl oxalyl chloride for the t-butyl oxalyl chloride.

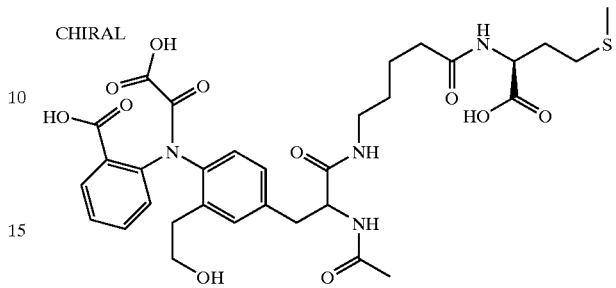

EXAMPLE 10F

N-(5-{[N-acetyl-4-[(carboxycarbonyl)(2-carboxyphenyl)amino]-3-(2-hydroxyethyl) phenylalanyl]amino}pentanoyl)-L-methionine To a stirred solution of methyl-[5-{[N-acetyl-2-(ethyl ethyl oxalate)-4-[(ethoxycarboxycarbonyl)(2-carboxyphenyl)amino]-3-(2-hydroxyethyl)phenylalanyl] oxy}pentanoyl]-S-methyl-L-cysteinate (300 mg, 0.36 mmol) in MeOH (5 mL) was added 3N NaOH (0.96 mL, 2.88 mmol). The resulting mixture was stirred at ambient temperature for 4 hours, the mixture was acidified to a pH=3 with concentrated HCl (12 M) and purified on a Gilson prep. HPLC to provide the titled compound as a light brown foam (105 mg, 0.15 mmol, 42%). MS (ESI+) m/e 687 $(M–H)^–$, $^1H$ NMR (300 MHz, DMSO-$d_6$) 1.25–1.57 (m, 4H), 1.70–2.15 (m, 4H), 2.03 and 2.07 (s, 3H in total), 2.31–2.53 (m, 2H), 2.58–3.14 (m, 4H), 3.50–4.00 (overlapping m, 2H), 4.23–4.34 (m, 1H), 4.35–4.55 (m, 1H), 6.79 (dd, J=3.9, 8.1 Hz, 1H), 7.00–7.59 (m, 5H), 7.79–8.16 (m, 4H).

EXAMPLE 11

N-{[4-({[N-acetyl-4-[(carboxycarbonyl)(2-carboxyphenyl)amino]-3-(2-hydroxyethyl) phenylalanyl]amino}methyl)cyclohexyl]carbonyl}-L-norleucine

EXAMPLE 11A 4-({[(benzyloxy)carbonyl]amino}methyl) cyclohexanecarboxylic acid The titled compound was prepared according to the procedure described in J. Med. Chem. 1998, 41, 74–95; Curtin, M. L.; Davidsen, S. K.; Heyman, H. et al.

EXAMPLE 11B methyl N-{[4-({[(benzyloxy)carbonyl] amino}methyl)cyclohexyl]carbonyl}-L-norleucinate To a stirring mixture of 4-({[(benzyloxy)carbonyl] amino}methyl)cyclohexanecarboxylic acid (750 mg, 2.57 mmol), TBTU (1.08 g, 3.34 mmol), and HOBT (55 mg, 0.03 mmol) in DMF (15 mL) was added the norleucine OMe HCl (411 mg, 2.83 mmol), followed by addition of triethylamine (898 μL, 6.43 mmol). The resulting mixture was then stirred at ambient temperature for 2 hours, diluted with water and the resulting precipitate was collected by filtration and dried in a vacuum oven to provide the titled compound (830 mg, 1.98 mmol, 77%).

EXAMPLE 11C methyl N-{[4-(aminomethyl)cyclohexyl]carbonyl}-L-norleucinate

A mixture of methyl N-{[4-({[(benzyloxy)carbonyl] amino}methyl)cyclohexyl]carbonyl}-L-norleucinate (830 mg, 1.98 mmol), 10% palladium on C (0.056 g) in methanol (10 mL) was stirred under an atmosphere of hydrogen for 4 hours. The mixture was filtered through diatomaceous earth and the filter cake washed with methanol (2×15 mL). The combined methanol was concentrated under reduced pressure to provide the titled compound as a colorless solid.

EXAMPLE 11D

N-{[4-({[N-acetyl-4-[(carboxycarbonyl)(2-carboxyphenyl)amino]-3-(2-hydroxyethyl) phenylalanyl]amino}methyl)cyclohexyl]carbonyl}-L-norleucine The titled compound was prepared according to the procedures described in Example 10D-F, substituting amine from Example 11C for the amine from Example 7K. MS (ESI+) m/e 711 (M+H)$^+$, $^1$H NMR (300 MHz, DMSO-d$_6$) 0.74–0.92 (m, 5H), 1.17–1.40 (m, 8H), 1.50–1.81 (m, 9H), 2.00–2.30 (m, 2H), 2.55–3.05 (m, 4H), 3.80–4.75 (m, 4H), 6.79 (dd, J=3.9, 8.1 Hz, 1H), 7.00–7.59 (m, 5H), 7.79–8.16 (m, 4H).

EXAMPLE 12 methyl 2-[4-({N-[(allyloxy)carbonyl]-4-[(carboxycarbonyl)(2-carboxyphenyl)amino]-L-phenylalanyl}amino)butoxy]-6-hydroxybenzoate

EXAMPLE 12A methyl 2-{4-[(tert-butoxycarbonyl)amino]butoxy}-6-hydroxybenzoate To a round bottom flask was charged with tert-butyl 4-hydroxybutylcarbamate (400 mg, 2.1 mmol), 463 mg of 2,6-dihydroxybenzoate (463 mg, 2.7 mmol), and triphenylphosphine (777 mg, 3.0 mmol). The flask was vacuumed and back flushed with nitrogen (3×), capped with a rubber septum, and kept under positive nitrogen atmosphere. THF (anhydrous) was then added, followed by dropwise addition of DEAD (433 µL, 2.7 mmol). Most of the starting material was consumed within the first 30 min. Solvent was then removed in vacuo, and the residue was purified on a silica gel chromatography eluting with 15–30% EtOAc in hexane to give the ether product (410 mg, 57%) as a cloroless oil.

EXAMPLE 12B methyl 2-(4-aminobutoxy)-6-hydroxybenzoate

Methyl 2-{4-[(tert-butoxycarbonyl)amino]butoxy}-6-hydroxybenzoate (410 mg, 1.2 mmol) was treated with trifluoroacetic acid/dichloromethane (6 mL, 1:1/v:v) at ambient temperature for 3 hours, concentrated under reduced pressure and evaporated with acetonitrile twice to provide the titled amine as its trifluoroacetic acid salt (450 mg).

EXAMPLE 12C 2-(trimethylsilyl)ethyl 4-[(2-carboxyphenyl)amino]-N-(tert-butoxycarbonyl)-L-phenylalaninate The titled compound was prepared according to the procedure described for Example 7D-F, substituting p-nitro N-Boc phenyl alanine for 2-methoxycarbonylamino-3-(4-nitro-naphthalen -1-yl)-propionic acid.

EXAMPLE 12D 2-(trimethylsilyl)ethyl 4-[(2-carboxyphenyl)amino]-L-phenylalaninate 2-(trimethylsilyl)ethyl 4-[(2-carboxyphenyl)amino]-N-(tert-butoxycarbonyl)-L-phenylalaninate (6.97 g, 13.9 mmol) was treated with 4N HCl (13.9 mL) in Dioxane (55.8 mmol) for one hour. The solvent was then removed under reduced pressure. The residue was precipitated with diethyl ether (2×35 mL) to provide the titled compound as a light yellow solid (6.1 g, 100%).

EXAMPLE 12E 2-(trimethylsilyl)ethyl N-[(allyloxy)carbonyl]-4-[(2-carboxyphenyl)amino]-L-phenylalaninate The titled compound was prepared according to the procedure described for Example 7C, substituting 2-(trimethylsilyl)ethyl 4-[(2-carboxyphenyl)amino]-L-phenylalaninate for 3-(4-nitro-1-naphthyl)alanine, and allyl chloroformate for methylchloroformate.

EXAMPLE 12F

N-[(allyloxy)carbonyl]-4-{{2-[(benzhydryloxy) carbonyl]phenyl}[tert-butoxy(oxo)acetyl]amino}-L-phenylalanine The titled compound was prepared according to the procedure described for Example 7G-I, substituting 2-(trimethylsilyl)ethyl N-[(allyloxy)carbonyl]-4-[(2-carboxyphenyl)amino]-L-phenylalaninate for 2-{4-[2-methoxycarbonylamino-2-(2-trimethylsilanyl-ethoxycarbonyl)-ethyl]-naphthalen-1-ylamino}-benzoic acid.

EXAMPLE 12G methyl 2-{4-[(N-[(allyloxy)carbonyl]-4-{{2-[(benzhydryloxy)carbonyl]phenyl}[tert-butoxy(oxo) acetyl]amino}-L-phenylalanyl)amino]butoxy}-6-hydroxybenzoate To a stirring mixture of N-[(allyloxy)carbonyl]-4-{{2-[(benzhydryloxy)carbonyl]phenyl}[tert-butoxy(oxo)acetyl] amino}-L-phenylalanine (100 mg, 0.147 mmol), TBTU (67 mg, 0.206 mmol), and HOBT (3 mg, 0.02 mmol) in DMF (2 mL) was added methyl 2-(4-aminobutoxy)-6-hydroxybenzoate, followed by addition of triethylamine (75 µL, 0.53 mmol). The resulting mixture was then stirred at ambient temperature for 2 hours, diluted with the addition of water. The crude product was extracted with ethyl acetate (2×10 mL). The combined organic layer were washed with aqueous NaHCO$_3$ (2×25 mL) and brine (2×25 mL), dried (Na$_2$SO$_4$), filtered and concentrated under reduced pressure. The resulting residue was purified on an AllTech sep-pak to provide the titled compound (89 mg, 68%).

EXAMPLE 12H methyl 2-[4-({N-[(allyloxy)carbonyl]-4-[(carboxycarbonyl)(2-carboxyphenyl)amino]-L-phenylalanyl}amino)butoxy]-6-hydroxybenzoate A mixture methyl 2-{4-[(N-[(allyloxy)carbonyl]-4-{{2-[(benzhydryloxy)carbonyl]phenyl}[tert-butoxy(oxo)acetyl]

amino}-L-phenylalanyl)amino]butoxy}-6-hydroxybenzoate (89 mg, 0.10 mmol), 20 mg of resorcinol, and trifluoroacetic acid (1.5 mL) in methylene chloride (2.0 mL) was stirred for 5 hours, concentrated under reduced pressure. The crude product was purified on a Gilson preparative HPLC to provide the titled compound as a white powder (35 mg, 0.052 mmol, 52%). MS (ESI+) m/e 678 (M+H)+, $^1$H NMR (300 MHz, DMSO-$d_6$) 1.40–1.66 (m, 4H), 2.68–2.83 (m, 1H), 2.83–2.98 (m, 1H), 2.98–3.15 (m, 2H), 3.72 (s, 3H), 3.90 (t, J=5.85 Hz, 1H), 4.09–4.12 (m, 1H), 4.33–4.41 (m, 2H), 5.08 (d, J=10.8 Hz, 1H), 5.18 (d, J=18.0 Hz, 1H), 5.70–5.90 (m, 1H), 6.47 (d, J=8.7 Hz, 1H), 7.25 (d, J=8.7 Hz, 1H), 7.29 (d, J=8.7 Hz, 1H), 7.36 (d, J=8.7 Hz, 1H), 7.38–7.66 (m, 3H), 7.93–8.03 (m, 2H), 9.92 (s, 1H).

EXAMPLE 13 methyl 2-{4-[(N-acetyl-4-[(carboxycarbonyl)(2-carboxyphenyl)amino]-3-ethylphenylalanyl)amino]butoxy}-6-hydroxybenzoate

EXAMPLE 13A

N-acetyl-4-{2-[(benzhydryloxy)carbonyl][(benzyloxy)(oxo)acetyl]anilino}-3-ethylphenylalanine The titled compound was prepared according to the procedure described for Example 1G, substituting the benzyl oxalyl chloride for tert-butyl oxalyl chloride.

EXAMPLE 13B methyl 2-[(5-{[2-(acetylamino)-3-(4-{2-[(benzhydryloxy)carbonyl][(benzyloxy)(oxo)acetyl]anilino}-3-ethylphenyl)propanoyl]amino}pentyl)oxy]-6-hydroxybenzoate Methyl 2-(4-aminobutoxy)-6-hydroxybenzoate (42 mg, 0.12 mmol), N-acetyl-4-{2-[(benzhydryloxy)carbonyl][(benzyloxy)(oxo)acetyl]anilino}-3-ethylphenylalanine (70 mg, 0.1 mmol), 2-(1H-benzotriazole-1-yl)-1,1,3,3-tetramethyluronium tetrafluoroborate (32 mg, 0.1 mmol) and diisopropylethylamine (70 µL, 0.4 mmol) in N,N-dimethylformamide (1 mL) was stirred at ambient temperature overnight, diluted with ethyl acetate and washed with aqueous NaHCO$_3$ (1×30 mL), brine (2×30 mL), dried (MgSO$_4$), filtered and concentrate under reduced pressure. The residue was purified on silica gel eluting with ethyl acetate to provide of titled compound 54 mg.

EXAMPLE 13C

2-[4-[2-(acetylamino)-3-({4-[3-hydroxy-2-(methoxycarbonyl)phenoxy]butyl}amino)-3-oxopropyl](carboxycarbonyl)-2-ethylanilino]benzoic acid Methyl 2-[(5-{[2-(acetylamino)-3-(4-{2-[(benzhydryloxy)carbonyl][(benzyloxy)(oxo)acetyl]anilino}-3-ethylphenyl)propanoyl]amino}pentyl)oxy]-6-hydroxybenzoate and 10% Pd—C (5 mg) in methanol (3 mL) was stirred under an atmosphere of hydrogen at ambient temperature overnight to provide the tilted compound 33 mg. MS (ESI(+)) m/e 664 (M+H)+; $^1$H NMR (500 MHz, DMSO-$d_6$) 9.90 (s, 1H), 8.13–7.78 (m, 3H), 7.58–6.75 (m, 7H), 6.47 (d, 2H), 4.53–4.40 (m, 1H), 3.95–3.85 (m, 2H), 3.72 (s, 3H), 3.10–2.56 (m, 6H), 1.78, 1.75 (s, s, 3H), 1.62–1.52 (m, 2H), 1.50–1.40 (m, 2H), 1.26–0.91 (m, 3H).

EXAMPLE 14 methyl 2-{2-[2-({N-[(allyloxy)carbonyl]-4-[(carboxycarbonyl)(2-carboxyphenyl)amino]-L-phenylalanyl}amino)ethoxy]ethoxy}-6-hydroxybenzoate The titled compound was prepared according to the procedure described for Example 12A-B and Example 12G-H, substituting [2-(2-Hydroxy-ethoxy)-ethyl]-carbamic acid tert-butyl ester for tert-butyl 4-hydroxybutylcarbamate. MS (ESI+) m/e 694 (M+H)+, $^1$H NMR (300 MHz, DMSO-$d_6$) 2.61–2.83 (m, 2H), 2.83–2.99 (m, 2H), 3.15–3.28 (m, 2H), 3.38–3.51 (m, 2H), 3.67–3.73 (m, 2H), 3.76 (s, 3H), 3.98–4.09 (m, 2H), 4.09–4.24 (m, 1H), 4.28–4.42 (m, 2H), 5.06 (d, J=10.8 Hz, 1H), 5.16 (d, J=17.4 Hz, 1H), 5.63–5.88 (m, 1H), 6.53 (d, J=8.7 Hz, 1H), 6.77 (d, J=8.7 Hz, 1H), 7.10–7.66 (m, 7H), 7.85 and 7.93 (d, J=8.7 Hz, 1H in total), 8.03 (t, J=5.25 Hz, 1H), 10.19 (s, 1H).

EXAMPLE 15 methyl 2-[(5-{[N-acetyl-3-(4-[(carboxycarbonyl)(2-carboxyphenyl)amino]-1-naphthyl)-L-alanyl]amino}pentyl)oxy]-6-hydroxy-4-methylbenzoate

EXAMPLE 15A methyl 3-(4-amino-1-naphthyl)-N-(tert-butoxycarbonyl)-L-alaninate A mixture of (S)-3-iodo-N-tert-butoxycarbonylalanine methyl ester (6.58 g, 20.0 mmol) and zinc dust (7.5 g, 119 mmol) in DMF (20 mL) under an atmosphere of N$_2$ was heated to 60° C. for 5 minutes then allowed to cool and settle in order to facilitate transfer of the organozinc reagent.

A solution of 4-bromo-1-naphthylamine (4.44 g, 20.0 mmol), tri-o-tolylphosphine (1.16 g, 3.81 mmol), and palladium(II)acetate (220 mg, 0.980 mmol) in DMF (10 mL) under N$_2$ was stirred for 30 minutes, then the solution of the organozinc reagent previously prepared was added via syringe. The mixture was heated at 60° C. for 1 hour, the mixture was poured into water (150 mL), and extracted with diethyl ether (3×50 mL). The combined organic layers were washed with water (1×50 mL), brine (1×25 mL), dried (MgSO$_4$), filtered, and concentrated under reduced pressure to an oil. The oil was purified on silica gel, eluting with 30% to 40% ethyl acetate hexanes, to provide the titled compound (2.4 g, 35%).

EXAMPLE 15B 3-(4-amino-1-naphthyl)-N-(tert-butoxycarbonyl)-L-alanine

To a solution of methyl 3-(4-amino-1-naphthyl)-N-(tert-butoxycarbonyl)-L-alaninate (2.4 g, 7.0 mmol) in methanol (10 mL) was added 8M aqueous NaOH (1.5 mL, 12 mmol) and the mixture was stirred at ambient temperature for 45 minutes. The mixture was concentrated under reduced pressure, taken up in water (5 mL) and extracted with diethyl ether (2×10 mL). The aqueous layer was then shaken with ethyl acetate (30 mL) and 1M HCl (13 mL). The layers were separated, and the aqueous layer was extracted with ethyl acetate (1×20 mL). The combined ethyl acetate layers were washed with brine (1×5 mL), dried (MgSO$_4$), filtered, and concentrated under reduced pressure to provide the titled compound (1.9 g, 83%).

EXAMPLE 15C 5-hydroxypentyl-[3-(4-amino-1-naphthyl)-N-(tert-butoxycarbonyl)]-L-alaninamide To a solution of 3-(4-amino-1-naphthyl)-N-(tert-butoxycarbonyl)-L-alanine (725 mg, 2.19 mmol) in DMF (5 mL) was added 1(3-(dimethylamino)propyl)-3-ethylcarbodiimide hydrochloride (1.75 g (9.12 mmol), 5-amino-1-pentanol (250 mg, 2.42 mmol), 3-hydroxy-1,2,3-benzotriazin-4(3H)-one (360 mg, 2.21 mmol) and triethylamine (500 µL, 3.59 mmol). The reaction was stirred at ambient temperature for 17 hours, concentrated under reduced pressure to a thick oil. The oil was taken up in aqueous $NaHCO_3$ solution (10 mL) and water (10 mL). The mixture was extracted with ethyl acetate, and the combined ethyl acetate layers dried ($MgSO_4$), filtered, and concentrated under reduced pressure. The residue was purified on silica gel, eluting with 95:5 ethyl acetate/methanol to provide the titled compound (535 mg, 59%).

EXAMPLE 15D 3-(4-amino-1-naphthyl)-$N^2$-(tert-butoxycarbonyl)-$N^1$-(5-{[tert-butyl(dimethyl)silyl]oxy}pentyl)-L-alaninamide To a solution of 5-hydroxypentyl-[3-(4-amino-1-naphthyl)-N-(tert-butoxycarbonyl)]-L-alaninamide (525 mg, 1.26 mmol) in DMF (3 mL) was added tert-butyldimethylsilyl chloride (256 mg, 1.70 mmol), and imidazole (154 mg, 2.26 mmol). The mixture was stirred at ambient temperature for 10 minutes, poured into water (15 mL) and extracted with diethyl ether (3×10 mL). The combined ether layers were washed with water (1×10 mL), brine (1×10 mL), dried ($MgSO_4$), filtered, and concentrated under reduced pressure to an oil. The oil was purified on silica gel, eluting with 40% ethyl acetate/hexanes to provide the titled compound (600 mg, 90%).

EXAMPLE 15E 3-(4-(benzhydryl 2-{[ethoxy(oxo)acetyl]amino}benzoate)-1-naphthyl)-$N^2$-(tert-butoxycarbonyl)-$N^1$-(5-{[tert-butyl(dimethyl)silyl]oxy}pentyl)-L-alaninamide To 3-(4-amino-1-naphthyl)-$N^2$-(tert-butoxycarbonyl)-$N^1$-(5-{[tert-butyl(dimethyl)silyl]oxy}pentyl)-L-alaninamide (600 mg, 1.13 mmol) was added diphenyliodonium-2-carboxylate monohydrate (460 mg, 1.35 mmol), copper(II) acetate (8 mg, 0.04 mmol) and 2-propanol (5 mL). The mixture was heated to reflux under an atmosphere of $N_2$ for 2 hours, cooled and concentrated under reduced pressure. The residue was taken up in 1M HCl (10 mL) and extracted with diethyl ether (3×10 mL). The combined ether layers was washed with brine (1×10 mL), dried ($MgSO_4$), filtered, and concentrated under reduced pressure.

To an ice cold solution of the residue in DMF (3 mL) was added triethylamine (450 µL, 3.53 mmol) and ethyl oxalyl chloride (200 µL, 2.07 mmol). The mixture was allowed to come to ambient temperature over 30 minutes and 8M $NH_4OH$ (6 mL) was added. To the mixture was added 1M HCl (10 mL) and then the aqueous suspension was extracted with diethyl ether (3×10 mL). The combined ether layers were washed with brine (1×10 mL), dried ($MgSO_4$), filtered, and concentrated under reduced pressure to a foam.

A solution of the foam in ethyl acetate (5 mL) and diphenyldiazomethane (240 mg, 1.23 mmol) was stirred for 24 hours, concentrated under reduced pressure and purified on silica gel eluting with 40% ethyl acetate/hexanes to provide the titled compound (354 mg, 34% overall).

EXAMPLE 15F 5-hydroxypentyl 3-(4-{{2-[(benzhydryloxy)carbonyl]phenyl}[ethoxy(oxo)acetyl]amino}-1-naphthyl)-N-(tert-butoxycarbonyl)-L-alaninamide To a solution of 3-(4-(benzhydryl 2-{[ethoxy(oxo)acetyl]amino}benzoate)-1-naphthyl)-$N^2$-(tert-butoxycarbonyl)-$N^1$-(5-{[tert-butyl(dimethyl)silyl]oxy}pentyl)-L-alaninamide (278 mg, 0.303 mmol) in THF (2 mL) was added tetrabutylammonium fluoride hydrate (108 mg, 0.404 mmol). The reaction was stirred at ambient temperature for 3 hours and concentrated under reduced pressure. The residue was taken up in water (5 mL) and extracted with ethyl acetate (2×5 mL). The combined ethyl acetate layers were washed with brine (1×1 mL), dried ($MgSO_4$), filtered, and concentrated under reduced pressure to an oil. The oil was purified on silica gel eluting with 40% ethyl acetate/hexanes to 100% ethyl acetate to provide the titled compound (170 mg, 70%).

EXAMPLE 15G methyl 2-[(5-{[N-acetyl-3-(4-[(carboxycarbonyl)(2-carboxyphenyl)amino]-1-naphthyl)-L-alanyl]amino}pentyl)oxy]-6-hydroxy-4-methylbenzoate To a reclosable pressure tube containing methyl 2,6-dihydroxy-4-methylbenzoate (10 mg, 0.055 mmol) was added a solution of 5-hydroxypentyl 3-(4-{{2-[(benzhydryloxy)carbonyl]phenyl}[ethoxy(oxo)acetyl]amino}-1-naphthyl)-N-(tert-butoxycarbonyl)-L-alaninamide (33 mg, 0.041 mmol) and triphenylphosphine (15 mg, 0.057 mmol) in THF (0.2 mL). Diethylazodicarboxylate (10 mL, 0.064 mmol) was added, the vessel sealed and the reaction was stirred for 30 minutes. The reaction was opened, diluted with several drops of hexanes (barely to the point of cloudiness), then purified on a prepacked silica gel column (5 mL) eluting with 50% ethyl acetate/hexanes to provide the desired compound as an oil.

To the oil was added $CH_2Cl_2$ (1 mL), three drops of anisole and trifluoroacetic acid (1 mL). The reaction was stirred for 5 minutes and concentrated under reduced pressure. The residue was taken up in 2M NaOH (1 mL), extracted with diethyl ether (1×1 mL). To the aqueous solution was added six drops of acetic anhydride and the reaction was swirled briefly. To the mixture was added five drops of 2M NaOH and purified by reverse phase HPLC eluting with 0% to 70% acetonitrile/0.1% aqueous trifluoroacetic acid to provide (3.6 mg, 12%) of the titled compound. $^1$H NMR (500 MHz, $d_6$-DMSO) mixture of rotamers, δ 9.95 (s, 1H), 8.27 (m, 2H), 8.18 (m, 1H), 7.95 (m, 1H), 7.61 (m, 2H), 7.46 (m, 1H), 7.40 (m, 1H), 7.31 (m, 3H), 6.55 (s, 1H), 6.33 (s, 1H), 6.29 (s, 1H), 4.55 (m, 1H), 3.85 (m, 2H), 3.71 (s, 3H), 3.01 (m, 1H), 2.21 (s, 3H), 2.07 (s, 3H), 1.76 (m, 3H), 1.56 (m, 2H), 1.26 (m, 6H); MS (ESI) m/z 714 $[M+H]^+$, 736 $[M+Na]^+$.

EXAMPLE 16 methyl 4-{4-[(N-acetyl-4-[(carboxycarbonyl)(2-carboxyphenyl)amino]-3-ethylphenylalanyl)amino]butoxy}-2-hydroxy-1,1'-biphenyl-3-carboxylate

EXAMPLE 16A methyl 3-bromo-2,6-dihydroxybenzoate

To a mixture of methyl-2,6-dihydroxybenzoate (1.68 g, 10.0 mmol) in dichloromethane (10 mL) was added acetic acid (1 mL), followed by drop-wise addition of bromine (515 µL, 10.0 mmol) in dichloromethane (5 mL). The reaction mixture was stirred at ambient temperature for 1 hour, concentrated under reduced pressure, co-evaporated with ethyl acetate (2×). The resulting solid was triturated with hexane/ethyl acetate and re-crystallized from hot hexane/ethyl acetate to provide the titled compound (1.45 g).

MS ESI(–,) m/e 244, 246 (M–H)+; 1H NMR (300 MHz, DMSO-d6) δ 10.45 (s, 1H), 10.19 (s, 1H), 7.46 (d, 1H), 6.41 (d, 1H), 3.84 (s, 3H).

EXAMPLE 16B methyl 3-bromo-6-{4-[(tert-butoxycarbonyl)amino] butoxy}-2-hydroxybenzoate The titled compound was prepared according to the procedure described for Example 12A, substituting the methyl 3-bromo-2,6-dihydroxybenzoate for 2,6-dihydroxybenzoate. MS (ESI(+) m/e 418, 420 (M+H)+; 1H NMR (300 MHz, DMSO-d6) δ 10.44 (s, 1H), 7.47 (d, 1H), 6.82 (t, 1H), 6.64 (d, 1H), 3.88 (t, 2H), 3.79 (s, 3H), 2.95 (q, 2H), 1.69–1.43 (m, 4H), 1.38 (s, 9H).

EXAMPLE 16C methyl 4-{4-[(tert-butoxycarbonyl)amino]butoxy}-2-hydroxy[1,1'-biphenyl]-3-carboxylate To a mixture of methyl 3-bromo-6-{4-[(tert-butoxycarbonyl)amino]butoxy}-2-hydroxybenzoate (56 mg, 0.134 mmol), tetrakis(triphenylphosphine) palladium (7 mg), 2M Na2CO3 (134 μL, 0.268 mmol) in toluene (1 mL) and ethanol (0.5 mL) was added phenylboronic acid (18 mg, 0.147 mmol). The reaction mixture was heated to 80° C. in a sealed tube overnight, taken up in ethyl acetate, washed with aqueous NaHCO3, dried (MgSO4), filtered and concentrated under reduced pressure. The residue was purified on silica gel with hexane/ethyl acetate to provide the titled compound (23 mg). MS (ESI(+)) m/e 416 (M+H)+.

EXAMPLE 16D methyl 4-(4-aminobutoxy)-2-hydroxy[1,1'-biphenyl]-3-carboxylate

The titled compound was prepared according to the procedure described for Example 12B, substituting methyl 4-{4-[(tert-butoxycarbonyl)amino]butoxy}-2-hydroxy[1,1'-biphenyl]-3-carboxylate for tert-butyl 4-hydroxybutylcarbamate.

EXAMPLE 16E

N-acetyl-4-{2-[(benzhydryloxy)carbonyl] [(benzyloxy)(oxo)acetyl]anilino}-3-ethylphenylalanine The titled compound was prepared according to the procedure described in Example 13B-C, substituting methyl 4-(4-aminobutoxy)-2-hydroxy [1,1'-biphenyl]-3-carboxylate for methyl 2-(4-aminobutoxy)-6-hydroxybenzoate. MS (ESI(+)) m/e 740(M+H)+; 1H NMR (500 MHz, DMSO-d6) 10.11 (s, 1H), 8.13–7.78 (m, 3H), 7.58–6.96 (m, 11H), 6.74 (d, 2H), 4.48–4.38 (m, 1H), 3.93 (s, 2H), 3.78 (s, 3H), 3.50–2.56 (m, 6H), 1.77, 1.75 (s, s, 3H), 1.25–0.91 (m, 7H).

EXAMPLE 17

2-[4-({N-acetyl-4-[(carboxycarbonyl)(2-carboxyphenyl)amino]-3-ethylphenylalanyl}amino) butoxy]-6-hydroxybenzoic acid

EXAMPLE 17A benzyl 2-(4-aminobutoxy)-6-hydroxybenzoate

The tilted compound was prepared according to the procedure described for Example 12A-B, substituting benzyl 2,6-dihydroxybenzoate for methyl 2,6-dihydroxybenzoate.

EXAMPLE 17B

2-[4-({N-acetyl-4-[(carboxycarbonyl)(2-carboxyphenyl)amino]-3-ethylphenylalanyl}amino) butoxy]-6-hydroxybenzoic acid The titled compound was prepared according to the procedure described in Example 13B-C, substituting benzyl 2-(4-aminobutoxy)-6-hydroxybenzoate for methyl 2-(4-aminobutoxy)-6-hydroxybenzoate. MS (ESI(+)) m/e 650 (M+H)+; 1H NMR (500 MHz, DMSO-d6) 10.33 (s, 1H), 8.13–7.78 (m, 3H), 7.58–6.75 (m, 7H), 6.47 (d, 2H), 4.53–4.40 (m, 1H), 3.93–3.85 (m, 2H), 3.10–2.56 (m, 6H), 1.78, 1.75 (s, s, 3H), 1.62–1.52 (m, 2H), 1.50–1.40 (m, 2H), 1.26–0.91 (m, 3H).

EXAMPLE 18

3-({5-[(N-acetyl-3-{4-[(carboxycarbonyl)(2-carboxyphenyl)amino]-1-naphthyl}-L-alanyl)amino] pentyl}oxy)-2-naphthoic acid The titled compound was prepared according to the procedure described in Example 15G, substituting 2-hydroxy-3-naphthoic acid methyl ester for methyl 2,6-dihydroxy-4-methylbenzoate. 1H NMR (500 MHz, d6-DMSO) mixture of rotamers, δ 8.45–8.42 (m, 1H), 8.35–8.30 (m, 1H), 8.26–8.21 (m, 1H), 8.18 (s, 1H), 8.06–7.95 (m, 2H), 7.92 (d, 1H, J=8.2 Hz), 7.84 (m, 2H), 7.67–7.47 (m, 5H), 7.17 (m, 1H), 6.83 (t, 1H, J=6.4 Hz), 4.70–4.58 (m, 1H), 4.07 (t, 1H, J=6.4 Hz), 4.03 (t, 1H, J=6.4 Hz), 3.59–2.99 (m, 4H), 2.07 (s, 3H), 1.80–1.63 (m, 4H), 1.39–1.16 (m, 5H); MS (ESI) m/z 720 [M+H]+, 742 [M+Na]+.

EXAMPLE 19 methyl 6-{4-[(N-acetyl-4-[(carboxycarbonyl)(2-carboxyphenyl)amino]-3-ethylphenylalanyl)amino] butoxy}-3-bromo-2-hydroxybenzoate

EXAMPLE 19A methyl 6-(4-aminobutoxy)-3-bromo-2-hydroxybenzoate

The tilted compound was prepared according to the procedure described for Example 12A-B, substituting 3-bromo-2,6-dihydroxybenzoate for 2,6-dihydroxybenzoate.

EXAMPLE 19B methyl 6-{4-[(N-acetyl-4-{{2-[(benzhydryloxy) carbonyl]phenyl}[(benzyloxy)(oxo)acetyl]amino}-3-ethylphenylalanyl)amino]butoxy}-3-bromo-2-hydroxybenzoate The titled compound was prepared according to the procedure described in Example 13B, substituting methyl 6-(4-aminobutoxy)-3-bromo-2-hydroxybenzoate for methyl 2-(4-aminobutoxy)-6-hydroxybenzoate.

EXAMPLE 19C methyl 6-{4-[(N-acetyl-4-[(carboxycarbonyl)(2-carboxyphenyl)amino]-3-ethylphenylalanyl)amino] butoxy}-3-bromo-2-hydroxybenzoate Methyl 6-{4-[(N-acetyl-4-{{2-[(benzhydryloxy) carbonyl]phenyl}[(benzyloxy)(oxo)acetyl]amino}-3- ethylphenylalanyl)amino]butoxy}-3-bromo-2-hydroxybenzoate was treated with trifluoroacetic acid (500 µL)/methylene chloride (500 µL) at ambient temperature for 4 hours, concentrated under reduced pressure and co-evaporated with acetonitrile (2×10 mL). The residue was taken up in 1N NaOH (3 eq.)/methanol (250 µL)/THF (250 µL), stirred for 3 hours and concentrated under reduced pressure to provide the titled compound. MS (ESI (+)) m/e 742, 743 (M+H)+; $^1$H NMR (500 MHz, DMSO-$d_6$) 8.08–7.92 (m, 2H), 7.45–6.94 (m, 7H), 6.64 (d, 2H), 4.43–4.38 (m, 1H), 3.90–3.86 (m, 2H), 3.78 (s, 3H), 3.10–3.05 (m, 2H), 2.90–2.85 (m, 1H), 2.75–2.62(m, 3H), 1.76(s, 3H), 1.64–1.58 (m, 2H), 1.52–1.45 (m, 2H), 1.18 (t, 3H).

EXAMPLE 20

2-((carboxycarbonyl){4-[3-({4-[3-hydroxy-2-(methoxycarbonyl)phenoxy]butyl}amino)-3-oxopropyl]-[(carboxycarbonyl)(2-carboxyphenyl)amino]-1-naphthyl}amino)benzoic acid

EXAMPLE 20A 3-(4-amino-1-naphthyl)propanoic acid

To a mixture of 4-bromo-1-naphthylamine (4.44 g, 20.0 mmol), potassium acetate (6.28 g, 64.0 mmol), tetrabutylammonium chloride hydrate (6.1 g, 22 mmol), palladium (II)acetate (224 mg, 1.0 mmol) and tri-o-tolylphosphine (1.22 g, 4.0 mmol) was added DMF (60 mL) and methyl acrylate (2.3 mL, 25 mmol). The reaction was heated to 100° C. under $N_2$ for 2 hours, poured into water (300 mL) and extracted with diethyl ether (3×50 mL). The combined ether layers were washed with brine (1×50 mL), dried (MgSO$_4$), filtered, and concentrated under reduced pressure. The product was purified on silica gel eluting with 30% ethyl acetate/hexanes to provide the titled compound 2.5 g, 55%).

A solution of 3-(4-amino-naphthalen-1-yl)-acrylic acid methyl ester (2.5 g, 11.0 mmol) and 10% Pd—C (320 mg) in methanol (100 mL) under an atmosphere of $H_2$ for 18 hours then filtered. To the filtrate was added 19M NaOH (3 mL), and the resulting mixture heated to reflux for 30 minutes. The mixture was concentrated under reduced pressure taken up in water (10 mL) and the pH adjust to 4 with 12M HCl. The mixture was extracted with ethyl acetate (3×20 mL), then the combined ethyl acetate layers were washed with brine (1×10 mL), dried (MgSO$_4$), filtered, and concentrated under reduced pressure to provide the titled compound (2.4 g, 100%).

EXAMPLE 20B methyl 2-(4-{[3-(4-amino-1-naphthyl)propanoyl]amino}butoxy)-6-hydroxybenzoate A mixture of 3-(4-amino-1-naphthyl)propanoic acid (160 mg, 0.74 mmol), 2-(4-amino-butoxy)-6-hydroxy-benzoic acid methyl ester hydrochloride (200 mg, 0.72 mmol), [(benzotriazol-1-yloxy)-dimethylamino-methylene]-dimethyl-ammonium tetrafluoroborate (TBTU) (275 mg, 0.857 mmol) and N,N-diisopropylethylamine (0.4 mL, 2.3 mmol) in DMF (3 mL) was stirred at ambient temperature for 1.5 hour, poured into water (10 mL) and extracted with ethyl acetate (3×20 mL). The combined ethyl acetate layers were washed with water (2×5 mL), dried (MgSO$_4$), filtered, and concentrated under reduced pressure to an oil. The product was purified on silica gel, eluting with 75% ethyl acetate/hexanes to provide the titled compound (165 mg, 52%).

EXAMPLE 20C 2-((carboxycarbonyl){4-[3-({4-[3-hydroxy-2-(methoxycarbonyl)phenoxy]butyl}amino)-3-oxopropyl]-1-naphthyl}amino)benzoic acid To a solution of methyl 2-(4-{[3-(4-amino-1-naphthyl)propanoyl]amino}butoxy)-6-hydroxybenzoate (82 mg, 0.19 mmol) in DMF (1 mL) was added diphenyliodonium-2-carboxylate monohydrate (75 mg, 0.22 mmol) and copper (II)acetate (3 mg, 0.017 mmol). The mixture was heated to 100° C. under $N_2$ for 2 hours then cooled to ambient temperature followed by the addition of triethylamine (200 µL, 1.43 mmol), and ethyl oxalyl chloride (100 µL, 0.893 mmol). The mixture was stirred for 45 minutes at ambient temperature followed by the addition of 0.33M NaOH (12 mL) was stirred for an additional 10 minutes. The mixture adjusted to a pH=3 by the addition of 1M HCl (6 ml), and extracted with ethyl acetate (3×3 mL). The combined ethyl acetate layers were washed with brine (1×3 mL), dried (MgSO$_4$), filtered, and concentrated under reduced to an oil. The oil was purified on reverse phase HPLC, eluting with 0% to 70% acetonitrile/0.1% aqueous trifluoroacetic acid gradient to provide the titled compound (46 mg, 39%). $^1$H NMR (300 MHz, $d_6$-DMSO) mixture of rotamers, δ 9.92 (s, 1H), 8.43 (d, 1H, J=8.1 Hz), 8.21–7.89 (m, 3H), 7.85 (dd, 1H, J=1.9, 7.3 Hz), 7.66–7.25 (m, 9H), 7.15 (t, 1H, J=8.5 Hz), 6.85 (dd, 1H, J=0.7, 7.5 Hz), 6.47 (d, 2H, J=8.5 Hz), 3.93–3.87 (m, 2H), 3.72 (s, 3H), 3.71 (s, 3H, minor), 3.35–3.25 (m, 2H), 3.11–3.02 (m, 2H), 2.54–2.45 (m, 2H), 1.63–1.40 (m, 4H); MS (ESI) m/z 629 [M+H]+, 646 [M+NH$_4$]+.

EXAMPLE 21 methyl 2-(4-{[4-[(carboxycarbonyl)(2-carboxyphenyl)amino]-N-(methoxycarbonyl)-L-phenylalanyl]amino}butoxy)-6-hydroxy-4-pentylbenzoate

EXAMPLE 21A 2,6-dihydroxy-4-pentylbenzoic acid

A mixture of olivetol (2.1 g, 12 mM), KHCO$_3$ (4.9 g, 39 mM), and solid CO$_2$ (1.95 g, 44.3 mM) in glycerol (5.1 mL) was heated in a stainless steel bomb to 145° C. at 220 psi for 5 hours. The reaction was cooled and removed from the reaction vessel using water to transfer. The aqueous solution was carefully acidified to a pH=3 with 1 N HCl to give a precipitate. The solids were filtered, washed with water and dried to give the desired product. MS (ESI(–)) m/e 223 (M–H)+; $^1$H NMR (300 MHz, CDCl$_3$) δ 9.40 (bs, 2H), 6.37 (s, 2H), 2.52 (t, 2H), 1.66–1.57 (m, 2H), 1.37–1.29 (m, 4H), 0.93–0.87 (m, 3H).

EXAMPLE 21B methyl 2,6-dihydroxy-4-pentylbenzoate

A solution of 2,6-dihydroxy-4-pentylbenzoic acid (2.0 g, 8.9 mM) in ether was treated with a 0.3 M solution of diazomethane in ether (30 mL) and stirred for 10 minutes. Nitrogen was bubbled through the solution for 10 minutes and then glacial acetic acid (4 drops). The reaction was concentrated under reduced pressure and purified by chromatography (5% ethyl acetate in hexanes) to give the desired product. MS ESI(–)) m/e 237 (M–H)+; $^1$H NMR (300 MHz, CDCl$_3$) δ 9.62 (bs, 2H), 6.33 (s, 2H), 4.06 (s, 3H), 2.50 (t, 2H), 1.64–1.55 (m, 2H), 1.34–1.27 (m, 4H), 0.92–0.87 (m, 3H).

EXAMPLE 21C methyl 2-(4-{[4-[(carboxycarbonyl)(2-carboxyphenyl)amino]-N-(methoxycarbonyl)-L-phenylalanyl]amino}butoxy)-6-hydroxy-4-pentylbenzoate The tilted compound was prepared according to the procedure described for Example 22F-G, substituting the salicylate from Example 22E with the salicylate from Example 21B. MS (ESI(+)) m/e 722 (M+H)$^+$; $^1$H NMR (300 MHz, DMSO-d$_6$) δ 0.85 (t, J=6.75 Hz, 3H), 1.17–1.39 (m, 4H), 1.39–1.70 (m, 6H), 2.46 (t, J=8.7 Hz, 2H), 2.63–2.82 (m, 1H), 2.82–2.96 (m, 1H), 2.96–3.14 (m, 2H), 3.70 (s, 3H), 3.93 (s, 3H), 3.83–3.95 (m, 2H), 4.06–4.20 (m, 1H), 6.30 (s, 1H), 6.33 (s, 1H), 7.12–7.69 (m, 8H), 7.86 (t, J=7.8 Hz, 1H), 7.97 (t, J=5.1 Hz, 1H), 9.91 (s, 1H).

EXAMPLE 22 methyl 2-(4-{[4-[(carboxycarbonyl)(2-carboxyphenyl)amino]-N-(methoxycarbonyl)-L-phenylalanyl]amino}butoxy)-6-hydroxy-4-methoxybenzoate

EXAMPLE 22A

N-(methoxycarbonyl)-4-nitro-L-phenylalanine

To a stirred mixture of H-phe(4-NO2)-OH (11.4 g, 50.0 mmol) and NaOH (2.0 g, 50.0 mmol) in water (450 mL) at 0° C. was added methylchloroformate (4.25 mL, 55.0 mmol) and NaOH (2.2 g in 45 mL water) simultaneously. 1N NaOH was then added to adjust PH ~9. The reaction mixture was stirred at ambient temperature overnight, the pH was adjust to 10 by adding more aqueous NaOH and the mixture was extracted with ether (2×75 mL). The aqueous layer was acidified to a pH=3 with 5N HCl, and extracted with ethyl acetate (2×400 mL). The combined ethyl acetate layers were dried (MgSO$_4$), filtered and concentrated under reduced pressure to provide the titled compound (12.3 g). MS (ESI (–)) m/e 267 (M–H)$^+$; $^1$H NMR (300 MHz, DMSO-d$_6$) 8.16 (d, 2H), 7.60–7.52 (m, 3H), 4.28–4.18 (m, 1H), 3.47 (s, 3H), 3.26–3.17 (m, 1H), 3.05–2.92 (m, 1H).

EXAMPLE 22B 4-amino-N-(methoxycarbonyl)-L-phenylalanine

A mixture of material from Example 22A and 10% Pd—C (500 mg) in methanol (250 mL) was stirred under an atmosphere of hydrogen at ambient temperature for 4 hours. The mixture was filtered through celite and the filtrate concentrated under reduced pressure to provide the titled compound. MS (ESI (–)) m/e 237 (M–H)$^+$; $^1$H NMR (300 MHz, DMSO-d$_6$) 7.32 (d, 1H), 6.88 (d, 2H), 6.45 (d, 2H), 4.05–3.96 (m, 1H), 3.47 (s, 3H), 3.49–3.40 (m, 2H), 2.89–2.80 (m, 1H), 2.67–2.57 (m, 1H).

EXAMPLE 22C

4-{{2-[(benzhydryloxy)carbonyl]phenyl}[(benzyloxy)(oxo)acetyl]amino}-N-(methoxycarbonyl)-L-phenylalanine The titled compound was prepared according to the procedure described for Example 1D-G, substituting 4-amino-N-(methoxycarbonyl)-L-phenylalanine for N-acetyl-4-amino-3-ethylphenylalanine and the benzyl oxalyl chloride for tert-butyl oxalyl chloride. MS ESI(–)) m/e 685 (M–H)$^+$; $^1$NMR (500 MHz, DMSO-d$_6$) 8.12–8.03 (m, 1H), 7.71–6.87 (m, 23H), 4.97–4.82 (m, 2H), 4.15–4.08 (m, 1H), 3.46, 3.42 (s, s, 3H), 3.07–2.96 (m, 1H), 2.83–2.73 (m, 1H).

EXAMPLE 22D

N-(4-hydroxybutyl)-[N-(methoxycarbonyl)-4-{{2-[(benzhydryloxy)carbonyl]phenyl}[(benzyloxy)(oxo)acetyl]amino}]-L-phenylalaninamide The titled compound was prepared according to the procedure described in Example 13B, substituting 4-{{2-[(benzhydryloxy)carbonyl]phenyl}[(benzyloxy)(oxo)acetyl]amino}-N-(methoxycarbonyl)-L-phenylalanine for N-acetyl-4-{2-[(benzhydryloxy)carbonyl][(benzyloxy)(oxo)acetyl]anilino}-3-ethylphenylalanine and aminobutanol for methyl 2-(4-aminobutoxy)-6-hydroxybenzoate. MS (ESI(+)) m/e 758 (M+H)$^+$; $^1$H NMR (300 MHz, DMSO-d$_6$) 8.13–8.02(m, 1H), 7.92 (t, 1H), 7.71–6.87 (m, 23H), 4.97–4.82 (m, 2H), 4.40–4.35 (m, 1H), 4.19–4.08 (m, 1H), 3.42, 3.39 (s, s, 3H), 3.07–2.96 (m, 2H), 2.94–2.62 (m, 2H), 1.42–1.34 (m, 4H).

EXAMPLE 22E methyl 2,6-dihydroxy-4-methoxybenzoate

The tilted compound was prepared according to the procedure described for Example 12A, substituting 2,4,6-trihydroxybenzoate for 2,6-dihydroxybenzoate and methanol for tert-butyl 4-hydroxybutylcarbamate.

EXAMPLE 22F methyl 2-(4-{[4-{{2-[(benzhydryloxy)carbonyl]phenyl}[(benzyloxy)(oxo)acetyl]amino}-N-(methoxycarbonyl)-L-phenylalanyl]amino}butoxy)-6-hydroxy-4-methoxybenzoate The tilted compound was prepared according to the procedure described for Example 12A, substituting methyl 2,6-dihydroxy-4-methoxybenzoate for 2,6-dihydroxybenzoate and N-(4-hydroxybutyl)-[N-(methoxycarbonyl)-4-{{2-[(benzhydryloxy)carbonyl]phenyl}[(benzyloxy)(oxo)acetyl]amino}]-L-phenylalaninamide for tert-butyl 4-hydroxybutylcarbamate.

EXAMPLE 22G methyl 2-(4-{[4-[(carboxycarbonyl)(2-carboxyphenyl)amino]-N-(methoxycarbonyl)-L-phenylalanyl]amino}butoxy)-6-hydroxy-4-methoxybenzoate A mixture of methyl 2-(4-{[4-{{2-[(benzhydryloxy)carbonyl]phenyl}[(benzyloxy)(oxo)acetyl]amino}-N-(methoxycarbonyl)-L-phenylalanyl]amino}butoxy)-6-hydroxy-4-methoxybenzoate and 10% Pd—C (0.1 g) in methanol (25 mL) was stirred under an atmosphere of hydrogen at ambient temperature for 16 hours. The mixture was filtered through celite and the filtrate concentrated under reduced pressure to provide the titled compound. MS (ESI (+)) m/e 682 (M+H)$^+$; $^1$H NMR (500 MHz, DMSO-d$_6$) 10.66, 10.67 (s, s, 1H), 8.03–7.96 (m, 1H), 7.90–7.83 (m, 1H), 7.63–7.15 (m, 8H), 6.07–6.05 (m, 2H), 4.18–4.10 (m, 1H), 3.95–3.89 (m, 2H), 3.73 (s, 3H), 3.43 (s, 3H), 3.15–3.02 (m, 2H), 2.95–2.86 (m, 1H), 2.78–2.68 (m, 1H), 1.68–1.56 (m, 2H), 1.54–1.47 (m, 2H).

EXAMPLE 23 methyl 3-(4-{[4-[(carboxycarbonyl)(2-carboxyphenyl)amino]-N-(methoxycarbonyl)-L-phenylalanyl]amino}butoxy)-5-hydroxy-1,1'-biphenyl-4-carboxylate

EXAMPLE 23A 1,1'-biphenyl-3,5-diol

A mixture of 5-phenyl-1,3-cyclohexanedione (2.5 g, 13 mM) and 10% Pd/C (0.5 g) in phenyl ether (30 mL) was heated to 230° C. over 30 minutes and held at 230° C. for 2.5 hours. The reaction was cooled, taken up in CH$_2$Cl$_2$ and filtered through Dicalite. The filtrate was concentrated and the residue purified by chromatography (CH$_2$Cl$_2$, then 5–10% EtOAc/CH$_2$Cl$_2$) to give the desired product.

MS ESI(−)) m/e 185 (M−H)$^+$.

EXAMPLE 23B 3,5-dihydroxy-1,1'-biphenyl-4-carboxylic acid

The desired product was prepared by substituting 1,1'-biphenyl-3,5-diol for olivetol in EXAMPLE 20A. MS ESI (−)) m/e 229 (M−H)$^+$; $^1$H NMR (300 MHz, CDCl$_3$) δ 9.58 (bs, 2H), 7.63–7.58 (m, 2H), 7.46–7.38 (m, 4H), 6.79 (s, 2H).

EXAMPLE 23C methyl 3,5-dihydroxy-1,1'-biphenyl-4-carboxylate

The desired product was prepared by substituting 3,5-dihydroxy-1,1'-biphenyl-4-carboxylic acid for 2,6-dihydroxy-4-pentylbenzoic acid in Example 20B.

MS ESI(−)) m/e 243 (M−H)$^+$; $^1$H NMR (300 MHz, CDCl$_3$) δ 9.69 (bs, 2H), 7.61–7.57 (m, 2H), 7.47–7.35 (m, 3H), 6.76 (s, 2H), 4.05 (s, 3H).

EXAMPLE 23D methyl 3-(4-{[4-{{2-[(benzhydryloxy)carbonyl] phenyl}[(benzyloxy)(oxo)acetyl]amino}-N-(methoxycarbonyl)-L-phenylalanyl]amino}butoxy)-5-hydroxy-1,1'-biphenyl-4-carboxylate A solution of methyl 3,5-dihydroxy-1,1'-biphenyl-4-carboxylate (31 mg, 0.13 mM), the core alcohol (made by Gang Liu) (95 mg, 0.13 mM), and Ph$_3$P (41 mg, 1.6 mM) in THF (5 mL) was treated with DEAD (20 µL, 1.6 mM) and stirred for 2 hours. The reaction was concentrated and purified by chromatography (CH$_2$Cl$_2$, then 10% EtOAc/CH$_2$Cl$_2$) to give the desired product.

MS ESI(−)) m/e 983 (M−H)$^+$.

EXAMPLE 23E methyl 3-(4-{[4-{{2-carbonylphenyl}[(benzyloxy) (oxo)acetyl]amino}-N-(methoxycarbonyl)-L-phenylalanyl]amino}butoxy)-5-hydroxy-1,1'-biphenyl-4-carboxylate A solution of methyl 3-(4-{[4-{{2-[(benzhydryloxy) carbonyl]phenyl}[(benzyloxy)(oxo)acetyl]amino}-N-(methoxycarbonyl)-L-phenylalanyl]amino}butoxy)-5-hydroxy-1,1'-biphenyl-4-carboxylate (120 mg, 0.12 mM) in methanol (25 mL) was stirred for 16 hours over 10% Pd/C under an atmosphere of H$_2$. The mixture was filtered, concentrated under reduced pressure and purified by preparative HPLC to give the desired product. MS (ESI(+)) m/e 728 (M+H)$^+$; $^1$H NMR (300 MHz, DMSO-d$_6$) δ 10.15 (bs, 1H), 8.13–8.06 (m, 1H), 7.99–7.06 (m, 1H), 7.73–7.12 (m, 13H), 6.99–6.89 (m, 2H), 6.74–6.71 (m, 2H), 4.13–4.08 (m, 1H), 4.06–4.02 (m, 2H), 3.75 (s, 3H), 3.43 and 3.42 (2s, 3H total), 3.12–3.06 (m, 2H), 2.89–2.83 (m, 1H), 2.76–2.65 (m, 1H), 1.64–1.58 (m, 2H), 1.53–1.47 (m, 2H).

EXAMPLE 24 methyl 2-(4-{[4-[(carboxycarbonyl)(2-carboxyphenyl)amino]-N-(methoxycarbonyl)-L-phenylalanyl]amino}butoxy)-6-hydroxy-4-methylbenzoate The titled compound was prepared according to the procedure described in Example 22F-G, substituting 4-methyl-2,6-dihydroxybenzoate for methyl 2,6-dihydroxy-4-methoxybenzoate. MS (ESI(+)) m/e 666 (M+H)$^+$; $^1$H NMR (500 MHz, DMSO-d$_6$) 9.93 (s, 1H), 7.96–7.76 (m, 2H), 7.61–7.13 (m, 8H), 6.16–6.14 (m, 2H), 4.18–4.10 (m, 1H), 3.94–3.87 (m, 2H), 3.71 (s, 3H), 3.44 (s, 3H), 3.12–3.00 (m, 2H), 2.95–2.84 (m, 1H), 2.80–2.68 (m, 1H), 2.21 (s, 3H), 1.64–1.54 (m, 2H), 1.54–1.45 (m, 2H).

EXAMPLE 25 methyl 2-(4-{[3-(4-[(carboxycarbonyl)(2-carboxyphenyl)amino]-3-ethylphenyl)propanoyl] amino}butoxy)-6-hydroxybenzoate

EXAMPLE 25A benzyl (2E)-3-(4-aminophenyl)acrylate

The titled compound was prepared according to the procedure described in Example 1B, substituting benzylacrylate for 2-acetylamino-benzylacrylate. MS (ESI(+)) m/e 282 (M+H)$^+$; $^1$H NMR (300 MHz, DMSO-d$_6$) 7.52 (d, 1H), 7.40–7.24 (m, 7H), 6.59 (d, 1H), 6.29 (d, 1H), 5.57 (s, 2H), 5.28 (s, 2H), 2.48 (q, 2H), 1.12 (t, 3H).

EXAMPLE 25B 3-(4-{{2-[(benzhydryloxy)carbonyl]phenyl} [(benzyloxy)(oxo)acetyl]amino}phenyl)propanoic acid The titled compound was prepared according to the procedure described for Example 1C-G, substituting benzyl (2E)-3-(4-aminophenyl)acrylate for benzyl (2E)-2-(acetylamino)-3-(4-amino-3-ethylphenyl)-2-propenoate. MS (ESI(+)) m/e 642 (M+H)$^+$.

EXAMPLE 25C 2-((carboxycarbonyl){2-ethyl-4-[3-({4-[3-hydroxy-2-(methoxycarbonyl)phenoxy]butyl}amino)-3-oxopropyl]phenyl}amino)benzoic acid The titled compound was prepared according to the procedure described in Example 13B-C, substituting 3-(4-{{2-[(benzhydryloxy)carbonyl]phenyl}[(benzyloxy)(oxo) acetyl]amino}phenyl)propanoic acid for N-acetyl-4-{2-[(benzhydryloxy)carbonyl][(benzyloxy)(oxo)acetyl] anilino}-3-ethylphenylalanine. MS (ESI(+)) m/e 607 (M+H)$^+$; $^1$H NMR (500 MHz, DMSO-d$_6$) δ 9.90 (s, 1H), 7.85–7.73 (m, 2H), 7.54–6.80(m, 7H), 6.47 (d, 2H), 3.95–3.89 (m, 2H), 3.72 (d, 3H), 3.12–3.04 (m, 2H), 2.87–2.75 (m, 2H), 2.69–2.55 (m, 2H), 2.42–2.32 (m, 2H), 1.65–1.54 (m, 2H), 1.52–1.42(m, 2H), 1.29–0.91 (m, 3H).

EXAMPLE 26 methyl 2-(4-{[4-[(carboxycarbonyl)(2-carboxyphenyl)amino]-N-(methoxycarbonyl)-L-phenylalanyl]amino}butoxy)-4-chloro-6-hydroxybenzoate

EXAMPLE 26A 5-chlorobenzene-1,3-diol

A solution of 5-chloro-1,3-dimethoxybenzene (5.41 g, 31.3 mM) in methylene chloride (75 mL) at −78° C. was stirred with a 1M solution of BBr$_3$ in methylene chloride (63 mL) for 45 minutes. The reaction was allowed to warm to room temperature overnight and diluted with water (75 mL). The layers were separated and the aqueous layer washed two times with methylene chloride. The aqueous layer was acidified with 1N HCl and extracted 3 times with ethyl acetate. The combined organic layers were washed with 1N sodium thiosulfate (1×35 mL) and water (1×25 mL). The organic layer was dried (MgSO$_4$), filtered and concentrated under reduced pressure and purified by chromatography (methylene chloride/acetone) to provide the titled compound. MS ESI(−)) m/e 143 (M−H)$^+$; $^1$H NMR (300 MHz, CDCl$_3$) δ 6.45 (d, 2H), 6.25 (t, 1H), 5.41 (bs, 2H).

EXAMPLE 26B 4-chloro-2,6-dihydroxybenzoic acid

The desired product was prepared by substituting 5-chlorobenzene-1,3-diol for olivetol in Example 20A. MS ESI(−)) m/e 187 (M−H)$^+$.

EXAMPLE 26C methyl 4-chloro-2,6-dihydroxybenzoate

The desired product was prepared by substituting 4-chloro-2,6-dihydroxybenzoic acid for 2,6-dihydroxy-4-pentylbenzoic acid in Example 20B. MS ESI(−)) m/e 233 (M−H)$^+$; $^1$H NMR (300 MHz, CDCl$_3$) δ 9.75 (bs, 2H), 6.52 (s, 2H), 4.09 (s, 2H).

EXAMPLE 26D methyl 2-(4-{[4-[(carboxycarbonyl)(2-carboxyphenyl)amino]-N-(methoxycarbonyl)-L-phenylalanyl]amino}butoxy)-4-chloro-6-hydroxybenzoate The desired product was prepared by substituting methyl 4-chloro-2,6-dihydroxybenzoate for methyl 3,5-dihydroxy-1,1'-biphenyl-4-carboxylate in Example 23D-E. MS ESI(−)) m/e 684 (M−H)$^+$.

EXAMPLE 27 methyl 2-(4-{[4-[(carboxycarbonyl)(2-carboxyphenyl)amino]-N-(methoxycarbonyl)-L-phenylalanyl]amino}butoxy)-6-hydroxybenzoate The titled compound was prepared according to the procedure described in Example 22, substituting 2,6-dihydroxybenzoate for methyl 2,6-dihydroxy-4-methoxybenzoate. MS (ESI(+)) m/e 652 (M+H)$^+$; $^1$H NMR (500 MHz, DMSO-d$_6$) 9.90 (s, 1H), 7.96–7.64 (m, 2H), 7.63–7.13 (m, 8H), 6.50–6.45 (m, 2H), 4.18–4.10 (m, 1H), 3.94–3.87 (m, 2H), 3.72 (s, 3H), 3.44 (s, 3H), 3.12–3.00 (m, 2H), 2.95–2.86 (m, 1H), 2.80–2.68 (m, 1H), 1.64–1.54 (m, 2H), 1.52–1.44 (m, 2H).

EXAMPLE 28

4-[(carboxycarbonyl)(2-carboxyphenyl)amino]-N-{4-[2-(aminocarbonyl)-3-hydroxyphenoxy]butyl}-N-(methoxycarbonyl)-L-phenylalaninamide The titled compound was prepared according to the procedure described in Example 22, substituting 2,6-dihydroxybenzamide for Example 22E. MS (ESI(+)) m/e 637 (M+H)$^+$; $^1$H NMR (500 MHz, DMSO-d$_6$) 13.99 (bs, 1H), 8.13 (s, 1H), 8.02–7.95 (m, 2H), 7.88–7.82 (m, 1H), 7.63–7.16 (m, 8H), 6.58–6.45 (m, 2H), 4.18–4.06 (m, 3H), 3.43 (s, 3H), 3.12–3.04 (m, 2H), 2.95–2.86 (m, 1H), 2.80–2.68 (m, 1H), 1.78–1.69 (m, 2H), 1.54–1.45 (m, 2H).

EXAMPLE 29 methyl 3-(4-{[4-[(carboxycarbonyl)(2-carboxyphenyl)amino]-N-(methoxycarbonyl)-L-phenylalanyl]amino}butoxy)-1-hydroxy-2-naphthoate

EXAMPLE 29A 1,3-dihydroxy-2-naphthoic acid methyl ester

A mixture of 1,3-dihydroxynaphthalene (480 mg, 3.00 mmol) and potassium bicarbonate (750 mg, 7.5 mmol) in glycerol (1 mL) was heated under 1 atmosphere of CO$_2$ to 115° C. for 5 hours then poured into 0.5M HCl (20 mL) and extracted with diethyl ether (3×5 mL). The combined ether layers were washed with brine (1×5 mL), dried (MgSO$_4$) and filtered. This solution was then treated with a solution of diazomethane in diethyl ether until bubbling ceased. The ether was removed under reduced pressure and purified on silica gel eluting with 20% ethyl acetate/hexanes to provide (75 mg, 11%).

EXAMPLE 29B methyl 3-hydroxy-1-(methoxymethoxy)-2-naphthoate

To a solution of 1,3-dihydroxy-2-naphthoic acid methyl ester 109 mg (0.53 mmol) in DMF (2 mL) was added triethylamine (200 μL, 1.43 mmol) and chloromethyl methyl ether (MOMCl) (125 μL, 1.65 mmol). The mixture was stirred at ambient temperature for 16 hours, poured into water (10 mL) and extracted with diethyl ether (2×5 mL). The combined ether layers were washed with 1M HCl (1×3 mL), brine (1×5 mL), dried (MgSO$_4$), filtered, and concentrated under reduced pressure to an oil. The oil was purified on silica gel eluting with 20% ethyl acetate/hexanes to provide the titled compound (83 mg, 60%).

EXAMPLE 29C methyl 3-{4-[(tert-butoxycarbonyl)amino]butoxy}-1-(methoxymethoxy)-2-naphthoate To a mixture of methyl 3-hydroxy-1-(methoxymethoxy)-2-naphthoate (41 mg, 0.16 mmol), triphenylphosphine (41 mg, 0.16 mmol) and N-(tert-butoxycarbonyl)-4-hydroxy-1-butylamine (33 mg, 0.17 mmol) in THF (0.5 mL) was added diethylazodicarboxylate (30 μL, 0.19 mmol). The mixture was stirred at ambient temperature for 30 minutes, concentrated under reduced pressure and purified on silica gel eluting with 30% ethyl acetate/hexanes to provide the titled compound (28 mg, 41%).

EXAMPLE 29D methyl 3-(4-aminobutoxy)-1-hydroxy-2-naphthoate

To a mixture of methyl 3-{4-[(tert-butoxycarbonyl)amino]butoxy}-1-(methoxymethoxy)-2-naphthoate (28 mg, 0.064 mmol) was added 4M HCl in dioxane (1 mL). The mixture was stirred at ambient temperature for 30 minutes, concentrated under reduced pressure to provide the titled compound (19 mg, 100%) as its hydrochloride salt.

EXAMPLE 29E methyl 3-(4-{[4-{{2-[(benzhydryloxy)carbonyl]phenyl}[(benzyloxy)(oxo)acetyl]amino}-N-(methoxycarbonyl)-L-phenylalanyl]amino}butoxy)-1-hydroxy-2-naphthoate To a mixture of methyl 3-(4-aminobutoxy)-1-hydroxy-2-naphthoate (18 mg, 0.055 mmol), 2-{benzyloxyoxalyl-[4-

(2-carboxy-2-methoxycarbonylamino-ethyl)-phenyl]-amino}-benzoic acid benzhydryl ester (40 mg, 0.058 mmol), 1-(3-(dimethylamino)propyl)-3-ethylcarbodiimide hydrochloride (13 mg, 0.068 mmol) and 3-hydroxy-1,2,3-benzotriazin-4(3H)-one (13 mg, 0.080 mmol) in DMF (0.2 mL) was added triethylamine (1 drop). The reaction was stirred at ambient temperature for 5 hours, concentrated under reduced pressure and purified on silica gel eluting with 75% ethyl acetate/hexanes to provide the titled compound (32 mg, 61%).

EXAMPLE 29F methyl 3-(4-{[4-[(carboxycarbonyl)(2-carboxyphenyl)amino]-N-(methoxycarbonyl)-L-phenylalanyl]amino}butoxy)-1-hydroxy-2-naphthoate To methyl 3-(4-{[4-{{2-[(benzhydryloxy)carbonyl]phenyl}[(benzyloxy)(oxo)acetyl]amino}-N-(methoxycarbonyl)-L-phenylalanyl]amino}butoxy)-1-hydroxy-2-naphthoate (32 mg, 0.033 mmol) in dioxane (1 mL) under $N_2$ was added 10% Pd—C (5 mg) followed by 60% $HClO_4$ (1 drop). The reaction was stirred under 1 atmosphere of $H_2$ for 4 hours and filtered. The solution was applied to a reverse phase HPLC column and purified by eluting with 0% to 70% gradient of acetonitrile/0.1% aqueous trifluoroacetic acid to provide the titled compound (13 mg, 56%).

$^1$H NMR (500 MHz, $d_6$-DMSO) mixture of rotamers, δ 11.02 (bs, 1H), 8.12 (d, 1H, J=8.4 Hz), 7.98 (bt, 1H, J=5.6 Hz), 7.93 (d, 1H, J=7.8 Hz), 7.85 (dd, 1H, J=1.4, 7.6 Hz), 7.73 (d, 1H, J=8.1 Hz), 7.62–7.56 (m, 1H), 7.52–7.48 (m, 1H), 7.44–7.39 (m, 1H), 7.36–7.23 (m, 6H), 7.19–7.18 (m, 1H), 7.08 (s, 1H, minor), 6.97 (s, 1H, minor), 6.89–6.88 (m, 1H), 4.20–4.12 (m, 1H), 4.05–4.02 (m, 2H), 3.84 (s, 3H), 3.44 (s, 3H), 3.18–3.12 (m, 2H), 2.95–2.89 (m, 1H), 2.79–2.71 (m, 1H), 1.75–1.67 (m, 2H), 1.60–1.54 (m, 2H); MS (ESI) m/z 702 [M+H]$^+$, 724 [M+Na]$^+$.

423728 EXAMPLE 30 Zhili Xin

4-[(carboxycarbonyl)(2-carboxyphenyl)amino]-N-(4-{3-hydroxy-2-[(methylamino)carbonyl]phenoxy}butyl)-N-(methoxycarbonyl)-L-phenylalaninamide

EXAMPLE 30A 2,6-dihydroxy-N-methylbenzamide

The mixture of 2,6-dihydroxybenzoate (168 mg, 1.0 mmol) and 2 M methylamine in THF (3 mL, 6.0 mmol) in a sealed tube was heated to 100° C. overnight. The reaction mixture was then concentrated under reduced pressure and purified on silica gel eluting with hexane/ethyl acetate (1:1) to provide titled compound (67 mg). MS (ESI(+)) m/e 168 (M+H)$^+$; $^1$H NMR (300 MHz, DMSO-$d_6$) 12.57(bs, 2H), 8.82 (bs, 1H), 7.14 (t, 1H), 6.35 (d, 2H), 2.85(d, 3H).

EXAMPLE 30B

4-[(carboxycarbonyl)(2-carboxyphenyl)amino]-N-(4-{3-hydroxy-2-[(methylamino)carbonyl]phenoxy}butyl)-N-(methoxycarbonyl)-L-phenylalaninamide The titled compound was prepared according to the procedure described in Example 22, substituting 2,6-dihydroxy N-methylbenzamide for methyl 2,6-dihydroxy-4-methoxybenzoate. MS (ESI(+)) m/e 651 (M+H)$^+$; $^1$H NMR (500 MHz, DMSO-$d_6$) 13.57 (bs, 1H), 8.96, 8.44 (s, s, 1H), 8.02–7.95 (m, 1H), 7.88–7.82 (m, 1H), 7.63–7.16 (m, 8H), 6.58–6.45 (m, 2H), 4.18–4.07 (m, 3H), 3.43 (s, 3H), 3.12–3.04 (m, 2H), 2.95–2.86 (m, 1H), 2.85 (d, 3H), 2.80–2.68 (m, 1H), 1.78–1.69 (m, 2H), 1.54–1.45 (m, 2H).

EXAMPLE 31 methyl 2-(4-{[3-(4-[(carboxycarbonyl)(2-carboxyphenyl)amino]-1-naphthyl)-1-methylpropyl]amino}butoxy)-6-hydroxybenzoate

EXAMPLE 31A

2-[(4-bromo-naphthalen-1-yl)-tert-butoxyoxalyl-amino]-benzoic acid benzhydryl ester The titled compound was prepared according to the procedure described in Example 7F-H, substituting 4-bromo-naphthalen-1-yl-amine for the aniline from Example 7E. MS (ESI(+)) m/e 653, 655 (M+NH$_4$)$^+$.

EXAMPLE 31B

2-{tert-butoxyoxalyl-[4-(3-oxo-butyl)-naphthalen-1-yl]-amino}-benzoic acid benzhydryl ester To a mixture of 2-[(4-bromo-naphthalen-1-yl)-tert-butoxyoxalyl-amino]-benzoic acid benzhydryl ester (230 mg, 0.36 mmol), Pd(OAc)$_2$ (4.0 mg, 0.018 mmol), P(o-tolyl)$_3$ (11 mg, 0.036 mmol) in anhydrous N,N-dimethylformamide (1.5 mL) in a pressure tube was added 3-buten-2-ol (47 μL, 0.54 mmol) and triethylamine (127 μL, 0.90 mmol). The mixture was flushed with nitrogen for 3 minutes, capped and heated to 100° C. for 30 min. The reaction mixture was allowed to cool to ambient temperature, partitioned between ethyl acetate and water (75 mL, 1:1). The organic layer was washed with brine (2×25 mL), dried (Na$_2$SO$_4$), filtered, concentrated under reduced pressure and purified on an Alltech Sep-Pak eluting with 20–30% ethyl acetate/hexanes to provide the titled compound (180 mg, 81%). MS (ESI(+)) m/e 645 (M+NH$_4$)$^+$, $^1$H NMR (300 MHz, DMSO-$d_6$) 1.40

EXAMPLE 31C

A mixture of 2-{tert-butoxyoxalyl-[4-(3-oxo-butyl)-naphthalen-1-yl]-amino}-benzoic acid benzhydryl ester (81 mg, 0.129 mmol) and amine from Example 12B (61 mg, 0.17 mmol) in anhydrous methanol (2.0 mL) was stirred at ambient temperature with Et$_3$N (24 μL, 0.129 mmol) for 3 hours. NaBH$_4$ (30 mg) was then added in portions over 30 minutes, stirred for an additional 2 hours and concentrated under reduced pressure to give a crude amine product which was used directly without any purification.

EXAMPLE 31D

The titled compound was prepared according to the procedure described in Example 12H, substituting the ester from Example 31C for the ester from Example 12G. MS (ESI+) m/e 629 (M+H)$^+$; $^1$H NMR (300 MHz, DMSO-$d_6$) 1.39 (t, J=6.45 Hz, 3H), 1.60–1.90 (m, 6H), 2.92–3.53 (m, 5H), 3.72 (m, 3H), 3.90–4.02 (m, 2H), 6.47 (d, J=2.7 Hz, 1H), 6.50 (d, J=2.7 Hz, 1H), 6.82–6.88 (m, 1H), 7.12–7.20 (m, 1H), 7.28–7.70 (m, 6H), 7.87 (dd, J=2.7, 7.5 Hz, 1H), 8.14 (d, J=9.0 Hz, 1H), 8.44 (d, J=8.4 Hz, 1H), 9.94 (s, 1H).

EXAMPLE 32 methyl 2-(4-{[3-(4-[(carboxycarbonyl)(2-carboxyphenyl)amino]-1-naphthyl)propyl]amino}butoxy)-6-hydroxybenzoate The titled compound was prepared according to the procedure described in Example 31B-D, substituting 3-buten-2-ol used in Example 31B with allyl alcohol. MS (ESI+) m/e 615 (M+H)+; 1H NMR (300 MHz, DMSO-d6) 1.60–1.90 (m, 6H), 2.77–3.58 (m, 6H), 3.72 (m, 3H), 3.90–4.02 (m, 2H), 6.09 (d, J=2.7 Hz, 1H), 6.46 (d, J=8.7 Hz, 1H), 6.83–7.93 (m, 9H), 7.98–8.22 (m, 1H), 8.33–8.53 (m, 1H), 9.94 (s, 1H).

EXAMPLE 33

4-[(carboxycarbonyl)(2-carboxyphenyl)amino]-N-(4-{2-[(ethylamino)carbonyl]-3-hydroxyphenoxy}butyl)-N-(methoxycarbonyl)-L-phenylalaninamide The titled compound was prepared according to the procedure described in Example 30A-B, substituting ethylamine for methylamine. MS (ESI(+)) m/e 665 (M+H)+; 1H NMR (500 MHz, DMSO-d6) 13.57 (bs, 1H), 8.50(s, 1H), 8.02–7.95 (m, 1H), 7.88–7.78 (m, 1H), 7.64–7.14 (m, 8H), 6.58–6.45 (m, 2H), 4.18–4.07 (m, 3H), 3.43 (s, 3H), 3.12–3.04 (m, 2H), 2.95–2.86 (m, 1H), 2.80–2.68 (m, 1H), 1.78–1.69 (m, 2H), 1.54–1.45 (m, 2H), 1.14 (t, 3H).

EXAMPLE 34 Zhili Xin

N-{4-[2-(acetylamino)-3-hydroxyphenoxy]butyl}-4-[(carboxycarbonyl)(2-carboxyphenyl)amino]-N-(methoxycarbonyl)-L-phenylalaninamide

EXAMPLE 34A

N-(2,6-dihydroxyphenyl)acetamide

A mixture of 2-nitroresorcinol (1.0 g, 6.45 mmol) and 10% Pd—C (100 mg) in methanol (15 mL) was stirred under an atmosphere of hydrogen at ambient temperature for 4 hours. The reaction mixture was filtered through celite and the filtrate concentrated under reduced pressure. A mixture of the residue, triethylamine (1.8 mL, 12.9 mmol) and acetyl chloride (1.38 mL, 19.35 mmol) in dichloromethane (15 mL) was stirred at ambient temperature for 1 hour, poured into 1N NaOH (20 mL) and methanol (20 mL). After 10 minutes, the mixture was concentrated under reduced pressure and taken up in ethyl acetate and 1N HCl (50 mL, 1:1). The layers were separated and the organic phase was washed with brine, dried (MgSO4), filtered and concentrated to provide titled compound. MS (ESI (−)) m/e 166(M−H)+; 1H NMR (300 MHz, DMSO-d6) 9.31(s, 2H), 6.86 (t, 1H), 6.34 (d, 2H), 2.11(s, 3H).

EXAMPLE 34B

N-{4-[2-(acetylamino)-3-hydroxyphenoxy]butyl}-4-[(carboxycarbonyl)(2-carboxyphenyl)amino]-N-(methoxycarbonyl)-L-phenylalaninamide The titled compound was prepared according to the procedure described in Example 30, substituting N-(2,6-dihydroxyphenyl)acetamide for 2,6-dihydroxy-N-methylbenzamide. MS (ESI(+)) m/e 651 (M+H)+; 1H NMR (500 MHz, DMSO-d6) 9.09 (bs, 1H), 9.00(s, 1H), 7.98–7.82 (m, 2H), 7.66–6.95 (m, 8H), 6.53–6.45 (m, 2H), 4.18–4.12 (m, 1H), 3.92–3.88 (m, 2H), 3.43 (s, 3H), 3.15–3.04 (m, 2H), 2.95–2.86 (m, 1H), 2.80–2.68 (m, 1H), 2.03 (s, 3H), 1.71–1.59 (m, 2H), 1.54–1.45 (m, 2H).

EXAMPLE 35

4-[(carboxycarbonyl)(2-carboxyphenyl)amino]-N-(4-{2-[(dimethylamino)carbonyl]-3-hydroxyphenoxy}butyl)-N-(methoxycarbonyl)-L-phenylalaninamide

EXAMPLE 35A 2,6-dimethoxy-N,N-dimethylbenzamide

A mixture of 2,6-dimethoxybenzoic acid (102 mg, 0.56 mmol), dimethylamine hydrochloride (91 mg, 1.12 mmol), 2-(1H-benzotriazole-1-yl)-1,1,3,3-tetramethyluronium tetrafluoroborate (234 mg, 0.73 mmol) and diisopropylethylamine (390 µL, 2.24 mmol) in DMF (1 mL) was stirred at ambient temperature overnight. The reaction mixture was taken up in ethyl acetate (50 mL) and aqueous. NaHCO3(50 mL). The organic phase was washed with brine (2×50 mL), dried (MgSO4), filtered and concentrated under reduced pressure. The residue was purified on silica gel eluting with ethyl acetate to provide titled compound (66 mg). MS (APCI(+)) m/e 210 (M+H)+.

EXAMPLE 35B 2,6-dihydroxy-N,N-dimethylbenzamide

To a mixture of 2,6-dimethoxy-N,N-dimethylbenzamide (64 mg, 0.3 mmol) dissolved in dichloromethane (2 mL) was added 1M BBr3 in dichloromethane (1 mL, 1.0 mmol)) under nitrogen atmosphere and stirred for 16 hours. The mixture was diluted with ethyl acetate and the mixture was washed with water (2×30 mL) and brine (2×30 mL). The organic phase was dried (MgSO4), filtered and concentrated under reduced pressure to provide titled compound (20 mg). MS ESI(−)) m/e 180 (M−H)+; 1H NMR (300 MHz, DMSO-d6) 9.36 (s, 2H), 6.92 (t, 1H), 6.30 (d, 2H), 2.97–2.73 (m, 6H).

EXAMPLE 35C

4-[(carboxycarbonyl)(2-carboxyphenyl)amino]-N-(4-{2-[(dimethylamino)carbonyl]-3-hydroxyphenoxy}butyl)-N-(methoxycarbonyl)-L-phenylalaninamide The titled compound was prepared according to the procedure described in Example 30, substituting 2,6-dihydroxy-N,N-dimethylbenzamide for 2,6-dihydroxy-N-methylbenzamide. MS (ESI(+)) m/e 663 (M−H)+; 1H NMR (500 MHz, DMSO-d6) 9.52 (s, 1H), 7.96–7.04 (m, 11H), 6.47–6.44 (m, 2H), 4.18–4.11 (m, 1H), 3.92–3.85 (m, 2H), 3.44 (s, 3H), 3.12–3.01 (m, 2H), 2.95–2.86 (m, 1H), 2.91 (s, 3H), 2.78–2.68 (m, 1H), 2.71 (s, 1H), 1.62–1.54 (m, 2H), 1.50–1.43 (m, 2H).

What is claimed is:

1. A compound of formula (I)

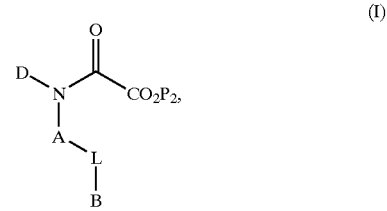

or a therapeutically acceptable salt, wherein

A is selected from the group consisting of
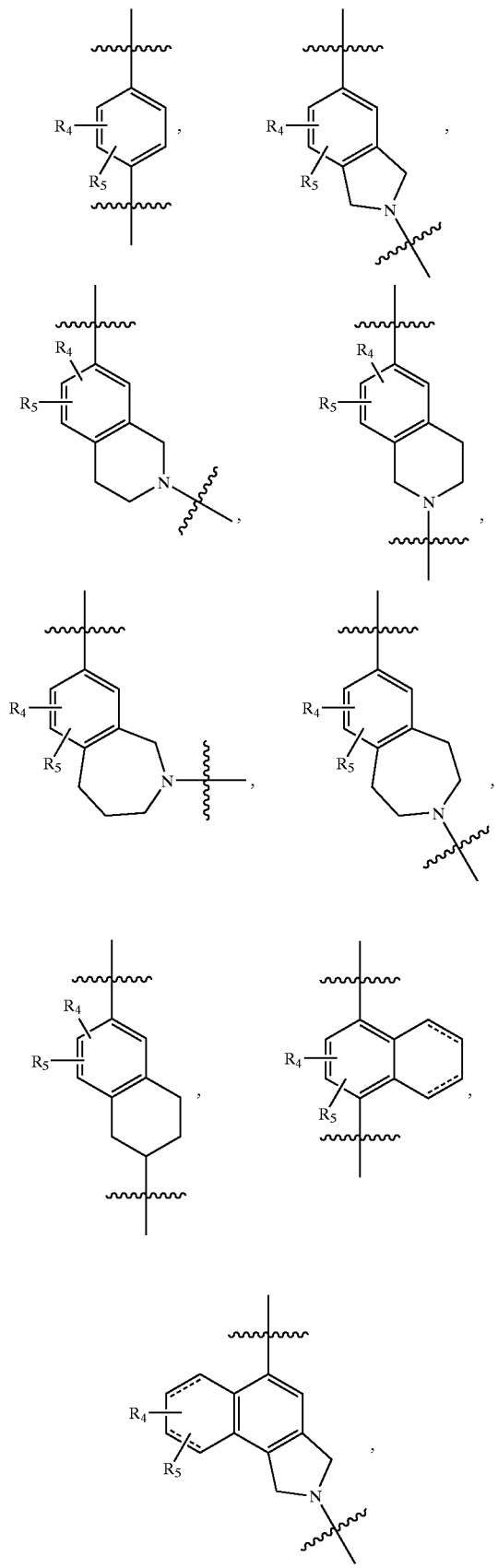
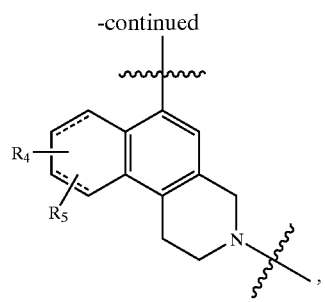
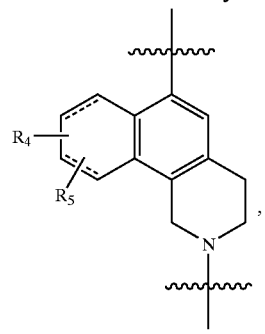
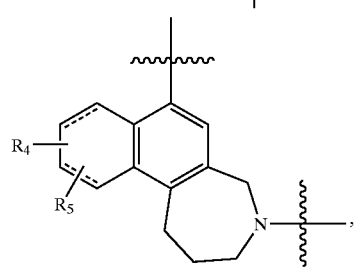
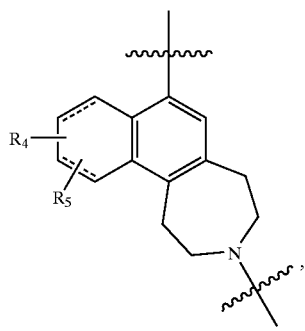
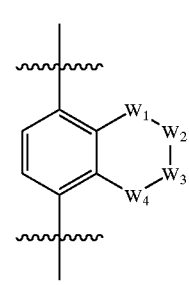
wherein the dotted line is either absent or is a single bond;
B is selected from the group consisting of hydrogen, alkyl, aryl, arylalkyl, D is selected from the group consisting of

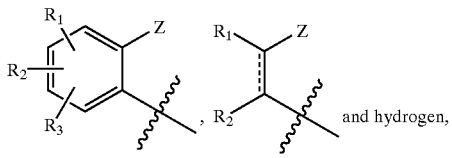

wherein Z is selected from the group consisting of alkoxy, alkyl, amino, cyano, nitro, $CO_2P_1$, $SO_3H$, $PO(OH)_2$, $CH_2PO(OH)_2$, $CHFPO(OH)_2$, $CF_2PO(OH)_2$, and $C(=NH)NH_2$;

wherein $P_1$ and $P_2$ are independently selected from the group consisting of hydrogen, alkyl, alkenyl, arylalkyl, cycloalkyl and (cycloalkyl)alkyl;

$R_1$, $R_2$, $R_3$, $R_4$ and $R_5$ are independently selected from the group consisting of hydrogen, alkoxy, alkyl, aryl, arylalkyl, cyano, halo, haloalkoxy, haloalkyl, hydroxy, hydroxyalkyl, nitro, $NR_AR_B$, $NR_AR_BC(O)$, $NR_AR_BC(O)$alkyl and $NR_AR_BC(O)$alkenyl, wherein $R_A$ and $R_B$ are independently selected from the group consisting of hydrogen, alkyl, alkoxycarbonyl, alkylsulfonyl, aryl, arylalkylcarbonyl, arylcarbonyl, arylsulfonyl and $(R_CR_DN)$carbonyl wherein $R_C$ and $R_D$ are independently selected from the group consisting of hydrogen, alkyl, aryl, and arylalkyl;

L is selected from the group consisting of —$(CH_2)_mX_1(CH_2)_nCH(R_8)C(R_{9A})(R_{9B})X_2(CH_2)_pC(O)N(R_{10})CH(CO_2R_{11})(CH_2)_qX_3$—; —$(CH_2)_mX_1(CH_2)_nCH(R_8)C(R_{9A})(R_{9B})X_2(CH_2)_pEC(O)N(R_{10})CH(CO_2R_{11})(CH_2)_qX_3$—; —$(CH_2)_mX_1(CH_2)_nCH(R_8)C(R_{9A})(R_{9B})X_2(CH_2)_pX_3$—; —$(CH_2)_mX_1(CH_2)_nCH(R_8)C(R_{9A})(R_{9B})X_2(CH_2)_pX_3(CH_2)_qX_4$—; and —$(CH_2)_mX_1(CH_2)_nCH(R_8)C(R_{9A})(R_{9B})X_2(CH_2)_pE(CH_2)_qX_3$—, wherein each group is drawn with the left end attached to A and the right end attached to B;

m, n, p and q are independently between 0–4;

$R_8$ is selected from the group consisting of hydrogen, hydroxy, $NR_AR_B$ and $(NR_AR_B)$alkyl;

$R_{9A}$ and $R_{9B}$ are independently selected from the group consisting of hydrogen, alkyl, hydroxyalkyl and $R_ER_F$Nalkyl, wherein $R_E$ and $R_F$ are independently selected from the group consisting of hydrogen, alkyl, alkoxycarbonyl and alkanoyl, or $R_{9A}$ and $R_{9B}$ taken together are oxo;

$R_{10}$ is selected from the group consisting of hydrogen, alkyl, alkanoyl and alkoxycarbonyl;

$R_{11}$ is independently selected from the group consisting of hydrogen, alkyl, alkenyl, arylalkyl, cycloalkyl, and (cycloalkyl)alkyl;

E is selected from the group consisting of aryl and cycloalkyl;

$X_1$, $X_2$, $X_3$, and $X_4$ are independently absent or are independently selected from the group consisting of $NR_G$, O, S, S(O) and $S(O)_2$, wherein $R_G$ is selected from the group consisting of hydrogen, alkyl, alkanoyl and alkoxycarbonyl; and $W_1$, $W_2$, $W_3$ and $W_4$ are independently selected from the group consisting of CH, $CH_2$, N, NH and O.

2. The compound according to claim 1 of formula (II)

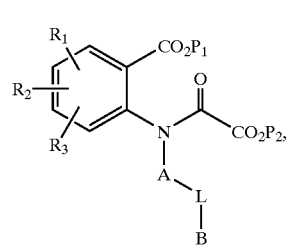

(II)

or a therapeutically acceptable salt wherein A, B, L, $P_1$, $P_2$, $R_1$, $R_2$, and $R_3$ are defined in claim 1.

3. The compound according to claim 2, wherein A is selected from the group consisting of

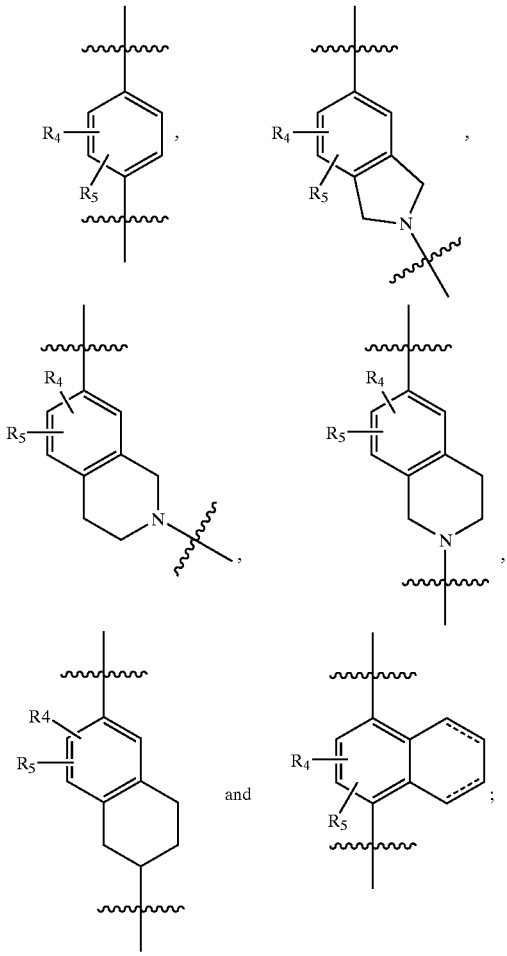

$R_1$, $R_2$, $R_3$, $R_4$ and $R_5$ are independently selected from the group consisting of hydrogen, alkoxy, alkyl, cyano, halo, haloalkoxy, haloalkyl, hydroxy, hydroxyalkyl, nitro, $NR_AR_B$, $NR_AR_BC(O)$, $NR_AR_BC(O)$alkyl and $NR_AR_BC(O)$alkenyl;

$R_{10}$ is selected from the group consisting of hydrogen and alkyl; and $R_{11}$ is independently selected from the group consisting of hydrogen, alkyl and arylalkyl.

4. The compound according to claim 2, wherein

L is —$(CH_2)_mX_1(CH_2)_nCH(R_8)C(R_{9A})(R_{9B})X_2(CH_2)_pC(O)N(R_{10})CH(CO_2R_{11})(CH_2)_qX_3$—.

5. The compound according to claim 2, wherein

L is —(CH$_2$)$_m$X$_1$(CH$_2$)$_n$CH(R$_8$)C(R$_{9A}$)(R$_{9B}$)X$_2$(CH$_2$)$_p$C(O)N(R$_{10}$)CH(CO$_2$R$_{11}$)(CH$_2$)$_q$X$_3$—; and R$_8$ is NR$_A$R$_B$.

6. The compound according to claim 2, wherein

L is —(CH$_2$)$_m$X$_1$(CH$_2$)$_n$CH(R$_8$)C(R$_{9A}$)(R$_{9B}$)X$_2$(CH$_2$)$_p$C(O)N(R$_{10}$)CH(CO$_2$R$_{11}$)(CH$_2$)$_q$X$_3$—;

R$_8$ is NR$_A$R$_B$; and

R$_{9A}$ and R$_{9B}$ together are oxo.

7. The compound according to claim 2, wherein

L is —(CH$_2$)$_m$X$_1$(CH$_2$)$_n$CH(R$_8$)C(R$_{9A}$)(R$_{9B}$)X$_2$(CH$_2$)$_p$C(O)N(R$_{10}$)CH(CO$_2$R$_{11}$)(CH$_2$)$_q$X$_3$—;

R$_8$ is NR$_A$R$_B$;

R$_{9A}$ and R$_{9B}$ together are oxo; and

X$_2$ is NR$_C$.

8. The compound according to claim 2, wherein

L is —(CH$_2$)$_m$X$_1$(CH$_2$)$_n$CH(R$_8$)C(R$_{9A}$)(R$_{9B}$))X$_2$(CH$_2$)$_p$C(O)N(R$_{10}$)CH(CO$_2$R$_{11}$)(CH$_2$)$_q$X$_3$—;

R$_8$ is NR$_A$R$_B$;

R$_{9A}$ and R$_{9B}$ together are oxo;

X$_2$ is NR$_C$; and

B is aryl.

9. The compound according to claim 2, wherein

L is —(CH$_2$)$_m$X$_1$(CH$_2$)$_n$CH(R$_8$)C(R$_{9A}$)(R$_{9B}$))X$_2$(CH$_2$)$_p$C(O)N(R$_{10}$)CH(CO$_2$R$_{11}$)(CH$_2$)$_q$X$_3$—;

R$_8$ is NR$_A$R$_B$;

R$_{9A}$ and R$_{9B}$ together are oxo;

X$_2$ is NR$_C$;

B is aryl; and

A is

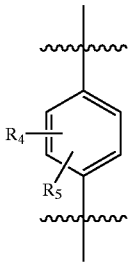

10. The compound according to claim 9, which is

N-[5-({N-acetyl-4-[(carboxycarbonyl)(2-carboxyphenyl)amino]-3-ethylphenylalanyl}amino)pentanoyl]-L-tyrosine.

11. The compound according to claim 2, wherein

L is —(CH$_2$)$_m$X$_1$(CH$_2$)$_n$CH(R$_8$)C(R$_{9A}$)(R$_{9B}$)X$_2$(CH$_2$)$_p$C(O)N(R$_{10}$)CH(CO$_2$R$_{11}$)(CH$_2$)$_q$X$_3$—;

R$_8$ is NR$_A$R$_B$;

R$_{9A}$ and R$_{9B}$ together are oxo;

X$_2$ is NR$_C$; and

B is hydrogen.

12. The compound according to claim 2, wherein

L is —(CH$_2$)$_m$X$_1$(CH$_2$)$_n$CH(R$_8$)C(R$_{9A}$)(R$_{9B}$))X$_2$(CH$_2$)$_p$C(O)N(R$_{10}$)CH(CO$_2$R$_{11}$)(CH$_2$)$_q$X$_3$—;

R$_8$ is NR$_A$R$_B$;

R$_{9A}$ and R$_{9B}$ together are oxo;

X$_2$ is NR$_C$;

B is hydrogen; and

A is

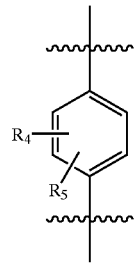

13. The compound according to claim 12, which is

N-[5-({N-acetyl-4-[(carboxycarbonyl)(2-carboxyphenyl)amino]-3-ethylphenylalanyl}amino)pentanoyl]-L-norleucine.

14. The compound according to claim 2, wherein

L is —(CH$_2$)$_m$X$_1$(CH$_2$)$_n$CH(R$_8$)C(R$_{9A}$)(R$_{9B}$)X$_2$(CH$_2$)$_p$EC(O)N(R$_{10}$)CH(CO$_2$R$_{11}$)(CH$_2$)$_q$X$_3$—.

15. The compound according to claim 2, wherein

L is —(CH$_2$)$_m$X$_1$(CH$_2$)$_n$CH(R$_8$)C(R$_{9A}$)(R$_{9B}$)X$_2$(CH$_2$)$_p$EC(O)N(R$_{10}$)CH(CO$_2$R$_{11}$)(CH$_2$)$_q$X$_3$—; and R$_8$ is NR$_A$R$_B$.

16. The compound according to claim 2, wherein

L is —(CH$_2$)$_m$X$_1$(CH$_2$)$_n$CH(R$_8$)C(R$_{9A}$)(R$_{9B}$)X$_2$(CH$_2$)$_p$EC(O)N(R$_{10}$)CH(CO$_2$R$_{11}$)(CH$_2$)$_q$X$_3$—;

R$_8$ is NR$_A$R$_B$; and

R$_{9A}$ and R$_{9B}$ together are oxo.

17. The compound according to claim 2, wherein

L is —(CH$_2$)$_m$X$_1$(CH$_2$)$_n$CH(R$_8$)C(R$_{9A}$)(R$_{9B}$)X$_2$(CH$_2$)$_p$EC(O)N(R$_{10}$)CH(CO$_2$R$_{11}$)(CH$_2$)$_q$X$_3$—;

R$_8$ is NR$_A$R$_B$;

R$_{9A}$ and R$_{9B}$ together are oxo; and

X$_2$ is NR$_C$.

18. The compound according to claim 2, wherein

L is —(CH$_2$)$_m$X$_1$(CH$_2$)$_n$CH(R$_8$)C(R$_{9A}$)(R$_{9B}$)X$_2$(CH$_2$)$_p$EC(O)N(R$_{10}$)CH(CO$_2$R$_{11}$)(CH$_2$)$_q$X$_3$—;

R$_8$ is NR$_A$R$_B$;

R$_{9A}$ and R$_{9B}$ together are oxo;

X$_2$ is NR$_C$; and

B is hydrogen.

19. The compound according to claim 2, wherein

L is —(CH$_2$)$_m$X$_1$(CH$_2$)$_n$CH(R$_4$)C(R$_{9A}$)(R$_{9B}$)X$_2$(CH$_2$)$_p$EC(O)N(R$_{10}$)CH(CO$_2$R$_{11}$)(CH$_2$)$_q$X$_3$—;

R$_8$ is NR$_A$R$_B$;

R$_{9A}$ and R$_{9B}$ together are oxo;

X$_2$ is NR$_C$;

B is hydrogen; and

E is cycloalkyl.

20. The compound according to claim 2, wherein

L is —(CH$_2$)$_m$X$_1$(CH$_2$)$_n$CH(R$_8$)C(R$_{9A}$)(R$_{9B}$)X$_2$(CH$_2$)$_p$EC(O)N(R$_{10}$)CH(CO$_2$R$_{11}$)(CH$_2$)$_q$X$_3$—;

$R_8$ is $NR_AR_B$;
$R_{9A}$ and $R_{9B}$ together are oxo;
$X_2$ is $NR_C$;
B is hydrogen;
E is cycloalkyl; and
A is

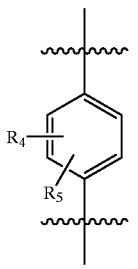

21. The compound according to claim 20, which is N-{[4-({[N-acetyl-4-[(carboxycarbonyl)(2-carboxyphenyl)amino]-3-(2-hydroxyethyl)phenylalanyl]amino}methyl)cyclohexyl]carbonyl}-L-norleucine.

22. The compound according to claim 2, wherein
L is —$(CH_2)_mX_1(CH_2)_nCH(R_8)C(R_{9A})(R_{9B}))X_2(CH_2)_pC(O)N(R_{10})CH(CO_2R_{11})(CH_2)_qX_3$—;
$R_8$ is $NR_AR_B$;
$R_{9A}$ and $R_{9B}$ together are oxo;
$X_2$ is $NR_C$;
$X_3$ is S; and
B is alkyl.

23. The compound according to claim 2, wherein
L is —$(CH_2)_mX_1(CH_2)_nCH(R_8)C(R_{9A})(R_{9B}))X_2(CH_2)_pC(O)N(R_{10})CH(CO_2R_{11})(CH_2)_qX_3$—;
$R_8$ is $NR_AR_B$;
$R_{9A}$ and $R_{9B}$ together are oxo;
$X_2$ is $NR_C$;
$X_3$ is S;
B is alkyl; and
A is

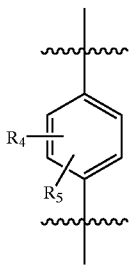

24. The compound according to claim 23, selected from the group consisting of
N-{5-[(N-acetyl-4-[(carboxycarbonyl)(2-carboxyphenyl)amino]-3-ethylphenylalanyl)amino]pentanoyl}-L-methionine;
methyl N-{5-[(N-acetyl-4-[(carboxycarbonyl)(2-carboxyphenyl)amino]-3-ethylphenylalanyl)amino]pentanoyl}-L-methioninate;
N-{5-[(N-acetyl-4-[(carboxycarbonyl)(2-carboxyphenyl)amino]-3-ethylphenylalanyl)amino]pentanoyl}-S-ethyl-L-homocysteine;

N-{5-[(N-acetyl-4-[(carboxycarbonyl)(2-carboxyphenyl)amino]-3-isopropylphenylalanyl)amino]pentanoyl}-L-methionine;

N-{5-[(N-acetyl-4-[(carboxycarbonyl)(2-carboxy-5-chlorophenyl)amino]-3-ethylphenylalanyl)amino]pentanoyl}-L-methionine; and N-(5-{[N-acetyl-4-[(carboxycarbonyl)(2-carboxyphenyl)amino]-3-(2-hydroxyethyl)phenylalanyl]amino}pentanoyl)-L-methionine.

25. The compound according to claim 2, wherein
L is —$(CH_2)_mX_1(CH_2)_nCH(R_8)C(R_{9A})(R_{9B}))X_2(CH_2)_pC(O)N(R_{10})CH(CO_2R_{11})(CH_2)_qX_3$—;
$R_8$ is $NR_AR_B$;
$R_{9A}$ and $R_{9B}$ together are oxo;
$X_2$ is $NR_C$;
$X_3$ is S; and
B is aryl.

26. The compound according to claim 2, wherein
L is —$(CH_2)_mX_1(CH_2)_nCH(R_8)C(R_{9A})(R_{9B}))X_2(CH_2)_pC(O)N(R_{10})CH(CO_2R_{11})(CH_2)_qX_3$—;
$R_8$ is $NR_AR_B$;
$R_{9A}$ and $R_{9B}$ together are oxo;
$X_2$ is $NR_C$;
$X_3$ is S;
B is aryl; and
A is

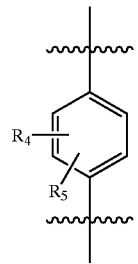

27. The compound according to claim 26, which is
N-{5-[(N-acetyl-4-[(carboxycarbonyl)(2-carboxyphenyl)amino]-3-ethylphenylalanyl)amino]pentanoyl}-S-benzyl-L-cysteine.

28. The compound according to claim 2, wherein
L is —$(CH_2)_mX_1(CH_2)_nCH(R_8)C(R_{9A})(R_{9B}))X_2(CH_2)_pC(O)N(R_{10})CH(CO_2R_{11})(CH_2)_qX_3$—;
$R_8$ is $NR_AR_B$;
$R_{9A}$ and $R_{9B}$ together are oxo;
$X_2$ is $NR_C$;
$X_3$ is S;
B is alkyl; and A is

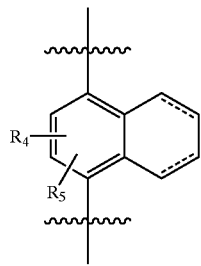

29. The compound according to claim 28, which is N-(5-{[3-(4-[(carboxycarbonyl)(2-carboxyphenyl)amino]-1-naphthyl)-N-(methoxycarbonyl)alanyl]amino}pentanoyl)-L-methionine.

30. The compound according to claim 2, wherein

L is $-(CH_2)_m X_1(CH_2)_n CH(R_8)C(R_{9A})(R_{9B})X_2(CH_2)_p X_3-$.

31. The compound according to claim 2, wherein

L is $-(CH_2)_m X_1(CH_2)_n CH(R_8)C(R_{9A})(R_{9B})X_2(CH_2)_p X_3-$; and $R_8$ is $NR_A R_B$.

32. The compound according to claim 2, wherein

L is $-(CH_2)_m X_1(CH_2)_n CH(R_8)C(R_{9A})(R_{9B})X_2(CH_2)_p X_3-$;

$R_8$ is $NR_A R_B$; and $R_{9A}$ and $R_{9B}$ together are oxo.

33. The compound according to claim 2, wherein

L is $-(CH_2)_m X_1(CH_2)_n CH(R_8)C(R_{9A})(R_{9B})X_2(CH_2)_p X_3-$;

$R_8$ is $NR_A R_B$;

$R_{9A}$ and $R_{9B}$ together are oxo; and is $NR_C$.

34. The compound according to claim 2, wherein

L is $-(CH_2)_m X_1(CH_2)_n CH(R_8)C(R_{9A})(R_{9B})X_2(CH_2)_p X_3-$;

$R_8$ is $NR_A R_B$;

$R_{9A}$ and $R_{9B}$ together are oxo;

$X_2$ is $NR_C$; and $X_3$ is O.

35. The compound according to claim 2, wherein

L is $-(CH_2)_m X_1(CH_2)_n CH(R_B)C(R_{9A})(R_{9B})X_2(CH_2)_p X_3-$;

$R_8$ is $NR_A R_B$;

$R_{9A}$ and $R_{9B}$ together are oxo;

$X_2$ is $NR_C$;

$X_3$ is O; and

B is aryl.

36. The compound according to claim 2, wherein

L is $-(CH_2)_m X_1(CH_2)_n CH(R_8)C(R_{9A})(R_{9B})X_2(CH_2)_p X_3-$;

$R_8$ is $NR_A R_B$;

$R_{9A}$ and $R_{9B}$ together are oxo;

$X_2$ is $NR_C$;

$X_3$ is O;

B is aryl; and

A is

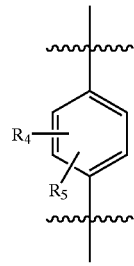

37. The compound according to claim 36, selected from the group consisting of methyl 2-[4-({N-[(allyloxy)carbonyl]-4-[(carboxycarbonyl)(2-carboxyphenyl)amino]-L-phenylalanyl}amino)butoxy]-6-hydroxybenzoate;

methyl 2-{4-[(N-acetyl-4-[(carboxycarbonyl)(2-carboxyphenyl)amino]-3-ethylphenylalanyl)amino]butoxy}-6-hydroxybenzoate;

methyl 4-{4-[(N-acetyl-4-amino-3-ethylphenylalanyl)amino]butoxy}-2-hydroxy-1,1'-biphenyl-3-carboxylate;

2-[4-({N-acetyl-4-[(carboxycarbonyl)(2-carboxyphenyl)amino]-3-ethylphenylalanyl}amino)butoxy]-6-hydroxybenzoic acid;

methyl 6-{4-[(N-acetyl-4-[(carboxycarbonyl)(2-carboxyphenyl)amino]-3-ethylphenylalanyl)amino]butoxy}-3-bromo-2-hydroxybenzoate;

methyl 2-(4-{[4-[(carboxycarbonyl)(2-carboxyphenyl)amino]-N-(methoxycarbonyl)-L-phenylalanyl]amino}butoxy)-6-hydroxy-4-pentylbenzoate;

methyl 2-(4-{[4-[(carboxycarbonyl)(2-carboxyphenyl)amino]-N-(methoxycarbonyl)-L-phenylalanyl]amino}butoxy)-6-hydroxy-4-methoxybenzoate;

methyl 3-(4-{[4-[(carboxycarbonyl)(2-carboxyphenyl)amino]-N-(methoxycarbonyl)-L-phenylalanyl]amino}butoxy)-5-hydroxy-1,1'-biphenyl-4-carboxylate;

methyl 2-(4-{[4-[(carboxycarbonyl)(2-carboxyphenyl)amino]-N-(methoxycarbonyl)-L-phenylalanyl]amino}butoxy)-6-hydroxy-4-methylbenzoate;

methyl 2-(4-{[4-[(carboxycarbonyl)(2-carboxyphenyl)amino]-N-(methoxycarbonyl)-L-phenylalanyl]amino}butoxy)-4-chloro-6-hydroxybenzoate;

methyl 2-(4-{[4-[(carboxycarbonyl)(2-carboxyphenyl)amino]-N-(methoxycarbonyl)-L-phenylalanyl]amino}butoxy)-6-hydroxybenzoate;

4-[(carboxycarbonyl)(2-carboxyphenyl)amino]-N-{4-[2-(aminocarbonyl)-3-hydroxyphenoxy]butyl}-N-(methoxycarbonyl)-L-phenylalaninamide;

methyl 3-(4-{[4-[(carboxycarbonyl)(2-carboxyphenyl)amino]-N-(methoxycarbonyl)-L-phenylalanyl]amino}butoxy)-1-hydroxy-2-naphthoate;

4-[(carboxycarbonyl)(2-carboxyphenyl)amino]-N-(4-{3-hydroxy-2-[(methylamino)carbonyl]phenoxy}butyl)-N-(methoxycarbonyl)-L-phenylalaninamide;

4-[(carboxycarbonyl)(2-carboxyphenyl)amino]-N-(4-{2-[(ethylamino)carbonyl]-3-hydroxyphenoxy}butyl)-N-(methoxycarbonyl)-L-phenylalaninamide;

N-{4-[2-(acetylamino)-3-hydroxyphenoxy]butyl}-4-[(carboxycarbonyl)(2-carboxyphenyl)amino]-N-(methoxycarbonyl)-L-phenylalaninamide; and 4-[(carboxycarbonyl)(2-carboxyphenyl)amino]-N-(4-{2-[(dimethylamino)carbonyl]-3-hydroxyphenoxy}butyl)-N-(methoxycarbonyl)-L-phenylalaninamide.

38. The compound according to claim 2, wherein

L is —$(CH_2)_m X_1 (CH_2)_n CH(R_8)C(R_{9A})(R_{9B})X_2(CH_2)_p X_3$—;

$R_8$ is $NR_A R_B$;

$R_{9A}$ and $R_{9B}$ together are oxo;

$X_2$ is $NR_C$;

$X_3$ is O;

B is aryl; and

A is

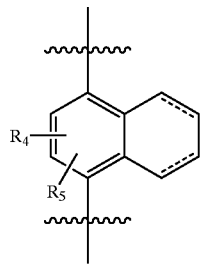

39. The compound according to claim 38, selected from the group consisting of methyl 2-[(5-{[N-acetyl-3-(4-amino-1-naphthyl)-L-alanyl]amino}pentyl)oxy]-6-hydroxy-4-methylbenzoate; and 3-({5-[(N-acetyl-3-{4-[(carboxycarbonyl)(2-carboxyphenyl)amino]-1-naphthyl}-L-alanyl)amino]pentyl}oxy)-2-naphthoic acid.

40. The compound according to claim 2, wherein

L is —$(CH_2)_m X_1 (CH_2)_n CH(R_8)C(R_{9A})(R_{9B})X_2(CH_2)_p X_3$—; and $R_8$ is hydrogen.

41. The compound according to claim 2, wherein

L is —$(CH_2)_m X_1 (CH_2)_n CH(R_8)C(R_{9A})(R_{9B})X_2(CH_2)_p X_3$—;

$R_8$ is hydrogen; and $R_{9A}$ and $R_{9B}$ together are oxo.

42. The compound according to claim 2, wherein

L is —$(CH_2)_m X_1 (CH_2)_n CH(R_8)C(R_{9A})(R_{9B})X_2(CH_2)_p X_3$—;

$R_8$ is hydrogen;

$R_{9A}$ and $R_{9B}$ together are oxo; and $X_2$ is $NR_C$.

43. The compound according to claim 2, wherein

L is —$(CH_2)_m X_1 (CH_2)_n CH(R_8)C(R_{9A})(R_{9B})X_2(CH_2)_p X_3$—;

$R_8$ is hydrogen;

$R_{9A}$ and $R_{9B}$ together are oxo;

$X_2$ is $NR_C$; and $X_3$ is O.

44. The compound according to claim 2, wherein

L is —$(CH_2)_m X_1 (CH_2)_n CH(R_8)C(R_{9A})(R_{9B})X_2(CH_2)_p X_3$—;

$R_8$ is hydrogen;

$R_{9A}$ and $R_{9B}$ together are oxo;

$X_2$ is $NR_C$;

$X_3$ is O; and

B is aryl.

45. The compound according to claim 2, wherein

L is —$(CH_2)_m X_1 (CH_2)_n CH(R_8)C(R_{9A})(R_{9B})X_2(CH_2)_p X_3$—;

$R_8$ is hydrogen;

$R_{9A}$ and $R_{9B}$ together are oxo;

$X_2$ is $NR_C$;

$X_3$ is O; and

B is aryl; and

A is

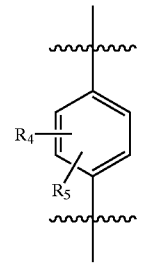

46. The compound according to claim 45, which is methyl 2-(4-{[3-(4-[(carboxycarbonyl)(2-carboxyphenyl)amino]-3-ethylphenyl)propanoyl]amino}butoxy)-6-hydroxybenzoate.

47. The compound according to claim 2, wherein

L is —$(CH_2)_m X_1 (CH_2)_n CH(R_8)C(R_{9A})(R_{9B})X_2(CH_2)_p X_3$—;

$R_8$ is hydrogen;

$R_{9A}$ and $R_{9B}$ together are oxo;

$X_2$ is $NR_C$;

$X_3$ is O;

B is aryl; and

A is

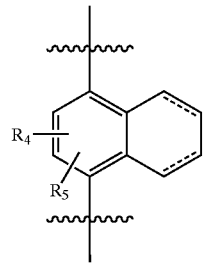

48. The compound according to claim 47, which is 2-((carboxycarbonyl){4-[3-({4-[3-hydroxy-2-(methoxycarbonyl)phenoxy]butyl}amino)-3-oxopropyl]-[(carboxycarbonyl)(2-carboxyphenyl)amino]-1-naphthyl}amino)benzoic acid.

49. The compound according to claim 2, wherein

L is —$(CH_2)_m X_1 (CH_2)_n CH(R_8)C(R_{9A})(R_{9B})X_2(CH_2)_p X_3$—;

$R_8$ is hydrogen; and $R_{9A}$ is alkyl.

50. The compound according to claim 2, wherein

L is —$(CH_2)_m X_1 (CH_2)_n CH(R_8)C(R_{9A})(R_{9B})X_2(CH_2)_p X_3$—;

$R_8$ is hydrogen;

$R_{9A}$ is alkyl; and
$X_2$ is $NR_C$.

51. The compound according to claim 2, wherein
L is $-(CH_2)_mX_1(CH_2)_nCH(R_8)C(R_{9A})(R_{9B})X_2(CH_2)_pX_3-$;
$R_8$ is hydrogen;
$R_{9A}$ is alkyl;
$X_2$ is $NR_C$; and
$X_3$ is O.

52. The compound according to claim 2, wherein
L is $-(CH_2)_mX_1(CH_2)_nCH(R_8)C(R_{9A})(R_{9B})X_2(CH_2)_pX_3-$;
$R_8$ is hydrogen;
$R_{9A}$ is alkyl;
$X_2$ is $NR_C$;
$X_3$ is O; and
B is aryl.

53. The compound according to claim 2, wherein
L is $-(CH_2)_mX_1(CH_2)_nCH(R_8)C(R_{9A})(R_{9B})X_2(CH_2)_pX_3-$;
$R_8$ is hydrogen;
$R_{9A}$ is alkyl;
$X_2$ is $NR_C$;
$X_3$ is O;
B is aryl; and
A is

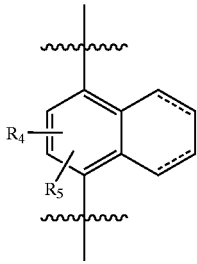

54. The compound according to claim 53, which is methyl 2-(4-{[3-(4-[(carboxycarbonyl)(2-carboxyphenyl)amino]-1-naphthyl)-1-methylpropyl]amino}butoxy)-6-hydroxybenzoate.

55. The compound according to claim 2, wherein
L is $-(CH_2)_mX_1(CH_2)_nCH(R_8)C(R_{9A})(R_{9B})X_2(CH_2)_pX_3-$;
$R_8$ is hydrogen; and
$R_{9A}$ and $R_{9B}$ are both hydrogen.

56. The compound according to claim 2, wherein
L is $-(CH_2)_mX_1(CH_2)_nCH(R_8)C(R_{9A})(R_{9B})X_2(CH_2)_pX_3-$;
$R_8$ is hydrogen;
$R_{9A}$ and $R_{9B}$ are both hydrogen; and
$X_2$ is $NR_C$.

57. The compound according to claim 2, wherein
L is $-(CH_2)_mX_1(CH_2)_nCH(R_8)C(R_{9A})(R_{9B})X_2(CH_2)_pX_3-$;
$R_8$ is hydrogen;
$R_{9A}$ and $R_{9B}$ are both hydrogen;
$X_2$ is $NR_C$; and
$X_3$ is O.

58. The compound according to claim 2, wherein
L is $-(CH_2)_mX_1(CH_2)_nCH(R_8)C(R_{9A})(R_{9B})X_2(CH_2)_pX_3-$;
$R_8$ is hydrogen;
$R_{9A}$ and $R_{9B}$ are both hydrogen;
$X_2$ is $NR_C$;
$X_3$ is O; and
B is aryl.

59. The compound according to claim 2, wherein
L is $-(CH_2)_mX_1(CH_2)_nCH(R_8)C(R_{9A})(R_{9B})X_2(CH_2)_pX_3-$;
$R_8$ is hydrogen;
$R_{9A}$ and $R_{9B}$ are both hydrogen;
$X_2$ is $NR_C$;
$X_3$ is O;
B is aryl; and
A is

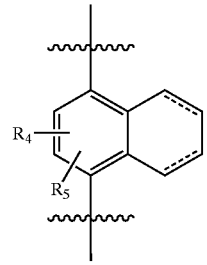

60. The compound according to claim 59, which is methyl 2-(4-{[3-(4-[(carboxycarbonyl)(2-carboxyphenyl)amino]-1-naphthyl)propyl]amino}butoxy)-6-hydroxybenzoate.

61. The compound according to claim 2, wherein
L is $-(CH_2)_mX_1(CH_2)_nCH(R_8)C(R_{9A})(R_{9B})X_2(CH_2)_pX_3(CH_2)_qX_4-$.

62. The compound according to claim 2, wherein
L is $-(CH_2)_mX_1(CH_2)_nCH(R_8)C(R_{9A})(R_{9B})X_2(CH_2)_pX_3(CH_2)_qX_4-$; and
$R_8$ is $NR_AR_B$.

63. The compound according to claim 2, wherein
L is $-(CH_2)_mX_1(CH_2)_nCH(R_8)C(R_{9A})(R_{9B})X_2(CH_2)_pX_3(CH_2)_qX_4-$;
$R_8$ is $NR_AR_B$; and
$R_{9A}$ and $R_{9B}$ together are oxo.

64. The compound according to claim 2, wherein
L is $-(CH_2)_mX_1(CH_2)_nCH(R_8)C(R_{9A})(R_{9B})X_2(CH_2)_pX_3(CH_2)_qX_4-$;
$R_8$ is $NR_AR_B$;
$R_{9A}$ and $R_{9B}$ together are oxo; and
$X_2$ is $NR_C$.

65. The compound according to claim 2, wherein
L is $-(CH_2)_mX_1(CH_2)_nCH(R_8)C(R_{9A})(R_{9B})X_2(CH_2)_pX_3(CH_2)_qX_4-$;
$R_8$ is $NR_AR_B$;
$R_{9A}$ and $R_{9B}$ together are oxo;
$X_2$ is $NR_C$; and
$X_3$ is O.

66. The compound according to claim 2, wherein
L is $-(CH_2)_mX_1(CH_2)_nCH(R_8)C(R_{9A})(R_{9B})X_2(CH_2)_pX_3(CH_2)_qX_4-$;

$R_8$ is $NR_AR_B$;

$R_{9A}$ and $R_{9B}$ together are oxo;

$X_2$ is $NR_C$;

$X_3$ is O; and $X_4$ is O.

67. The compound according to claim 2, wherein

L is $-(CH_2)_mX_1(CH_2)_nCH(R_8)C(R_{9A})(R_{9B})X_2(CH_2)_pX_3(CH_2)_qX_4-$;

$R_8$ is $NR_AR_B$;

$R_{9A}$ and $R_{9B}$ together are oxo;

$X_2$ is $NR_C$;

$X_3$ is O;

$X_4$ is O; and

B is aryl.

68. The compound according to claim 2, wherein

L is $-(CH_2)_mX_1(CH_2)_nCH(R_8)C(R_{9A})(R_{9B})X_2(CH_2)_pX_3(CH_2)_qX_4-$;

$R_8$ is $NR_AR_B$;

$R_{9A}$ and $R_{9B}$ together are oxo;

$X_2$ is $NR_C$;

$X_3$ is O;

$X_4$ is O;

B is aryl; and

A is

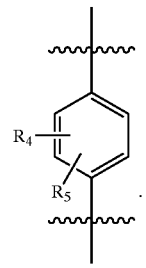

69. The compound according to claim 68, which is methyl 2-{2-(2-({N-[(allyloxy)carbonyl]-4-[(carboxycarbonyl)(2-carboxyphenyl)amino)-L-phenylalanyl}amino)ethoxy]ethoxy}-6-hydroxybenzoate.

70. A pharmaceutical composition comprising a therapeutically effective amount of a compound of claim 1 in combination with a pharmaceutically acceptable carrier.

71. A method of treating diabetes by selectively inhibiting protein tyrosine phosphatase 1B comprising administering a therapeutically effective amount of a compound of claim 1.

72. A method of treating diabetes caused by overexpressed or altered protein tyrosine phosphatase 1B comprising administering a therapeutically effective amount of a compound of claim 1.

* * * * *